(12) United States Patent
Hashimoto et al.

(10) Patent No.: US 7,910,719 B2
(45) Date of Patent: Mar. 22, 2011

(54) METHOD OF DETECTING HUMAN PAPILLOMA VIRUS BY USING NUCLEIC ACID AMPLIFICATION METHOD AND NUCLEIC ACID CHAIN-IMMOBILIZED CARRIER

(75) Inventors: Koji Hashimoto, Atsugi (JP); Keiko Ito, Kawasaki (JP); Naoko Nakamura, Kawasaki (JP); Hideki Horiuchi, Yokohama (JP); Michie Hashimoto, Tokyo (JP); Osamu Sato, Tokyo (JP)

(73) Assignees: Kabushiki Kaisha Toshiba, Tokyo (JP); Sekisui Medical Co., Ltd., Nihonbashi (JP)

( * ) Notice: Subject to any disclaimer, the term of this patent is extended or adjusted under 35 U.S.C. 154(b) by 0 days.

(21) Appl. No.: 12/134,420

(22) Filed: Jun. 6, 2008

(65) Prior Publication Data
US 2009/0035750 A1    Feb. 5, 2009

Related U.S. Application Data

(63) Continuation of application No. PCT/JP2006/032501, filed on Dec. 8, 2006.

(30) Foreign Application Priority Data

Dec. 8, 2005  (JP) ................. 2005-354826
Jul. 7, 2006  (JP) ................. 2006-187871
Nov. 15, 2006 (JP) .................. PCT/JP2006/0323261

(51) Int. Cl.
C07H 21/04    (2006.01)
C12Q 1/68     (2006.01)
C12P 19/34    (2006.01)

(52) U.S. Cl. ............................ 536/24.3; 435/6; 435/91.2

(58) Field of Classification Search ........................ None
See application file for complete search history.

(56) References Cited

U.S. PATENT DOCUMENTS

| 5,447,839 | A * | 9/1995 | Manos et al. .................. 435/5 |
| 6,352,825 | B1 | 3/2002 | Meijer et al. |
| 6,410,278 | B1 * | 6/2002 | Notomi et al. ................ 435/91.2 |
| 2005/0186590 | A1 * | 8/2005 | Crothers et al. .................. 435/6 |

FOREIGN PATENT DOCUMENTS

| JP | 9-509062 | 9/1997 |
| JP | 2002-186781 | 7/2002 |
| JP | 2005-95043 | 4/2005 |
| WO | 2005/056839 | 6/2005 |
| WO | WO 2005100598 A1 * | 10/2005 |

OTHER PUBLICATIONS

GenBank Accession No. AF140365 for the HPV-16 capsid protein gene, Jun. 14, 1999 [online], [retrieved on Aug. 4, 2010], retrieved from the Internet: <URL: www.ncbi.nlm.nih.gov/nuccore/5052374>.*
Lin et al. A simple method for the detection and genotyping of high-risk human papillomavirus using seminested polymerase chain reaction and reverse hybridization. Gynecologic Oncology (2005) 96: 84-91.*
Bernhard Kleter, et al., "Development and Clinical Evaluation of a Highly Sensitive PCR-Reverse Hybridization Line Probe Assay for Detection and Identification of Anogenital Human Papillomavirus", Journal of Clinical Microbiology, Aug. 1999, pp. 2508-2517, vol. 37.
Suzanne D. Vernon, et al.; "Bioelectronic DNA detection of human papillomaviruses using eSensor™ : a model system for detection of multiple pathogens" BMC Infectious Diseases, 3:12(2003).
Roger A. Hubbard, PhD., Human Papillomavirus Testing Methods, Arch Pathol Lab Med-vol. 127, Aug. 2003, pp. 940-945.
K. Nagamine, et al., "Accelerated reaction by loop-mediated isothermal amplification using loop primers", Molecular and Cellular Probes (2002), 16, pp. 223-229.
Masayoshi Takahashi, et al., "Construction of an electrochemical DNA chip for simultaneous genotyping of single nucleotide polymorphisms", Analyst, 2005, 130, pp. 687-693.
Oct. 3, 1995; Primers and Process for Detecting Human Papillomavirus Genotypes by PCR, GenBank Accession No. A30625.
Jun. 7, 2005, "Detection of HPV types in cervical brush samples of clinical patients in Beijing and other Northern China cities", GenBank Accession No. DQ003077.
Masanori Hagiwara, et al., "Loop-Mediated Isothermal Amplification Method for Detection of Human Papillomavirus Type 6, 11, 16, and 18", Journal of Medical Virology 79-605-615 (2007).
Kentaro Nagamine, et al., "Isolation of Single-Stranded DNA from Loop-Mediated Isothermal Amplification Products", Biochemical and Biophysical Research Communications, vol. 290, No. 4, XP-002312265, Feb. 1, 2002, pp. 1195-1198.
Jonathan E. Baines, et al., "Consensus-degenerate hybrid oligonucleotide primers (CODEHOP) for the detection of novel papillomaviruses and their application to esophageal and tonsillar carcinomas", Journal of Virological Methods, vol. 123, 2005, pp. 81-87.

* cited by examiner

*Primary Examiner* — Young J Kim
*Assistant Examiner* — Angela M Bertagna
(74) *Attorney, Agent, or Firm* — Oblon, Spivak, McClelland, Maier & Neustadt, L.L.P.

(57) ABSTRACT

Provided is a nucleic acid primer for LAMP amplification for use in the detection of human papilloma virus and identification of its genotype. The present invention also provides a method of detecting human papilloma virus and identifying its genotype, includes a step of amplifying the nucleic acid chains in a sample in LAMP reaction by using multiple primers including at least one primer selected from the nucleic acid primers according to the present invention and a step of detecting presence of amplified products after the amplification reaction and identifying their genotypes.

7 Claims, 7 Drawing Sheets m: φx174/HaeIII dig.
n: ddH₂O m: φx174/HaeIII dig.
n: ddH₂O

Reaction A
Reaction B
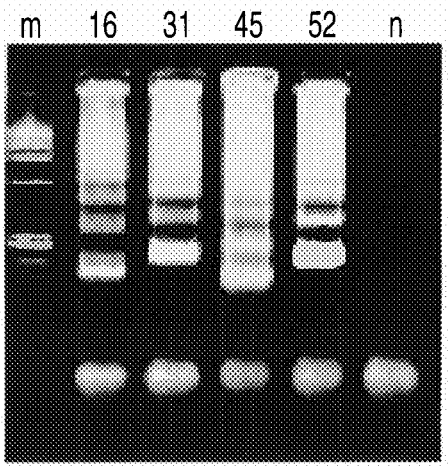
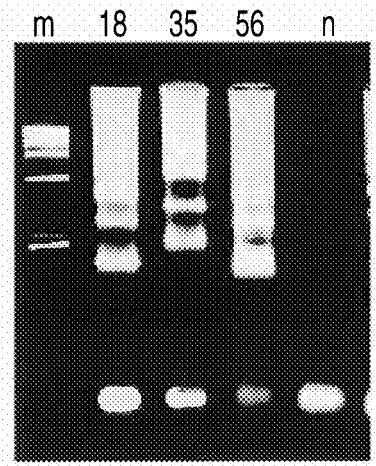
Reaction C
Reaction D
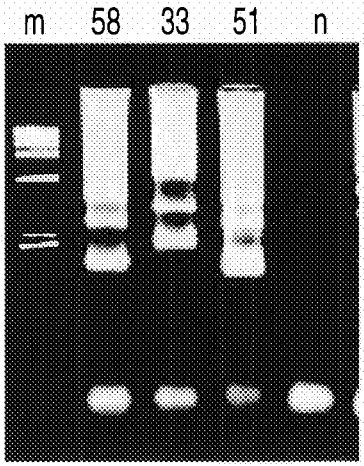
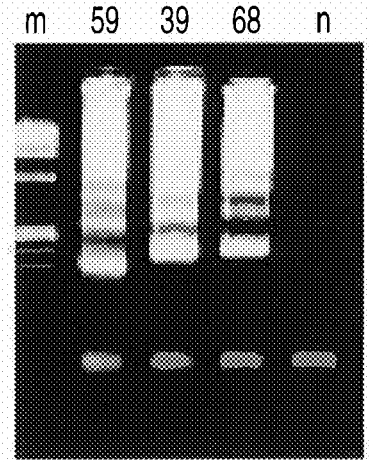
F I G. 10

```
5821 ttcctaaagt atcaggatta caatacaggg tatttagaat acatttacct gaccccaata
5881 agtttggttt tcctgacacc tcatttata atccagatac acagcggctg gtttgggcct
5941 gtgtaggtgt tgaggtaggt cgtggtcagc cattaggtgt gggcattagt ggccatcctt
6001 tattaaataa attggatgac acagaaaatg ctagtgctta tgcagcaaat gcaggtgtgg
6061 ataatagaga atgtatatct atggattaca aacaaacaca attgtgttta attggttgca
6121 aaccacctat aggggaacac tggggcaaag gatcccoatg taccaatgtt gcagtaaatc
6181 caggtgattg tccaccatta gagttaataa acacagttat tcaggatggt gatatggttc
6241 atactggctt tggtgctatg gactttacta cattacaggc taacaaaagt gaagttccac
6301 tggatatttg tacatctatt tgcaaatatc cagattatat taaaatggtg tcagaaccat
6361 atggcgacag cttattttt tatttacgaa gggaacaaat gtttgttaga catttattta
6421 atagggctgg tactgttggg gaaaatgtac cagacgattt atacattaaa ggctctgggt
6481 ctactgcaaa tttagccagt tcaaattatt ttcctacacc tagtggttct atggttacct
6541 ctgatgccca aatattcaat aaaccttatt ggttacaacg agcacagggc cacaataatg
6601 gcatttgttg gggtaaccaa ctatttgtta ctgttgttga tactacacgc agtacaaata
6661 tgtcattatg tgctgccata tctacttcag aaactacata taaaaatact aactttaagg
6721 agtacctacg acatggggaa gaatatgatt tacagtttat ttttcaactg tgcaaaataa
6781 ccttaactgc agacgttatg acatacatac attctatgaa ttccactatt ttggaggact
6841 ggaattttgg tctacaacct ccccaggag gcacactaga agatacttat aggttttgtaa
6901 cccaggcaat tgcttgtcaa aaacatacac ctccagcacc taaagaagat gatccccta
6961 aaaaatacac tttttgggaa gtaaatttaa aggaaaagtt ttctgcagac ctagatcagt
7021 ttccttagg acgcaaattt ttactacaag caggattgaa ggccaaacca aaatttacat
7081 taggaaaacg aaaagctaca cccaccacct catctaccctc tacaactgct aaacgcaaaa
7141 aacgtaagct gtaagtattg tatgtatgtt gaattagtgt tgtttgttgt gtatatgttt
7201 gtatgtgctt gtatgtgctt gtaaatatta agttgtatgt gtgtttgtat gtatggtata
7261 ataaacacgt gtgtatgtgt ttttaaatgc ttgtgtaact attgtgtcat gcaacataaa
7321 taaacttatt gttcaacac ctactaattg tgttgtggtt attcattgta tataaactat
7381 atttgctaca tcctgttttt gtttttatata tactatattt tgtagcgcca ggcccatttt
7441 gtagcttcaa ccgaattcgg ttgcatgctt tttggcacaa aatgtgtttt tttaaatagt
7501 tctatgtcag caactatggt ttaaacttgt acgtttcctg cttgccatgc gtgccaaatc
7561 cctgttttcc tgacctgcac tgcttgccaa ccattccatt gtttttaca ctgcactatg
7621 tgcaactact gaatcactat gtacattgtg tcatataaaa taaatcacta tgcgccaacg
7681 cctacatac cgctgttagg cacatatttt tggcttgttt taactaacct aattgcatat
7741 ttggcataag gtttaaactt ctaaggccaa ctaaatgtca ccctagttca tacatgaact
7801 gtgtaaaggt tagtcataca ttgttcattt gtaaaactgc acatggggtgt gtgcaaaccg
7861 atttttgggtt acacatttac aagcaactta tataataata ctaa
```

SEQ ID No. 4  
SEQ ID No. 2  
SEQ ID No. 3  
SEQ ID No. 1  
SEQ ID No. 5  
SEQ ID No. 6

FIG. 11

METHOD OF DETECTING HUMAN PAPILLOMA VIRUS BY USING NUCLEIC ACID AMPLIFICATION METHOD AND NUCLEIC ACID CHAIN-IMMOBILIZED CARRIER

CROSS REFERENCE TO RELATED APPLICATIONS

This is a Continuation Application of PCT Application No. PCT/JP2006/325010, filed Dec. 8, 2006, which was published under PCT Article 21(2) in English.

This application is based upon and claims the benefit of priority from prior Japanese Patent Applications No. 2005-354826, filed Dec. 8, 2005; No. 2006-187871, filed Jul. 7, 2006; and International Application No. PCT/JP2006/323261, filed Nov. 15, 2006, the entire contents of all of which are incorporated herein by reference.

BACKGROUND OF THE INVENTION

1. Field of the Invention

The present invention relates to a nucleic acid primer sequence, a kit, and a nucleic acid chain-immobilized carrier for detection of human papilloma virus and identification of its genotype, and a method of detecting human papilloma virus by using a nucleic acid amplification method.

2. Description of the Related Art

Human papilloma virus (HPV) infection was reported as a cause of uterine cervical cancer in the 1980's, and in particular, the relationship between cancer malignancy and HPV genotype is attracting attention. HPV is also considered to be the cause of cancers other than uterine cervical cancer such as cancers of the genital organs and oral mucosa, and there has been a demand for a rapid and accurate method of detecting HPV. Hitherto known were a method of detecting a malignant or benign genotype by using a DNA/RNA-recognizing antibody, and a method of amplifying a region containing a sequence characteristic to a genotype in polymerase chain reaction (PCR) and identifying the genotype finally by using a genotype-specific probe. However, the former method, which does not identify the genotype, is not applicable to the test for vaccine administration currently under development. Alternatively, the latter method of using the PCR method had disadvantages such as complicated procedure of pretreatment for example nucleic acid extraction, demand for a complex temperature-regulating device such as thermal cycler, and longer reaction period of two hours or more. In addition, the PCR method has a possibility that, if an incorrect complementary strand happens to be synthesized, the product may be used as a template in amplification, consequently leading to incorrect judgment. Actually, it is difficult to control specific amplification only with a difference of one nucleotide at the terminal of a primer.

For detection by using a DNA chip, gene products amplified by the PCR method are generally double-stranded chains. Thus, there emerged a problem that the complementary strands became competitors to the probe, lowering hybridization efficiency and detection sensitivity in the hybridization reaction with a probe. Accordingly, for example, a method of decomposing or separating the complementary strand is employed to make the target gene product into a single strand. However, these methods still have problems such as the higher cost and complicated procedure because of the use of enzymes or magnetic beads, and there exists a need for a new method replacing such conventional methods.

BRIEF SUMMARY OF THE INVENTION

An object of the present invention is to provide a nucleic acid primer for detection of an HPV nucleotide sequence present in LAMP amplification products when principle of a LAMP method allowing simple and rapid detection of nucleic acids is applied, and an HPV-detection method using the nucleic acid primer.

The inventions employed a method different from the PCR method, i.e., LAMP method, for identification of the HPV genotype. Thus, it is possible to identify the genotype easily. However, the LAMP products, which have complicated high-order structures, cause physical hindrance with the probe-bound support during hybridization, which in turn lead to deterioration of the hybridization efficiency (see, for example, JP-A 2005-095043 (KOKAI)). Accordingly, in the present invention, the primer is so designed that the human papilloma virus-derived target sequence becomes located in the single-stranded loop region of the LAMP product, differently from before.

According to one aspect of the present invention, there is provided a nucleic acid primer for LAMP amplification for use in the detection of human papilloma virus and identification of its genotype, the nucleic acid primer being selected from the following (a)-(f); (a) a nucleic acid primer containing, on the same chain, a sequence complementary to a sequence selected from those in a first sequence group listed in Table 1 and a sequence selected from those in a second sequence group listed in Table 2; (b) a nucleic acid primer containing, on the same chain, a sequence complementary to a sequence selected from those in the first sequence group and a sequence selected from those in a third sequence group listed in Table 3; (c) a nucleic acid primer containing, on the same chain, a sequence complementary to a sequence selected from those in the second sequence group and a sequence selected from those in the third sequence group; (d) a nucleic acid primer containing a sequence that differs from a selected sequence of one of the nucleic acid primers (a), (b), and (c), by insertion, deletion, or substitution of one or more bases, and capable to hybridize with a nucleic acid chain having a sequence complementary to the selected sequence of one of the nucleic acid primers (a), (b), and (c); (e) a nucleic acid primer containing a sequence selected from those in a fourth sequence group listed in Table 4 or a sequence complementary thereto; and (f) a nucleic acid primer containing a sequence that differs from a selected sequence of one of the nucleic acid primers (e), by insertion, deletion, or substitution of one or more bases, and capable to hybridize with a nucleic acid chain having a sequence complementary to the selected sequence of one of the nucleic acid primers (e).

According to another aspect of the present invention, there is provided a method of detecting human papilloma virus and identifying its genotype, comprising a step of amplifying the nucleic acid chains in a sample in LAMP reaction by using multiple primers including at least one primer selected from the nucleic acid primers above and a step of detecting presence of amplified products after the amplification reaction and identifying their genotypes.

According to yet another aspect of the present invention, there is provided a nucleic acid chain-immobilized support carrying an immobilized human papilloma virus- or genotype-specific nucleic acid chain for detection of human-papilloma-virus LAMP amplification products. Preferably, the nucleic acid chain immobilized is (g) a nucleic acid probe containing a sequence selected from those in a fifth sequence group listed in Table 5 or a sequence complementary thereto, or (h) a nucleic acid probe containing a sequence that differs from a selected sequence of one of the nucleic acid probe (g), by insertion, deletion, or substitution of one or more bases, and capable to hybridize with a nucleic acid chain having a sequence complementary to the selected sequence of one of the nucleic acid probe (g).

BRIEF DESCRIPTION OF THE SEVERAL
VIEWS OF THE DRAWING

FIG. 3 is a schematic chart showing an amplification method for producing a nucleic acid for measurement according to the present invention;

Figure 9:
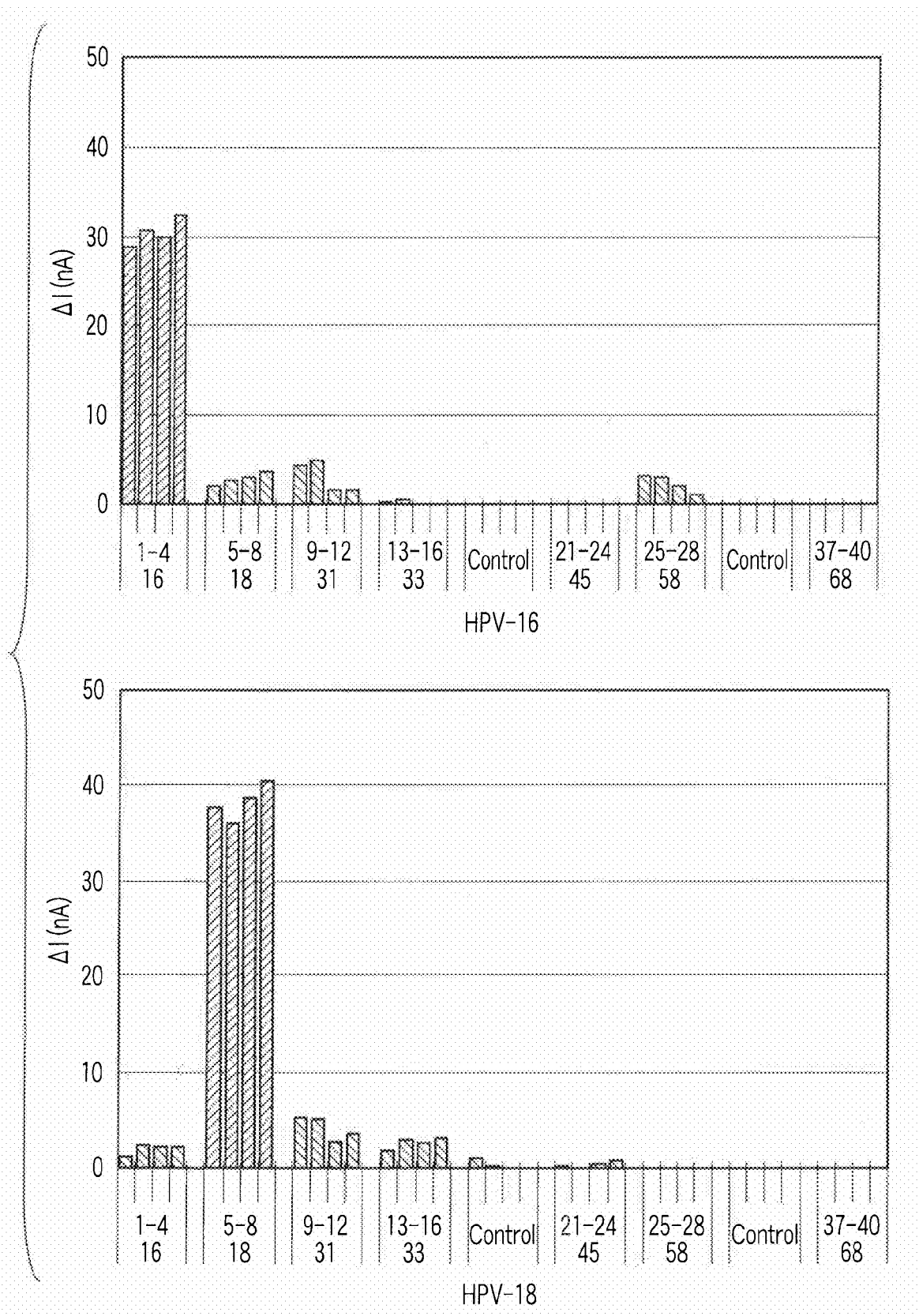

FIG. 9 includes charts showing examples of results detected by a current-detecting DNA chip;

FIG. 10 include charts showing examples of the electrophoretic photographs after LAMP amplification; and FIG. 11 is a chart showing an HPV sequence and regions usable as a primer or probe according to the present invention.

DETAILED DESCRIPTION OF THE INVENTION

An amplification method used in the present invention, the "LAMP method", is a kind of isothermal polymerase chain reaction, and uses 4 or 6 kinds of primers. The LAMP method is reported to be higher in amplification efficiency than the PCR method and also resistant to the influence by impurities in a sample. It is thus possible to detect human papilloma virus in a smaller amount easily with simple pretreatment of the sample.

Figure 1:
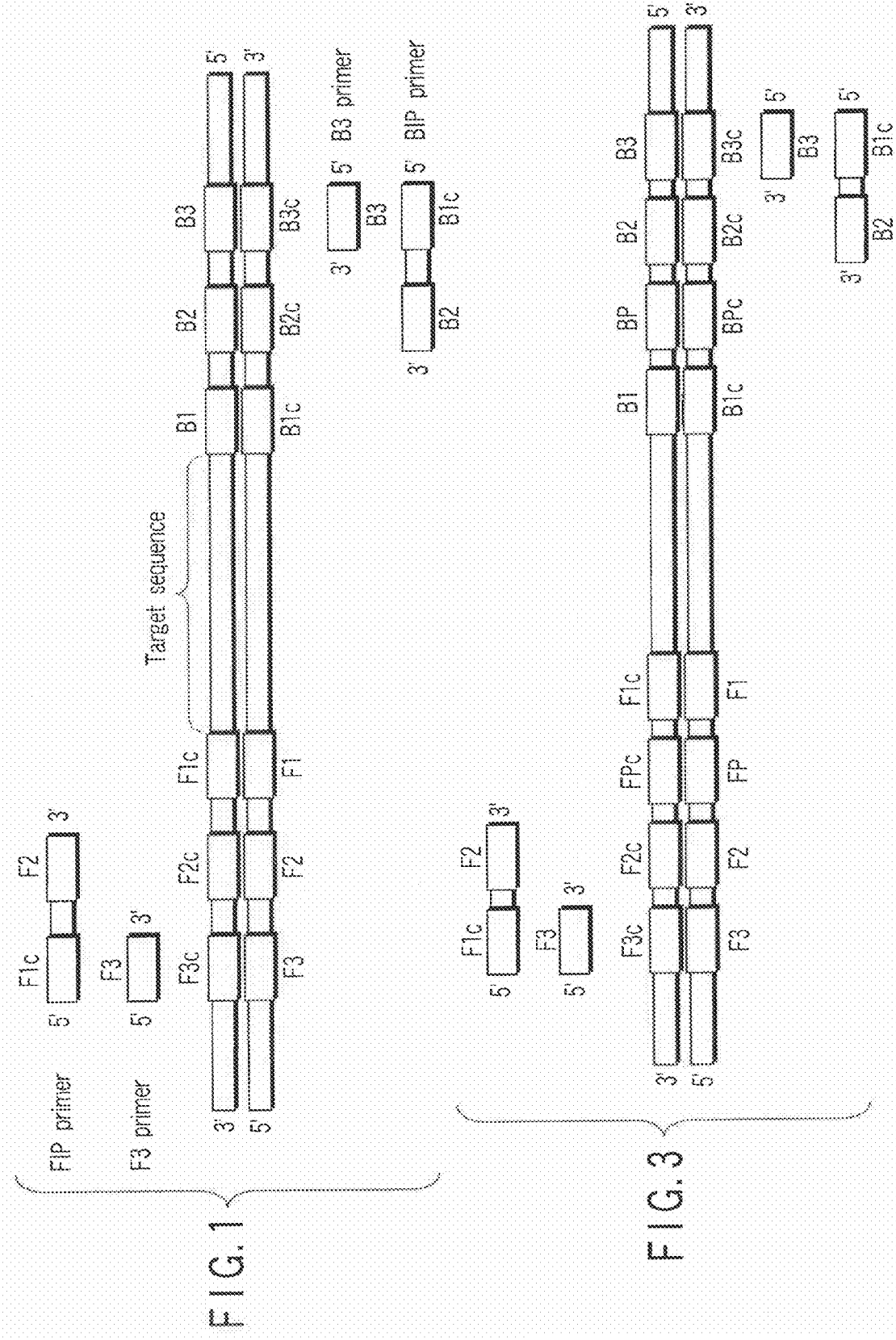
FIG. 1 is a schematic chart showing an amplification method in a conventional LAMP method.
Figure 2:
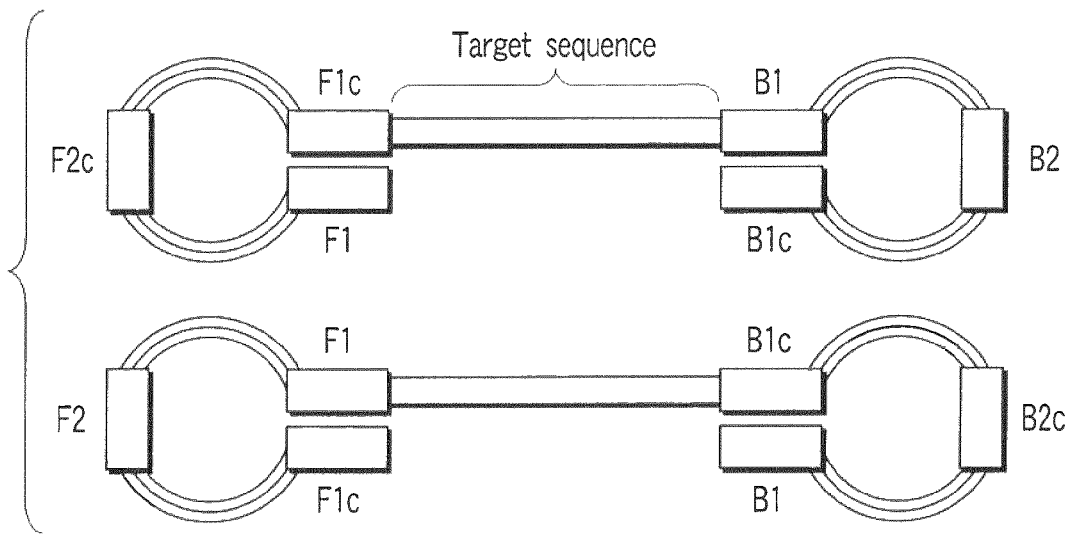
FIG. 2 is a schematic chart showing amplification products obtained by the conventional LAMP method.

The primer design and amplification products obtained in the LAMP method will be described with reference to FIGS. 1 and 2. FIG. 1 shows a double strand DNA to be detected. Conventionally, a target sequence has been located in the center of a stem-and-loop structure of LAMP amplification products (FIG. 2). In amplifying and detecting the target sequence, a total of four kinds of primer sequences (FIP, F3, BIP, and B3 primers) are determined from the sequences located at both sides of the target sequence. The FIP and BIP primers each contain two regions (FIP=F1c+F2, BIP=B2+B1c). A total of six regions used in these primers will be called primer regions below. LAMP amplification by using the four kinds of primers gives amplification products with the dumbbell-shaped stem-and-loop structure shown in FIG. 2, each of them being complementary to each strand of the DNA shown in FIG. 1. The amplification mechanism is not described here, but may be referred, for example, to in JP-A 2002-186781 (KOKAI).

Figure 4:
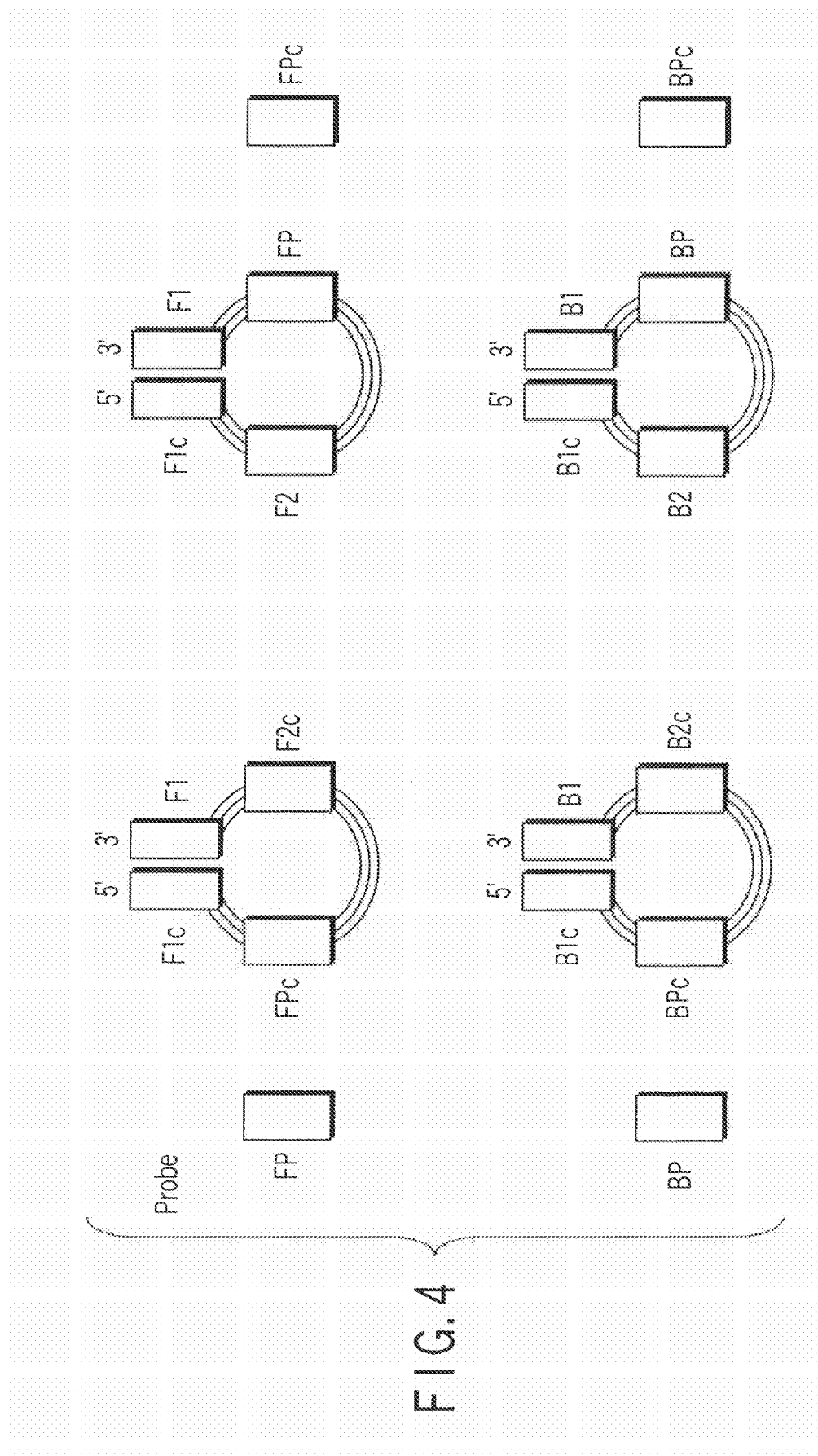
FIG. 4 is a schematic chart showing nucleic acids for measurement according to the present invention.

On the other hand, in the present invention, the primers are designed such that the target sequence is placed in the single-stranded loop region, unlike the conventional target-sequence site shown in FIG. 2. Specifically as shown in FIG. 3, in the invention, six primer regions are so placed that the target sequence (any one of FPc, FP, BP, and BPc in FIG. 3) is located between primer regions F1 and F2 (including F2 region), between primer regions F2c and F1c (including F2c region), between primer regions B1 and B2 (including B2 region), and/or between primer regions B2c and B1c (including B2c region). The target sequence may be placed in any one of the single-stranded loop regions formed between the regions above, and thus, the loop region between primer regions F1 and F2 includes the F2 region. A part of LAMP amplification products, which is shown in FIG. 4, are obtained by preparing four kinds of primers according to the six primer regions thus determined and performing LAMP amplification by using these primers. In the LAMP amplification products, target sequences FPc, FP, BP, and BPc are located in the single-stranded loops in the dumbbell structure of the amplification products. On the other hand, primer regions F1c and F1, and B1c and B1, have sequences complementary to each other, and thus, form double strands by selfhybridization. Some of the target sequences contained in the amplification products are in the single stranded state as shown in FIG. 4. For this reason, it is possible to detect the target sequences by specific hybridization to probe nucleic acids (FP, FPc, BP, and BPc) complimentary to respective target sequences without denaturation processing, as shown in the figure. The term "specific hybridization" means that it is possible to detect a slight difference caused by single nucleotide polymorphism (SNP) or mutation if present.

The present invention detects the genotype of HPV virus by applying such a primer structure to HPV virus.

A sequence shown in FIG. 11 is an HPV virus sequence. A region containing SEQ ID Nos. 1, 2 and 3 in the figure is known to be preserved among many HPV viruses. Alternatively, the SEQ ID No. 4 shows a region where it is known that there is polymorphism between malignant and benign tumors. In detecting the HPV viral genotype, polymorphism is detected, for example, by using a sequence of the region corresponding to the SEQ ID No. 4 as a target sequence. In such a case, for example, sequences selected from first sequence group (Table 1) and second sequence group (Table 2), or for example sequences selected from first sequence group and third sequence group (Table 3), are used as the sequence corresponding to the primer regions F1 and F2. The first, second, and third sequence groups are the sequence groups shown in the following Tables 1 to 3, and respectively correspond to the regions of SEQ ID No. 1, 2, and 3 in FIG. 11. The sequence in these regions varies according to its viral type, and is not always identical with the sequence shown in FIG. 11. In addition, a primer set consisting of BIP and B3 primers is also needed in actual LAMP amplification. It is possible to use the sequences of SEQ ID Nos. 5 and 6 in FIG. 11 or the complementary sequences thereof. The primer according to the invention for use is preferably a primer having, on the same chain in the direction from 5' to 3', a sequence complementary to a sequence selected from those in the first sequence group and a sequence selected from those in the second sequence group bound to each other, a sequence selected from those in the second sequence group and a sequence complementary to a sequence selected from those in the first sequence group bound to each other, a sequence complementary to a sequence selected from those in the first sequence group and a sequence selected from those in the third sequence group bound to each other, a sequence selected from those in the third sequence group and a sequence complementary to a sequence selected from those in the first sequence group bound to each other, a sequence complementary to a sequence selected from those in the second sequence group and a sequence selected from those in the third sequence group bound to each other, a sequence selected from those in the third sequence group and a sequence complementary to a sequence selected from those in the second sequence group bound to each other, a sequence selected from those in the fourth sequence group (Table 4), or a sequence complementary to a sequence selected from those in the fourth sequence group. The complementary sequences include strictly complementary sequences and also sequences that can hybridize under a condition stringent to the sequence groups above. Generally under such a condition, a sequential homology of 90 to 95% seems to be sufficient for progress of the reaction. Such a stringent condition would be obvious for those skilled in the art, and is, for example, a temperature in the range of 20° C. to 65° C., 2×SSC buffer solution, and 0.1% w/v SDS. Particularly favorable is a highly stringent condition at a temperature of at least 65° C., 0.1×SSC buffer solution, and 0.1% w/v SDS. Alternatively, the sequence may be sequences of at least one of the strands of SEQ ID Nos. 1, 2 and 3 or the complementary strands thereof that have one or more nucleotides (e.g., 1 to 5 nucleotides) thereof substituted, deleted, or inserted. However, these substituted, deleted, or inserted sequences are sequences that can hybridize respectively with the complementary strands of unsubstituted, undeleted, or uninserted sequences under the stringent condition. In addition, at least one of SEQ ID Nos. 1, 2 and 3 and the complementary strands thereof may be a mixed-nucleotide sequence of 1 to 5 nucleotides, or at least one of SEQ ID Nos. 1, 2 and 3 and the complementary strands thereof may be a sequence of 1 to 5 nucleotides bring a universal nucleotide. Examples of the universal nucleotides for use include deoxyinosine (dI), and 3-Nitropyrrole, 5-Nitroindole, deoxyribofuranosyl (dP), deoxy-5'-dimethoxytrityl-D-ribofuranosyl (dK) available from Gren Research. It would be obvious for those skilled in the art that these primer regions may be bound to each other directly or via a spacer in the primer according to the invention. A sequence (spacer) of about 1 to 100 nucleotides, preferably 2 to 30 nucleotides, may be present between the sequences or at the terminal of the primer. The length of the nucleic acid primer is about 15 to 200 nucleotides, preferably 20 to 100 nucleotides, and more preferably 40 to 60 nucleotides.

It is possible to amplify the polymorphic region only by using sequences in combination of those in the sequence groups 1 to 3 or in the sequence group 4 as the sequence corresponding to the primer regions F1 and F2, or B1 and B2 in the primer for detection of HPV viral genotype according to the present invention. It is thus possible to detect the polymorphism present in SEQ ID No. 4 contained in LAMP amplification product with the probe. Accordingly, the target sequence FPc, FP, BP, or BPc located in the single-stranded loop of the dumbbell structure of the product amplified with the LAMP primer correspond to the sequence of SEQ ID No. 4.

As described in FIG. 4, it is possible to obtain an HPV-derived target sequence (i.e., sequence in the region corresponding to SEQ ID No. 4) contained in a single-stranded loop structure of a amplification product having a stem-and-loop structure, by amplification by the LAMP method of an HPV-containing sample with the above-mentioned primers in the structure having primer regions F1 and F2.

The amplification reaction may be carried out by using one primer set per tube or multiple primer sets for various genotypes per tube. It is more efficient to use the latter method for identification of multiple genotypes at the same time.

The amplification products are detected, for example, by using probe nucleic acids (FP, FPc, BP, and BPc) having a sequence complementary to the SEQ ID No. 4. Homogeneous hybridization is achieved by using nucleic acid probe labeled by such as fluorochrome (Fluorescein, Rhodamine, FITC, FAM, TET, JOE, VIC, MAX, ROX, HEX, TAMRA, Cy3, Cy5, TexasRed, etc.), quencher (TAMRA, Eclipse, Dabcyl, Au colloid, etc.), electron spin material and metal complex (Ruthenium, Cobalt, Iron, etc.). For example molecular beacon, fluorescence resonance energy transfer (FRET) and electron spin resonance (ESR) technologies are often used for homogeneous hybridization using labeled probe. Invader and pyrosequenching technologies are also used for homogeneous hybridization without labeling. Homogeneous hybridization assay for LAMP products is not particularly limited. The probe nucleic acids may be immobilized on the surface of a solid support for heterogeneous hybridization, and typically, a DNA chip is used, but a probe on another microarray may be used. As described above, the region of the SEQ ID No. 4 is a polymorphic region, and thus, the probe nucleic acids for detection of amplified products may be altered according to the polymorphism to be detected.

The nucleic acid probe sequence for use in the present invention is preferably a nucleic acid probe having a sequence containing a sequence selected from those in the fifth sequence group (Table 5) or a sequence complementary to a sequence selected from those in the fifth sequence group, or the sequence selected from those in the fifth sequence group or the sequence of the complementary to a sequence thereof of which one or more nucleotides are substituted, deleted or insertion. It is also possible to use the sequences described in Kleter et al., J. Clin. Microbiol., 37, 2508-17 (1999); Vernon et al., BMC Infectious Diseases, 3:12 (2003); JP-A 09-509062 (KOKAI) and others. The structure of the nucleic acid probe is also not particularly limited, and DNA, RNA, PNA, LNA, methyl phosphonate-skeleton nucleic acid, and other synthetic nucleic acid chains may also be used. In addition, the chimeric nucleic acids thereof may also be used. It is also possible to introduce a functional group such as amino group, thiol group, or biotin, for immobilization of the nucleic acid probe on a solid support, and a spacer may also be introduced additionally between the functional group and the nucleotide. The kind of the spacer used herein is not particularly limited, and, for example, an alkane or ethylene glycol skeleton may be used. Examples of the universal nucleotides for use in the present invention include deoxyinosine (dI) and 3-Nitropyrrole, 5-Nitroindole, deoxyribofuramsyl (dP), and deoxy-5'-dimethoxytrityl-D-ribofuranosyl (dK) available from Gren Research, and the like.

The detection method for use in the invention is not particularly limited, and examples thereof include optical methods of using turbidity, visible light, fluorescence, chemiluminescence, electrochemiluminescence, chemifluorescence, fluorescent energy transfer, ESR, or the like, and electrical methods of using an electrical property such as electrical current, voltage, frequency, conductivity, or resistance.

The support for immobilizing the nucleic acid probe for use in the invention is not particularly limited, and examples thereof include particles (e.g., resin beads, magnetic beads, metal fine particles, and gold colloid), plates (e.g., microtiter plate, glass plate, silicon plate, resin plate, electrode plate, and membrane), and the like.

The raw material for the support for use in the invention is not particularly limited, and examples thereof include permeable materials such as a porous material and membrane and non-permeable materials such as glass and resin. Typical examples of the support materials include inorganic insulation materials such as glass, quartz glass, alumina, sapphire, forsterite, silicon carbide, silicon oxide, and silicon nitride, and organic materials such as polyethylene, ethylene, polypropylene, polyisobutylene, polymethyl methacrylate, polyethylene terephthalate, unsaturated polyesters, fluorine-containing resins, polyvinyl chloride, polychlorinated vinylidene, polyvinyl acetate, polyvinylalcohol, polyvinyl acetal, acrylic resins, polyacrylonitrile, polystyrene, acetal resins, polycarbonate, polyamide, phenol resins, urea resins, epoxy resins, melamine resins, styrene-acrylonitrile copolymers, acrylonitrile butadiene styrene copolymers, silicone resins, polyphenyleneoxide, polysulfone, polyethylene glycol, agarose, acrylamide, nitrocellulose, nylon, and latex.

The support surface on which the nucleic acid chain is immobilized may be formed, for example, with an electrode material. The electrode material is not particularly limited, but examples thereof include pure metals such as gold, gold alloys, silver, platinum, mercury, nickel, palladium, silicon, germanium, gallium, and tungsten, and the alloys thereof; carbon materials such as graphite and glassy carbon; and the oxides and compounds thereof. Other examples include semiconductor compounds such as silicon oxide, and various semiconductor devices such as CCD, FET, and CMOS. The electrode can be produced by plating, printing, sputtering, vapor deposition, or the like. An electrode film may be formed in vapor deposition by resistance heating, high-frequency heating, or electron beam heating. When in sputtering, the electrode film may be formed by DC bipolar sputtering, bias sputtering, asymmetric AC sputtering, getter sputtering, or high-frequency sputtering. It is also possible to use an electrolytic-polymerization membrane such as polypyrrole or polyaniline or a conductive polymer. The material for insulating the area other than the electrode is not particularly limited, but preferably, a photopolymer or a photoresist material. Examples of the resist materials for use include photoresists for light irradiation, photoresists for far-ultraviolet light, photoresists for X-ray irradiation, and photoresists for electron beam irradiation. Examples of the photoresists for light irradiation include photoresists containing cyclized rubber, polycinnamic acid or novolak resin as the main raw material. A cyclized rubber, a phenol resin, polymethylisopropenylketone (PMIPK), polymethyl methacrylate (PMMA), or the like is used as the far-ultraviolet photoresist. Any one of COP, metal acrylate, as well as the substances described in the Thin Film Handbook (published by Ohmsha) may be used for the X-ray resist. Further, the substances described in the literature above such as PMMA may be used for the electron-beam resist. The resist for use desirably has a thickness of 100 Å or more and 1 mm or less. It is possible to make the area constant by covering the electrode with a photoresist and performing lithography. It is thus possible to uniformize the amount of DNA probe immobilized between electrodes and to make the measurement favorable in reproducibility. The resist material has been generally removed finally, but it is possible to use the resist material as a part of the electrode for gene detection without removal. In such a case, a substance higher in water resistance is needed to be used as the resist material. Materials other than the photoresist materials may be used for the insulation layer formed over the electrode. Examples thereof include oxides, nitrides, and carbides of metals such as Si, Ti, Al, Zn, Pb, Cd, W, Mo, Cr, Ta, and Ni and the alloys thereof. After a thin film is formed on the material, for example, by sputtering, vapor deposition, or CVD, the electrode-exposed regions are patterned to an area adjusted to a particular value by photolithography. It is possible to prepare an electrode allowing tests on several kinds of targets by configuring several electrode units and immobilizing different probes thereon on a single chip. It is also possible to test multiple samples at the same time by configuring several electrode units and immobilizing the same probe thereon on a single chip. In such a case, multiple electrodes are patterned on a substrate previously by photolithography. It is effective then to form an insulation film separating individual electrodes for prevention of contact of neighboring electrodes. The thickness of the insulation film is preferably about 0.1 to 100 micrometers.

The sample to be analyzed in the present invention is not particularly limited, and examples thereof include blood, serum, leukocyte, urine, feces, semen, saliva, vaginal fluid, tissue, biopsy sample, oral mucosa, cultured cell, sputum, and the like. Nucleic acid components are extracted from these samples. The extracting method is not particularly limited, and examples thereof include liquid-liquid extraction, for example with phenol-chloroform, and solid-liquid extraction by using a carrier. Commercial nucleic acid-extracting kits such as QIAamp (manufactured by QIAGEN), or Sumai test (manufactured by Sumitomo Metal Industries) may be used instead. The extracted nucleic acid components are amplified by LAMP methods, and the amplified product is hybridized with the probe immobilized on the electrode for gene detection. The reaction is carried out in a buffer solution at an ionic strength in the range of 0.01 to 5 and at a pH in the range of 5 to 10. Other additives such as hybridization accelerator dextran sulfate, salmon sperm DNA, bovine thymic DNA, EDTA, and surfactant may be added to the solution. The amplified product is added thereto. Alternatively, hybridization may be performed by dropping the solution on the substrate. The reaction may be accelerated, for example, by agitation or shaking during the reaction. The reaction temperature is preferably in the range of 10° C. to 90° C., and the reaction period is about 1 minute or more to overnight. After hybridization reaction, the electrode is separated and washed. A buffer solution at an ionic strength of 0.01 to 5 and a pH in the range of 5 to 10 is used for washing.

The extracted nucleic acid sample can be detected, by labeling with a fluorescent dye such as FITC, Cy3, Cy5, or rhodamine; biotin, hapten, an enzyme such as oxidase or phosphatase, or an electrochemically active substance such as ferrocene or quinone, or by using a second probe previously labeled with the substance described above.

For example with an electrochemically active DNA-binding substance, nucleic acid components are analyzed in the following manner. A substrate is first cleaned, a DNA-binding substance selectively binding to the double-stranded region formed on the electrode surface is allowed to react, and the substrate is analyzed electrochemically. The DNA-binding substance for use is not particularly limited, and examples thereof include Hoechst 33258, acridine orange, quinacrine, daunomycin, metallointercalators, bisintercalators such as bisacridine, trisintercalators, and polyintercalators. In addition, these intercalators may be modified with an electrochemically active metallocomplex such as ferrocene or viologen. The concentration of the DNA-binding substance may vary according to the kind thereof, but is generally in the range of 1 ng/ml to 1 mg/ml. A buffer solution at an ionic strength in the range of 0.001 to 5 and a pH in the range of 5 to 10 is used then. The electrode after reaction with the DNA-binding substance is washed and analyzed electrochemically. The electrochemical measurement is performed in a three-electrode analyzer including reference, counter, and action electrodes or in a two-electrode analyzer including counter and action electrodes. During measurement, a voltage high enough to cause electrochemical reaction of the DNA-binding substance is applied, and the reaction current derived from the DNA-binding substance is determined. The voltage may be varied linearly, or may be applied in the pulse shape or at a constant voltage. The current and voltage during measurement are controlled by using a device such as a potentiostat, a digital multimeter, or a function generator. The concentration of the target gene is calculated from the measured electric current with a calibration curve. The gene-detecting device using the gene-detecting electrode includes a gene-extracting unit, a gene-reacting unit, a DNA-binding substance-reacting unit, an electrochemical measurement unit, a washing unit, and others.

It is possible to diagnose human papilloma virus infection by using the method according to the present invention.

Thus, provided is a method of diagnosing human papilloma viral infection, comprising
obtaining a sample from human;
extracting nucleic acid components from the sample;
a step of amplifying the nucleic acid chains in the sample in LAMP reaction by using multiple primers including at least one primer selected from the nucleic acid primers described above; and
a step of analyzing whether there are amplification products after the amplification reaction, wherein
presence of the amplification products indicates infection to human papilloma virus.

Also provided is a method of diagnosing human papilloma virus infection, comprising
obtaining a sample from human;
extracting nucleic acid components from the sample;
a step of amplifying the nucleic acid chains in the sample in LAMP reaction by using multiple primers including at least one primer selected from the nucleic acid primers described above; and
a step of analyzing whether there are amplification products or identifying the genotype of the virus after the amplification reaction, wherein
presence of the amplification products leads to diagnosis of infection to human papilloma virus.

In addition, the present invention provides a LAMP-amplification kit for use in the detection of human papilloma virus and identification of its genotype. The LAMP-amplification kit contains a nucleic acid primer selected from following (a)-(f) and additionally any other components needed for the LAMP amplification reaction such as polymerase, dNTPs, betaine, buffer, positive control DNA, and sterilized water:

(a) a nucleic acid primer containing, on the same chain, a sequence complementary to a sequence selected from those in a first sequence group listed in Table 1 and a sequence selected from those in a second sequence group listed in Table 2;

(b) a nucleic acid primer containing, on the same chain, a sequence complementary to a sequence selected from those in the first sequence group and a sequence selected from those in a third sequence group listed in Table 3;

(c) a nucleic acid primer containing, on the same chain, a sequence complementary to a sequence selected from those in the second sequence group and a sequence selected from those in the third sequence group;

(d) a nucleic acid primer containing a sequence that differs from a selected sequence of one of the nucleic acid primers (a), (b), and (c), by insertion, deletion, or substitution of one or more bases, and capable to hybridize with a nucleic acid chain having a sequence complementary to the selected sequence of one of the nucleic acid primers (a), (b), and (c);

(e) a nucleic acid primer containing a sequence selected from those in a fourth sequence group listed in Table 4 or a sequence complementary thereto; and (f) a nucleic acid primer containing a sequence that differs from a selected sequence of one of the nucleic acid primers (e), by insertion, deletion, or substitution of one or more bases, and capable to hybridize with a nucleic acid chain having a sequence complementary to the selected sequence of one of the nucleic acid primers (e).

In addition, the present invention provides a detection kit for use in the detection of human papilloma virus and identification of its genotype. The detection kit includes the above-mentioned LAMP-amplification kit and a support carrying a nucleic acid chain immobilized thereon for detection of the human-papilloma-virus LAMP amplification products amplified by using the LAMP-amplification kit. The immobilized nucleic acid chain is;

(g) a nucleic acid probe containing a sequence selected from those in a fifth sequence group listed in Table 5 or a sequence complementary thereto, or (h) a nucleic acid probe containing a sequence that differs from a selected sequence of one of the nucleic acid probe (g), by insertion, deletion, or substitution of one or more bases, and capable to hybridize with a nucleic acid chain having a sequence complementary to the selected sequence of one of the nucleic acid probe (g). The nucleic acid probe may be immobilized on the surface of a support, and the support and the support surface are made of the material described above.

EXAMPLES

Hereinafter, typical examples of the sequences corresponding to the primer regions in the first, second, third, and fourth sequence groups are shown in the following Tables.

TABLE 1

Representative nucleic acid primer sequence

| Sequence group | SEQ ID No. | Sequence (5' → 3') |
|---|---|---|
| First sequence group | 16 | TGATTTACAGTTTATTTTTC |
| | 17 | GAATATGATTTACAGTTTATTTTTC |
| | 18 | GAAGAATATGATTTACAGTTTATTTTTC |
| | 19 | GAGGAATATGATTTACAGTTTATTTTTC |
| | 20 | GAGTATGATTTACAATTTATTTTTC |
| | 21 | GAGTTTGATTTACAGTTTATTTTTC |
| | 22 | GAATTTGATTTACAATTTATTTTTC |
| | 23 | GAATATGATTTACAGTTTATTTTTC |
| | 24 | GAATATGATTTGCAGTTTATTTTTC |
| | 25 | GAATATGAATTACAGTTTGTGTTTC |
| | 26 | GAATTTGATTTACAATTTATATTTC |
| | 27 | GAATATGATATACAGTTTATATTTC |
| | 28 | GAATATGATCTACAGTTTGTTTTTC |
| | 29 | GAGTATGACCTGCAGTTTGTGTTTC |
| | 30 | GAATATGATTTACAGTTTATTTTTC |
| | 31 | GACTATGATTTACAATTTATATTTC |
| | 32 | GAGTTTGATTTGCAGTTTATTTTTC |
| | 33 | GAATATGATGTGCAATTTATATTTC |
| | 34 | GAATATGATTTACAGTTTATTTTTC |
| | 35 | GAGTATGAATTGCAATTTATTTTTC |
| | 36 | GAATTTGATTTACAATTTATTTTTC |
| | 37 | GAATATCAATTACAATTTGTGTTTC |
| | 38 | GAATATGAATTACAATTTGTTTTTC |
| | 39 | GAATATGACTTACAGTTTGTTTTTC |
| | 40 | GAGTTTGATTTGCAATTTATTTTTC |
| | 41 | GAATATGAACTACAGTTTGTGTTTC |
| | 42 | GAATATCATTTGCAATTTATATTTC |
| | 43 | GAAAHATAAAYTGYAADTCATAYTC |

TABLE 2

| Sequence group | SEQ ID No. | Sequence (5' → 3') |
|---|---|---|
| Second sequence group | 44 | TTTGTTACTGTGGTAGATAC |
| | 45 | TTTGTTACTGTGGTAGATACTAC |
| | 46 | TTTGTTACTGTGGTAGATACCAC |
| | 47 | TTTCTTACTGTGGTAGATACCAC |
| | 48 | TTTGTTACTGTAGTTGATACTAC |
| | 49 | TTTGTTACTGTTGTTGATACTAC |
| | 50 | TTTGTTACTGTGGTAGATACCAC |
| | 51 | TTTGTTACTGTTGTGGACACCAC |
| | 52 | TTTGTTACTGTGGTAGATACCAC |
| | 53 | TTTCTAACTGTTGTCGATACTAC |
| | 54 | TTTGTTACTGTGGTAGATACCAC |
| | 55 | TTTTTAACTGTTGTAGATACTAC |
| | 56 | TTTGTTACTGTAGTTGATACAAC |
| | 57 | TTTCTTACTGTTGTGGACACTAC |
| | 58 | TTTGTTACAGTTGTAGACACCAC |
| | 59 | TTTTTAACTGTGGTTGATACTAC |
| | 60 | TTTGTTACTGTAGTGGACACTAC |
| | 61 | TTTATTACCTGTGTTGATACTAC |
| | 62 | TTTGTCACAGTTGTGGATACCAC |
| | 63 | TTTGTAACTGTTGTGGATACCAC |
| | 64 | TTTGTTACTGTAGTAGATACTAC |
| | 65 | TTTGTTACTGTGGTTGATACOAC |
| | 66 | TTTGTAACCGTTGTGGATACCAC |
| | 67 | TTTGTTACTGTTGTGGATACTAC |
| | 68 | TTTCTTACTGTTGTGGATACCAC |
| | 69 | TTTKTTACHGTKGTDGATACYAC |

TABLE 3

| Sequence group | SEQ ID No. | Sequence (5' → 3') |
|---|---|---|
| Third sequence group | 70 | GCACAGGGCCACAATAATGG |
| | 71 | CCACAGGGACATAACAATGG |
| | 72 | GCGCAGGGCCACAATAATGG |
| | 73 | GCACAGGGACATAATAATGG |
| | 74 | GCCCAGGGCCACAACAATGG |
| | 75 | GCTCAGGGTTTAAACAATGG |
| | 76 | GCTCAGGGTTTAAACAATGG |
| | 77 | GCCCAGGGACATAACAATGG |
| | 78 | GCTCAGGGACATAACAATGG |

TABLE 3-continued

| Sequence group | SEQ ID No. | Sequence (5' → 3') |
|---|---|---|
| | 79 | GCCCAGGGACACAATAATGG |
| | 80 | GCACAGGGTCATAACAATGG |
| | 81 | GCACACGGTCATAATAATGG |
| | 82 | GCACAGGGACACAATAATGG |
| | 83 | GCTCAGGGACACAATAATGG |
| | 84 | GCACAAGGTCATAATAATGG |
| | 85 | GCCCAGGGACAAAACAATGG |
| | 86 | GCACAAGGCCATAATAATGG |
| | 87 | GCCCAGGGCCACAACAATGG |
| | 88 | GCCCAGGGCCATAACAATGG |
| | 89 | GCACAAGGACACAATAATGG |
| | 90 | GCACATAATAATGG |
| | 91 | GCGCAGGGCCACAATAATGG |
| | 92 | GCCCAGGGCCATAACAATGG |
| | 93 | GCGCAGGGTCACAATAATGG |
| | 94 | GCGCAGGGCCACAATAATGG |
| | 95 | GCCCAGGGACATAATAATGG |
| | 96 | GCCCAGGGTCAAAACAATGG |
| | 97 | GCGCAGGGTCACAATAATGG |
| | 98 | GCCCAAGGCCATAATAATGG |
| | 99 | GCACAAGGTCATAACAATGG |
| | 100 | GCTCAGGGTTTAAACAATGG |
| | 101 | CCCCAGGGCCACAACAATGG |
| | 102 | GCACAGGGTCATAATAATGG |
| | 103 | GCACAGGGACATAACAATGG |
| | 104 | GCACAGGGTCATAATAATGG |
| | 105 | GCCCAGCGCCATAATAATGG |
| | 106 | GCACAGGGACACAACAATGG |
| | 107 | GCACAGGGACATAACAATGG |
| | 108 | GCCCAGGGAACTAATAATGG |
| | 109 | GCCCAGGGTCATAATAATGG |
| | 110 | GCACAGGGTCATAATAATGG |
| | 111 | GCGCAAGGCCACAATAATGG |
| | 112 | GCACAGGGACATAATAATGG |
| | 113 | GCCCAGGGACATAATAATGG |
| | 114 | GCGCGGGGTCATAACAATGG |
| | 115 | GCMCAGGGWCATAAYAATGG |
| | 103 | GCACAGGGACATAACAATGG |
| | 104 | GCACAGGGTCATAATAATGG |
| | 105 | GCCCAGGGACATAACAATGG |
| | 106 | GCACAGGGACACAATAATGG |
| | 107 | GCACAGGGACATAACAATGC |

TABLE 4

| Sequence group | SEQ ID No. | Sequence (5' → 3') |
|---|---|---|
| Fourth sequence group | 116 | CCGTCTAGTATCAACAACAGT |
| | 117 | CCTTATTGGTTACAACGAGCACAACAAATAGTTGGTTACCCCA |
| | 118 | GGTGAAAATGTACCAGACGAT |
| | 119 | AGAGGTAACCATAGAACCACTAGGGTCTACTGCAAATTTAGCCA |
| | 120 | AGTAGATATGGCAGCACAT |
| | 121 | ACAGGGCCACAATAATGGCATGACATATTTGTACTGCGTTT |
| | 122 | CATTAAAGGCTCTGGGTCTA |
| | 123 | GCATCAGAGGTAACCATAGAACCACTGCAAATTTAGCCAGTTCA |
| | 124 | TTCCAGTCCTCCAAAATAGTGG |
| | 125 | ATACTACACGCACTACAAATATGTCTGTCATAACGTCTGCAGTTAAGG |
| | 126 | CAAATTATTTTCCTACACCTAGTGG |
| | 127 | GTTGGTTACCCCAACAAATGCCTCTATGGTTACCTCTGATGCCC |
| | 128 | GTCATAACGTCTGCAGTTAAGG |
| | 129 | GTCGTAGGTACTCCTTAAAGTTAG |
| | 130 | ATACTACACGCAGTACAAATATGTCTCCCCATGTCGTAGGTACTCC |
| | 131 | CTACACGCAGTACAAATATGTCTCCCCATGTCGTAGGTACTCC |
| | 132 | CACGCAGTACAAATATGTCACCCATGTCGTAGGTACTCC |
| | 133 | CTACACGCAGTACAAATATGTCGTAGTTTCTGAAGTAGATATGGCA |
| | 134 | CTACACGCAGTACAAATATGTCTATGTAGTTTCTGAAGTAGATATG |
| | 135 | GTGGCCCTGTGCTCGTTGTTCTATGGTTACCTCTGATGCCC |
| | 136 | GTGGCCCTGTGCTCGTTGTCTATGGTTACCTCTGATGCC |
| | 137 | GTGCTGCCATATCTACTTCAGAAAC |
| | 138 | GCTGCCATATCTACTTCAGAAACTACA |
| | 139 | AACCAATAAGGTTTATTGAATATTT |
| | 140 | CCAATAAGGTTTATTGAATATTTGG |
| | 141 | TTATGCAGCAAATGCAGGTGTGGCCCCTATAGGTGGTTTGCAACC |
| | 142 | CCCTATAGGTGGTTTGCAAC |
| | 143 | GTACATGGGATCCTTTGCC |

TABLE 4-continued

| Sequence group | SEQ ID No. | Sequence (5' → 3') |
|---|---|---|
| | 144 | ACAGAAAATGCTAGTGCTTATGCAGCCAATTGTGTTTGTTTGTAATCCATAG |
| | 145 | CACAGAAAATGCTAGTGCTTATTGTGTTTGTTTGTAATCCATAG |
| | 146 | ATAAAGGATGGCCACTAATGCCCGTGTAGGTGTTGAGGTAGGTCG |
| | 147 | CCTGACACCTCATTTTATAATCCAG |
| | 148 | ATCCAGATACACAGCGGCTG |
| | 149 | CCACACCTAATGGCTGACCACACACAGCGGCTGGTTTG |
| | 150 | GCCACTAATGCCCACACCTAATGACACAGCGGCTGGTTTG |
| | 151 | CCAACAGTACCAGCCCTAT |
| | 152 | TGGTGTCAGAACCATATGGCGACAAACATTTGTTCCCTTCG |
| | 153 | CACAGTTATTCAGGATGGTGAT |
| | 154 | GGAACTTCACTTTTGTTAGCCTGTTGGTTCATACTGGCTTTGG |
| | 155 | CCCTATAGGTGGTTTGCAAC |
| | 156 | ACAGAAAATGCTAGTGCTTATGCAGCCAATTGTGTTTGTTTGTAATCCATAG |
| | 157 | CCTGACACCTCATTTTATAATCCAG |
| | 158 | CCACACCTAATGGCTGACCACACACAGCGGCTGGTTTG |
| | 159 | GCCACTAATGCCCACACCTAATGACACAGCGGCTGGTTTG |
| | 160 | AAGTTCCAATCCTCTAAAATACTGC |
| | 161 | ACCACTCGCAGTACCAATTTAACTGAATATAGGACATAACATCTGCAG |
| | 162 | TGTATTCTCCCTCTCCAAGTG |
| | 163 | TAATTGATTATGCCAGCAAACACCCTCTATTGTTACCTCTGACTCCC |
| | 164 | GCCAGCAAACACCATTGTTACTCTATTGTTACCTCTGACTCCC |
| | 165 | GCCAGCAAACACCATTGTTATGCTCTATTGTTACCTCTGACTCCC |
| | 166 | GAATATAGGACATAACATCTGCAG |
| | 167 | ACCACTCGCAGTACCAATTTAACCCTCAACATGTCTGCTATACTGC |
| | 168 | CCACTCGCAGTACCAATTTAACCCTCAACATGTCTGCTATACTGC |
| | 169 | CCACTCGCAGTACCAATTTAACCTCAACATCTCTGCTATACTG |
| | 170 | ACCCTGTGCCTTATGTAACC |
| | 171 | GATGACACTGAAAGTTCCCATGCGCCCAAAATACATAACTGTGTCTGC |
| | 172 | GATGACACTGAAAGTTCCCATGCGCCAAAATACATAACTGTGTCTGC |
| | 173 | AGTGTTCCCCAATAGCAGG |
| | 174 | CAGTGTTCCCCAATAGCAGG |
| | 175 | GACACTGAAAGTTCCCATGCCGCTGTGTCTGCTTATAATCTACAGACAC |
| | 176 | TAAAATGGATGCCCACTAAGGCCTGCTGGAGTGGAAATTGGCCG |
| | 177 | CCTGAAACACAACGTTTAGTG |
| | 178 | CACAACGTTTAGTGTGGGCC |
| | 179 | ACCTGATACTAGTATTTATAATCCTGA |
| | 180 | GATGCCCACTAAGGCCAACACGCCTGTGCTGGAGTGGA |
| | 181 | CACTAAGGCCAACACCTAAAGGCAACACAACGTTTAGTGTGGG |
| | 182 | AGTGTTCCCCAATAGCAGG |
| | 183 | GACACTGAAAGTTCCCATGCCGCTGTGTCTGCTTATAATCTACAGACAC |
| | 184 | CCTGAAACACAACGTTTAGTG |
| | 185 | ACCTGATACTAGTATTTATAATCCTGA |
| | 186 | GATGCCCACTAAGGCCAACACGCCTGTGCTGGAGTGGA |
| | 187 | CACTAAGGCCAACACCTAAAGGCAACACAACGTTTAGTGTGGG |
| | 188 | CCAATCTTCCAAAATAGCAGGATTC |
| | 189 | ACCACACGTAGTACCAATATGTCCTGTGAATATATGTCATTATGTCTGCAG |
| | 190 | CATACTTTCCTACACCTAGCG |
| | 191 | AACTGATTGCCCCAACAAATACCCTCCATGGTTACTTCAGATGCAC |
| | 192 | CCATTATTGTGTCCCTGAGCACCTCCATGGTTACTTCAGATGCAC |
| | 193 | CTGATTGCCCCAACAAATACCTCCATGGTTACTTCAGATGC |
| | 194 | CTGATTGCCCCAACAAATACCCATGGTTACTTCAGATGCAC |
| | 195 | GTGAATATATGTCATTATGTCTGCAG |
| | 196 | ACCACACGTAGTACCAATATGTCTTCCTCACCATGTCTTAAATACTC |
| | 197 | ACCACACGTAGTACCAATATGTCATTCCTCACCATGTCTTAAATACTC |
| | 198 | CACACGTAGTACCAATATGTCTGATTCCTCACCATGTCTTAAATACTC |
| | 199 | CCACACGTAGTACCAATATGTCCCTCACCATGTCTTAAATACTC |
| | 200 | CCACACGTAGTACCAATATGTCCTCACCATGTCTTAAATACTC |
| | 201 | CACGTTGCATCCAATATGGT |
| | 202 | CACGTTGCATCCAATATGG |
| | 203 | CACTGAAAACTCTAATAGATATGCCGGTGCAACCAAGTAAACACAGTTGTG |
| | 204 | CCAATAGGTGGTTTGCAAC |
| | 205 | CCTTTACCCCAATGCTCTCC |
| | 206 | CACTGAAAACTCTAATAGATATGCCGGAGTTGTGTTTGTTTATAATCCATTG |
| | 207 | CTGAAAACTCTAATAGATATGCCTGTGTTTGTTTATAATCCATTG |
| | 208 | GGATGACCACTAATACCTACACCCTGTGTTGGTTTAGAGGTAGGTC |
| | 209 | TCCTGATACATCTTTTTATAATCCTG |
| | 210 | AACTCAACGCTTAGTTTGGGC |
| | 211 | CCACTAATACCTACACCTAATGGCTGCAAACTCAACGCTTAGTTTGGGC |
| | 212 | CACTAATACCTACACCTAATGGCCTCAACGCTTAGTTTGGG |
| | 213 | GACCTACCTCTAAACCAACACAG |
| | 214 | TAATGGCTGCCCGCGA |
| | 215 | CCAATAGGTGGTTTGCAAC |
| | 216 | CACTGAAAACTCTAATAGATATGCCGGAGTTGTGTTTGTTTATAATCCATTG |
| | 217 | TCCTGATACATCTTTTTATAATCCTG |
| | 218 | CCACTAATACCTACACCTAATGGCTGCAAACTCAACGCTTAGTTTGGGC |
| | 219 | GGAGGTGTTAAACCAAATTGCC |
| | 220 | ACCACTCGCAGTACTAATATGACTATGTCATAACTTCTGCAGTTAAGG |
| | 221 | ACCACTCGCAGTACTAATATGACCTTCTGCAGTTAAGGTAACTTTGC |

TABLE 4-continued

| Sequence group | SEQ ID No. | Sequence (5' → 3') |
|---|---|---|
| | 222 | GCTTTTTTTCCCACTCCTAGTG |
| | 223 | CCTGATTGCCCCAACAAATACCGATCAATGGTTACTTCCGAATCTC |
| | 224 | CCTGATTGCCCCAACAAATACCAGCCATATTGGCTACAACGTGC |
| | 225 | ATGTCATAACTTCTGCAGTTAAGG |
| | 226 | ACCACTCGCAGTACTAATATGACTTCTTCAACATGTCTTATATATTC |
| | 227 | ATACCACTCGCAGTACTAATATGTTCTTCAACATGTCTTATATATTC |
| | 228 | ACCACTCGCAGTACTAATATGACATTCTTCAACATGTCTTATATATTCT |
| | 229 | ATACCACTCGCAGTACTAATATGATTCTTCAACATGTCTTATATATTCT |
| | 230 | CCTGGACAACCGGGTGCTGTTGGAGGCTTACATCCAAG |
| | 231 | TATCCTGGACAACCGGGTGCTCCTGTTGGAGGCTTACATCCAAG |
| | 232 | GGAGGCTTACATCCAAGTAAAC |
| | 233 | GTACAAGCAACACCTTTACCCC |
| | 234 | GACACTGAAACCGGTAACAAGTATCCACTCTGTTTGTTTATAATCCATGG |
| | 235 | GGATGACCACTTATGCCAACGCCACAACGATTAGTATGGGCATGTG |
| | 236 | CCTGACACCTCCTTTTATAACCCT |
| | 237 | CCTGACACCTCCTTTTATAACCC |
| | 238 | CACTTATGCCAACGCCTAATGGGATACAACGATTAGTATGGGC |
| | 239 | GGATGACCACTTATGCCAACGCACAACGATTAGTATGGGCATG |
| | 240 | GCTGCCCTCTACCTATTTCAAGG |
| | 241 | CACCTTTACCCCAATGTTCC |
| | 242 | GTCATATTAGTACTGCGAGTGG |
| | 243 | CCGGGTGCTGATAATAGGGACCTGTTGGAGGCTTACATCC |
| | 244 | CCATATTGGCTACAACGTGCTACCTGATTGCCCCAACA |
| | 245 | CCATATTGGCTACAACGTGCACCAAATACCTGATTGCCCC |
| | 246 | GTGCACAAGGTCATAATAATGG |
| | 247 | AGTATGGGCATGTGTAGGC |
| | 248 | AGGGCTGGTACATTAGGAGA |
| | 249 | TGTTCCCCATGACCTGTAC |
| | 250 | CTTGTTACCGGTTTCAGTGTCAGCAGCCATTAGGCGTTG |
| | 251 | GCACTCCTTTGAATAGAGGCACTGTTCCCGATGACCTG |
| | 252 | GTAACCATTGATCCACTAGGAGTGAAAGGTTCAGGAACTACTGCC |
| | 253 | GTAGTTCCTGAACCTTTAATGTACAG |
| | 254 | GCACTGCTTTGAATAGAGGCA |
| | 255 | CAGTAGTTCCTCAACCTTTAATGTACA |
| | 256 | GGAGGCTTACATCCAAGTAAAC |
| | 257 | GACACTGAAACCGGTAACAAGTATCCACTGTGTTTGTTTATAATCCATGG |
| | 258 | CCTGACACCTCCTTTTATAACCCT |
| | 259 | CACTTATGCCAACGCCTAATGGGATACAACGATTAGTATGGGC |
| | 260 | CAAATCCTGTGTCTACCATG |
| | 261 | GGCACACCTTGTAATGCTAACTCCCCGTCTTGTAGTACAGTG |
| | 262 | ATGTTGGTAACTCTGGTAACTC |
| | 263 | GGAGGCCTACAACCTATTAAACAGGTACAGATAACAGGGAATGC |
| | 264 | AATTGTGTTTGTTTATAATCCATAG |
| | 265 | TGCACCAAATCCTGTGTC |
| | 266 | GCTAACCAGGTAAAAGCAGGATACCATGTCCCCGTCTTG |
| | 267 | AACTCTGGTAACTCTGGTACAG |
| | 268 | GGAGGCCTACAACCTATTAAACAACAGGGAATGCATTTCTATGG |
| | 269 | CAATTGTGTTTGTTTATAATCCATAG |
| | 270 | GATATTTGCAAATGGAACTG |
| | 271 | GACGGGGACATGGTAGACACATATATCTAGGGGAACATCAC |
| | 272 | GTGTTTAATAGGTTGTAGGCC |
| | 273 | CTCCTGCTTTTACCTGGTTAGCTCCTATAGGTGAACATTGGG |
| | 274 | ATTACAAGGTGTGCCTTTTC |
| | 275 | GGATATTTGCAAATGGAACTG |
| | 276 | GGGACATGGTAGACACAGGACATATATCTAGGGGAACATCAC |
| | 277 | CCTATAGGTGAACATTGGG |
| | 278 | GTTTAGTAACTCCAAAGGAGGACAAAGGCACACCTTGTAATGC |
| | 279 | ATTCTCCTGCTTTTACCTGG |
| | 280 | CATTCTCCTGCTTTTACCTGGT |
| | 281 | ATCCTCTAAAATGGACGGGTTC |
| | 282 | CAACCCGTAGTACAAATATGTCTGATATGTCATAACATCTGCTGTTAGTG |
| | 283 | CTAGTTATTTTCCTACTCCTAGTGG |
| | 284 | CAATTGGTTACTCCAACAAATACCCTCTATGGTAACCTCCGATGCAC |
| | 285 | CCATTATTATGGCCTTGTGCACGCTCTATGGTAACCTCCGATGCAC |
| | 286 | ATGGCCTTGTGCACGTTGCAACCTCTATGGTAACCTCCGATGCAC |
| | 287 | GGCCTTGTGCACGTTGCCTATGGTAACCTCCGATGCAC |
| | 288 | GCCTTGTGCACGTTGCACTATGGTAACCTCCGATGCAC |
| | 289 | ATGTCATAACATCTGCTGTTAGTG |
| | 290 | ATGTCATAACATCTGCTGTTAGTG |
| | 291 | CAACCCGTAGTACAAATATGTCTGTTCTTCACCATGCCTTAAATATTCC |
| | 292 | CCCGTAGTACAAATATGTCTGCACCATGCCTTAAATATTCC |
| | 293 | CCCGTAGTACAAATATGTCTGTTCACCATGCCTTAAATATTCC |
| | 294 | CCCGTAGTACAAATATGTCTGCTTCACCATGCCTTAAATATTCC |
| | 295 | CCAATATGGTTTATTAAATATTTG |
| | 296 | CAATATGGTTTATTAAATATTTGTG |
| | 297 | CAATATGGTTTATTAAATATTTGTGC |
| | 298 | GTTGGTAACTCTGGTAACTCTGGGGAGGCCTACAACCTATTAAACAC |
| | 299 | GTTGGTAACTCTGGTAACTCTGGGAGGCCTACAACCTATTAAACAC |

TABLE 4-continued

| Sequence group | SEQ ID No. | Sequence (5' → 3') |
|---|---|---|
| | 300 | CCCAATGTTCACCTATAGGAGG |
| | 301 | GCCTTTTCCCCAATGTTCACC |
| | 302 | TGGTAACTCTGGTAACTCTGGTACAGCCTACAACCTATTAAACACAATTGTG |
| | 303 | GGATGACCACTAATACCTACTCCGTTTGGTTTGGGCCTGTACAGG |
| | 304 | GGATGACCACTAATACCTACTCCGTTTGGTTTGGGCCTGTACAG |
| | 305 | CCAGACACATCATTTTATGATCC |
| | 306 | TTATGATCCCTGCCTCCAGC |
| | 307 | GACCACTAATACCTACTCCTAATGGCCTGCCTCCAGCGTTTGG |
| | 308 | AGCATTACAAGGTGTGCC |
| | 309 | CAGATAACAGGGAATGCATTTCAATGTTCACCTATAGGAGGCC |
| | 310 | AAGTAGGTCGTGGTCAGC |
| | 311 | CCAGAGTTACCAGAGTTACCAACGGAGTAGGTATTAGTGGTCATCC |
| | 312 | GATTTTCAGTATCATCCAATTTAT |
| | 313 | CCCAATGTTCACCTATAGGAGG |
| | 314 | TGGTAACTCTGGTAACTCTGGTACAGCCTACAACCTATTAAACACAATTGTG |
| | 315 | CCAGACACATCATTTTATGATCC |
| | 316 | GACCACTAATACCTACTCCTAATGGCCTGCCTCCAGCGTTTGG |
| | 317 | CCAATTGTCCAATATAGAGGAATTC |
| | 318 | ACTACCCGTAGTACCAACTTTACGACATAACATCAGTTGTTAATGTGAC |
| | 319 | GTTCTGTATACTGCCCCTCTC |
| | 320 | AACATATACCATTGTTGTGGCCCTTCCATGGTAACCTCTGATTCCC |
| | 321 | GCCTTATGTAGCCAATAAGGCCCAGCGGTTCCATGGTAACC |
| | 322 | GCCTTATGTAGCCAATAAGGCGCGGTTCCATGGTAACCTCTG |
| | 323 | GCCAACATATACCATTGTTGTCATGGTAACCTCTGATTCCC |
| | 324 | GACATAACATCAGTTGTTAATGTGAC |
| | 325 | ACTACCCGTAGTACCAACTTTACTCCACGTGCCTGGTATATTCC |
| | 326 | ACTACCCGTAGTACCAACTTTACTCCACGTGCCTGGTATATTCCT |
| | 327 | CTACCCGTAGTACCAACTTTACCCACCTGCCTGGTATATTCC |
| | 328 | CCTTATGTAGCCAATAAGGC |
| | 329 | GGCCTTATGTAGCCAATAAGGC |
| | 330 | CAGTAGGGATAATGTGTCTGTGGATGCCTTTCCCTTACCCCAGTG |
| | 331 | AATGGCGGGAACACAGC |
| | 332 | CCGTAGATACATTATTGGGCTTGC |
| | 333 | CTGAAAACTCACCATTTTCATCAACCCACAACTGTGTCTGTTTATAATCCAC |
| | 334 | GGTGAGTTTTCAGTATCATCCTCTCCCATTGGGTGTTGGTATTAGTGG |
| | 335 | CCAGATGCATCCTTATATAATCCA |
| | 336 | GTTTAGTATGGGCTTGTGTAGG |
| | 337 | ATGGGTGTCCACTAATACCAACACGTTTAGTATGGGCTTGTGTAGGG |
| | 338 | AATGGCGGGAACACAGC |
| | 339 | CTGAAAACTCACCATTTTCATCAACCCACAACTGTGTCTGTTTATAATCCAC |
| | 340 | CCAGATGCATCCTTATATAATCCA |
| | 341 | ATGGGTGTCCACTAATACCAACACGTTTAGTATGGGCTTGTGTAGGG |
| | 342 | TGGTGGAGGGACACCAAAATTC |
| | 343 | TTCCAATTTTCTAATATACTACTATTC |
| | 344 | CACTACCCGCAGTACTAATTTAACATATGACATAACCTCTGCAGTTAAAG |
| | 345 | CACTACCCGCAGTACTAATTTAACGGATATATGACATAACCTCTGCAG |
| | 346 | CACTACCCGCACTACTAATTTAACCCTCTGCAGTTAAAGTAATAGTGC |
| | 347 | CACTACCCGCAGTACTAATTTAACCTATGGATATATGACATAACCTCTGC |
| | 348 | TGTATTCCCTTCTCCCAG |
| | 349 | GTGAAACCCTGGCAGTTG |
| | 350 | AAATACCATTGTTATGGCCCTGGGGCTCTATTATTACTTCTGATTCTC |
| | 351 | ATACCATTCTTATGGCCCTGGGTCTGTATTCCCCTTCTCCCAC |
| | 352 | ATACCATTGTTATGGCCCTGGGTGTATTCCCCTTCTCCCAGTG |
| | 353 | ATACCATTGTTATGGCCCTGGGGGCTCTATTATTACTTCTGATTCTC |
| | 354 | CAACTGATTATGCCAACAAATACCAGCCATATTGGTTACATAAGGCC |
| | 355 | TATCACATAACCTCTGCAGTTAAAG |
| | 356 | CACTACCCGCAGTACTAATTTAACCCTCCACATGTCTACTATACTGC |
| | 357 | CACTACCCGCAGTACTAATTTAACACTATACTGCTTAAACTTAGTAGGG |
| | 358 | GGATGATACAGAAAGTGCTCATGCCCTAAAATACACAGCTGTGTTTGC |
| | 359 | GGATGATACAGAAAGTGCTCAAAATACACAGCTGTGTTTGC |
| | 360 | CACCAATAGCAGGTACACAACC |
| | 361 | GTGCTCACCAATAGCAGGTAC |
| | 362 | GGATGATACAGAAAGTGCTCATGCAGCTGTTTGCTTATAATCAACTGACACA |
| | 363 | TAAAATGGATGGCCACTTAGGCCGGTATGGAAATTGGTCGTGGGC |
| | 364 | CCACTTAGGCCAATACCTAAGTGTAGGTATGGAAATTGGTCG |
| | 365 | CCTGAAACACAACGTTTGGTT |
| | 366 | GAAACACAACGTTTGGTTTGGGC |
| | 367 | GCCACTTAGGCCAATACCTAAAGGCATGTGTAGGTATGGAAATTGG |
| | 368 | GCCACTTAGGCCAATACCTAAAGTGGGCATGTGTAGGTATGGAA |
| | 369 | AGGCTGCCCACGACC |
| | 370 | CAATACCTAAAGGCTGCC |
| | 371 | CACCAATAGCAGGTACACAACC |
| | 372 | GGATGATACAGAAAGTGCTCATGCAGCTGTTTGCTTATAATCAACTGACACA |
| | 373 | CCTGAAACACAACGTTTGGTT |
| | 374 | GCCACTTAGGCCAATACCTAAAGGCATGTGTAGGTATGGAAATTGG |
| | 375 | GCCACTTAGGCCAATACCTAAAGTGGGCATGTGTAGGTATGGAA |
| | 376 | CTGTTCAAGAATGGTAGGATCC |
| | 377 | TCCACTGTTCAAGAATGGTAGG |

TABLE 4-continued

| Sequence group | SEQ ID No. | Sequence (5' → 3') |
|---|---|---|
| | 378 | TAACTATTAGCACTGCCACTGCATAAGCCATTACCTCTGTAGTTAAAG |
| | 379 | TAACTATTAGCACTGCCACTGCGTGTCTAAATAAGCCATTACCTCTG |
| | 380 | ATATACTCTGCTACTCCCAGTG |
| | 381 | GGCCGTGACCCTATAGAAAG |
| | 382 | GCTGATTGTTCCAGCAAATGCCGGTCTATGATAACATCTGATTCTC |
| | 383 | ATTATTGTGACCCTGCGCACGGATACTCTGCTACTCCCAGTGGG |
| | 384 | TAAGCCATTACCTCTGTAGTTAAAG |
| | 385 | TAACTATTAGCACTGCCACTGCCTTCCCCATGCCTAATATATTGC |
| | 386 | ATACTACCAGAAGTACAAATTTAACCTTCCCCATGCCTAATATATTGC |
| | 387 | GCACAACAAGATGTTAGAGATAACACCCAATAGGTGGAGCACAGCCT |
| | 388 | TTGCATGTAGTGCCAATACCC |
| | 389 | GCATGTAGTGCCAATACCCC |
| | 390 | TGCACAACAAGATGTTAGAGATAACACAATAGGTGGAGCACAGCCT |
| | 391 | GCACAACAAGATGTTAGAGATAACAATAGGTGGAGCACAGCC |
| | 392 | GCACAACAAGATGTTAGAGATAAATAGGTGGAGCACAGCC |
| | 393 | GCACAACAAGATCTTAGAGATCAATAGGTGGAGCACAGCC |
| | 394 | TGCTATGCGTGAATTTTCTGTGTCTTGGTGTTGGCCTTAGTGGTCA |
| | 395 | GTTGAGGTGGGCAGAGGAC |
| | 396 | CCAGACACAGATAGGTTGGTG |
| | 397 | CTATGCGTGAATTTTCTGTGTCATCCCTTGGTGTTGGCCTTAGT |
| | 398 | CTATGCGTGAATTTTCTGTGCCCTTGGTGTTGGCCTTAG |
| | 399 | GCTATGCGTGAATTTTCTGTGCCCTTGGTGTTGGCCTTAG |
| | 400 | CATCATATTTATTAAATAAGGGATG |
| | 401 | TTTATTAAATAAGGGATGACCA |
| | 402 | CATATTTATTAAATAAGGGATGACCAC |
| | 403 | TTGCATGTAGTGCCAATACCC |
| | 404 | TGCACAACAAGATGTTAGAGATAACACAATAGGTGGAGCACAGCCT |
| | 405 | GTTGAGGTGGGCAGAGGAC |
| | 406 | CTATGCGTGAATTTTCTGTGTCATCCCTTGGTGTTGGCCTTAGT |
| | 407 | CCTCAGCACATAAAGTCATG |
| | 408 | GTACTGGTTACAACGTGCGCA GTGGTATCCACAACTGTGAC |
| | 409 | GGGTCTAACTCTGGCAAT |
| | 410 | GGATTCTGAGGTTACCATAGAACC ACTGCCACTGTACAAAGC |
| | 411 | CCTCAGCACATAAAGTCATG |
| | 412 | CAGGGCCACAATAATGGCAT ACGAGTGGTATCCACAAC |
| | 413 | GGGTCTAACTCTGGCAAT |
| | 414 | GGATTCTGAGGTTACCATAGAACCACTGCCACTGTACAAAGC |
| | 415 | GTCCTCTAAAATAGTGGCATCC |
| | 416 | GGGGTAAGGCCAAATTGCC |
| | 417 | CCACTCGTAGCACTAACATGACGTATGTCATAACATCAGCTGTTAATG |
| | 418 | CCACTCGTAGCACTAACATGACCCTCTAAAATAGTGGCATCCATC |
| | 419 | GCTTTTTTTCCTACTCCTAGTGG |
| | 420 | GCCACTGTACAAAGCAGTGC |
| | 421 | ACTGATTGCCCCAACATATGCCTTCTATGGTAACCTCAGAATCCC |
| | 422 | ATTATTGTGGCCCTGCGCACGTTCTATGGTAACCTCAGAATCCC |
| | 423 | CCCTGCGCACGTTGTAACTATGGTAACCTCAGAATCCC |
| | 424 | CCAACATATGCCATTATTGTGCTATGGTAACCTCAGAATCCC |
| | 425 | ACCACTCGTAGCACTAACATGACTCGCCATGACGAAGGTATTCCT |
| | 426 | CCACTCGTAGCACTAACATGGCCATGACGAAGGTATTCC |
| | 427 | CCACTCGTAGCACTAACATGACGCCATCACGAAGGTATTCC |
| | 428 | GTATGTCATAACATCAGCTGTTAATG |
| | 429 | TGAATGTATGTCATAACATCAGCTG |
| | 430 | CCACTCGTAGCACTAACATGACTCGCCATGACGAAGGTATTCC |
| | 431 | GCTGAGGTTAAAAAGGAAAGCACA |
| | 432 | GACTTTATGTGCTGAGGTTAAAAAGG |
| | 433 | CTTTATGTGCTGAGGTTAAAAAGGAAAG |
| | 434 | CCAGTACGGTTTATTAAATAATT |
| | 435 | GCGCACGTTGTAACCAGTAC |
| | 436 | GTTGTAACCAGTACGGTTTATTAAATA |
| | 437 | CGTTGTAACCAGTACGGTTTATTAAAT |
| | 438 | CACCTATAGGAGGTTTGCATCC |
| | 439 | TGATACTGAAACCAGTAACAAATATGCTAACTGAGTCTGCTTATAATCCATAG |
| | 440 | CCAGATACATCTTTTTATAACCCAG |
| | 441 | AAAGGATGCCCACTAATACCCACAAAACCCAAAGGTTGGTGTG |
| | 442 | CCTCAGCACATAAAGTCATG |
| | 443 | CAGGGCCACAATAATGGCAT AGTGGTATCCACAACTGTGA |
| | 444 | GCCACTGTACAAAGCAGT |
| | 445 | CACGTTGTAACCAGTACGGTTTTTCCTACTCCTAGTGGTTCT |
| | 446 | CACCTATAGGAGGTTTGCATCC |
| | 447 | TGATACTGAAACCAGTAACAAATATGCTAACTGAGTCTGCTTATAATCCATAG |
| | 448 | CCAGATACATCTTTTTATAACCCAG |
| | 449 | AAAGGATGCCCACTAATACCCACAAAACCCAAAGGTTGGTGTG |
| | 450 | GTCCTCCAGTAGGTTAGCATTC |
| | 451 | AGTACTAACATGACTATTAGTACTGCTGCCATAACCTCTGCAGACAAAG |
| | 452 | ATACTACTAGAAGTACTAACATGACTGCCATAACCTCTGCAGACAAAG |
| | 453 | GTATATGTTGCTACGCCTAGTG |
| | 454 | AATTGATTACCCCAGCAAATGCCGTCTATGATTACGTCTGAGGCAC |
| | 455 | CCCCAGCAAATGCCATTATTCTATGATTACGTCTGAGGCAC |

TABLE 4-continued

| Sequence group | SEQ ID No. | Sequence (5' → 3') |
|---|---|---|
| | 456 | GCCATAACCTCTGCAGACAAAG |
| | 457 | ATACTACTAGAAGTACTAACATGACCCTCCACATGTCTAAGGTACTG |
| | 458 | GCACGTTGCAACCAATAAGG |
| | 459 | GGCTGGATGATACTGAAACTTCCCACAACTGTGTTTGCTTGCCATC |
| | 460 | TCCAATGTTCACCCATAGC |
| | 461 | CCAATGTTCACCCATAGCGG |
| | 462 | GGATGATACTGAAAGTTCCAATTTAGCCACAAGTGTGTTTGCTTGCC |
| | 463 | AAACAATGGATGGCCACTTAGCCATGTGTAGGTTTGGAGGTAGGC |
| | 464 | TTATAATCCGGACCAGGAACG |
| | 465 | ATAATCCGGACCAGGAACGG |
| | 466 | ACAATGGATGGCCACTTAGCC GCATGTGTAGGTTTGGAGGTAGG |
| | 467 | GGATGATACTGAAAGTTCCAATTTAGCCACAACTGTGTTTGCTTGCC |
| | 468 | TTATAATCCGGACCAGGAACG |
| | 469 | ACAATGGATCGCCACTTACCCGCATGTGTAGGTTTCGACCTAGG |
| | 470 | TCCAATGTTCACCCATAGC |
| | 471 | CAAAGTCCATGCATCCAAAC |
| | 472 | GCCTGTAACAATAATGCAGCTGCACCATGTCACCATCCTCA |
| | 473 | AACAGATATCCCGCACAG |
| | 474 | GTGGGAGGTTTACAGCCAATTAGGTCTGATAACAGGGAATGC |
| | 475 | CCATTGTTATGACCTTGTGC |
| | 476 | TCCAACTCCTAGTGGCTCTATAGCGCTGTAGCCAATAAGGC |
| | 477 | GACGTGAGCAGATGTTTGT |
| | 478 | GGATAACTGCAGTATTACCGGACCTAGGGCTGGAAAACTTGG |
| | 479 | GTTACCTCAGAATCACAATTATTTAATAAGCC |
| | 480 | CCTCAGAATCACAATTATTTAATAAGCC |
| | 481 | CAGTCCTCCAAAATATTGGAATCC |
| | 482 | AACCAAATTGCCAGTCCTCC |
| | 483 | TACCACTCGTAGCACTAATATGACATATGTCATTATCTCTGCAGTTAGTG |
| | 484 | ACCACTCGTAGCACTAATATGACTATCTCATTATCTCTGCAGTTACTG |
| | 485 | ACCACTCGTAGCACTAATATGACATATGTCATTATCTCTGCAGTTAGTC |
| | 486 | ACCACTCGTAGCACTAATATGACAGTTAGTGTAATTTTGCAAAGCTG |
| | 487 | TACCACTCGTAGCACTAATATGACGCAGTTAGTGTAATTTTGCAAAGCTG |
| | 488 | GTAGTGCATTTTTTCCAACTCCTAG |
| | 489 | CTGCAGTTATCCAAAGTAGTGC |
| | 490 | CTGATTGCCCCAGCAAATGCCGCTCTATAGTTACCTCAGAATCAC |
| | 491 | CTGATTGCCCCAGCAAATGCCTTGGCTACAGCGTGCACAACG |
| | 492 | CTGATTGCCCCAGCAAATGCCGGCTCTATAGTTACCTCAGAATCA |
| | 493 | ATGTCATTATCTCTGCAGTTAGTG |
| | 494 | ACCACTCGTAGCACTAATATGACTTCTTCAACATGACGTACATATTCC |
| | 495 | CTCACCAGTGGGAGGTTTAC |
| | 496 | CTGAAACCAGTAACAGATATCCCGGCCAATTAAACATAATTGTGTTTG |
| | 497 | TGAAACCAGTAACAGATATCCCGTCCATAGATAAGCATTCCCTG |
| | 498 | TGAAACCAGTAACAGATATCCCGAATCCATAGATAAGCATTCCC |
| | 499 | TAACCCTGATACACAACGTTTG |
| | 500 | AGGATGACCACTTACGCCAACACTCTGGGCATGTGTAGGCCTT |
| | 501 | CAATGGCTGTCCCCTACCTA |
| | 502 | ATGGCTGTCCCCTACCTATTTC |
| | 503 | CCTTTACCCCAATGCTCAC |
| | 504 | AGCCAGGGTCTGATAACAGGGGGAGGTTTACAGCCAATT |
| | 505 | AATAGCTAGGGGACAGCC |
| | 506 | GCGGGATATCTGTTACTGGTTTCAGCGTAAGTGGTCATCCTT |
| | 507 | CTCACCAGTGGGAGGTTTAC |
| | 508 | CTGAAACCAGTAACAGATATCCCGGCCAATTAAACATAATTGTGTTTG |
| | 509 | TAACCCTGATACACAACGTTTG |
| | 510 | AGGATGACCACTTACGCCAACACTCTGGGCATGTGTAGGCCTT |
| | 511 | CCAATCCTCCAAAATAGTGGTATTC |
| | 512 | CTACTCGCAGCACCAATCTTTCGTATGACATTACCTCTGTAGTTAATG |
| | 513 | CTACTCGCAGCACCAATCTTTCGAATGTATGACATTACCTCTGTAG |
| | 514 | CTACTCGCAGCACCAATCTTTCTGAATGTATGACATTACCTCTGTAG |
| | 515 | ACAATTGATTGTGCCAACATATACCGGTCTGTGGTTACTTCTGATTCAC |
| | 516 | TATATTCCCCTTCCCCAAGTG |
| | 517 | CAATTGATTGTGCCAACATATACCGGTCTGTGGTTACTTCTGATTCAC |
| | 518 | TTAAACCCTGAGCCTTGTGCAGGGTCTGTGGTTACTTCTGATTCAC |
| | 519 | GTATGACATTACCTCTGTAGTTAATG |
| | 520 | GAATGTATGACATTACCTCTGTAG |
| | 521 | TGAATGTATGACATTACCTCTGTAG |
| | 522 | CTACTCGCAGCACCAATCTTTCCCTCCACATGTCTGGCATATTC |
| | 523 | GCAGGTACACAGCCAATAATACAC |
| | 524 | GATGA CACTGAAAACTCTCATGTAGCGCTGAGTTTGTTTATAATCCACAG |
| | 525 | GATGACACTGAAAACTCTCATGCTGAGTTTGTTTATAATCCACAG |
| | 526 | CCAGATAACACAGTATATGATCCTAAC |
| | 527 | CACTGAGTCCTACCCCTAAAGGTTGTCTCAACGCTTGGTCTGG |
| | 528 | CACTGAGTCCTACCCCTAAAGGTCTCAACGCTTGGTCTGG |
| | 529 | GCTGTTGATACCAAAGATACACGTG |
| | 530 | CTGTTGATACCAAAGATACACGTGATA |
| | 531 | GATACCAAAGATACACGTGATAATG |
| | 532 | GCATCTGCTGTTGATACCAAAGATAC |
| | 533 | GATTTCAACACCTACACAGGC |

TABLE 4-continued

| Sequence group | SEQ ID No. | Sequence (5' → 3') |
|---|---|---|
| | 534 | GCAGGTACACAGCCAATAATACAC |
| | 535 | GATGA CACTGAAAAC TCTCATGTAG CGCTGAGTTTGTTTATAATCCACAG |
| | 536 | CCAGATAACACAGTATATGATCCTAAC |
| | 537 | CACTGAGTCCTACCCCTAAAGGTTGTCTCAACGCTTGGTCTGG |
| | 538 | GTGCCTTGTGCAGCCAAT |
| | 539 | CTAGTTATGTATATGCCCCCTCGCCGCTTGTTAAATAACTGGCAGTCTGA |
| | 540 | ACGTAGGGAACAGTTATTTGCTAG |
| | 541 | TGTCACGTATGTCAGTGCCCTTAATGGAATAGAGGGGGCATGGT |
| | 542 | AATGGCAGGAACACAGCC |
| | 543 | TGAAAATTCCCCGTTTTCCTCCAACGCGTTTGTTTATAGTCCACTGAAAC |
| | 544 | TGATACGCAGCGATTGGTATG |
| | 545 | TGCCCACTAAGGCCAACACCGGCCTCTGTTGGTGTTGAA |
| | 546 | GTTAAATAACTGGGAGTCTGAGGAT |
| | 547 | TAAGGGCACTGACATACGTGACAGCCATAGACCCACTAGGCGAG |
| | 548 | CTGCAGATGTATATGGAGACAGTA |
| | 549 | AGTGTCCCTACCATGCCCCACGTAGGGAACAGTTATTTGCT |
| | 550 | TGTGTCCCTGTGCCTTGT |
| | 551 | GTAGTTATGTATATGCCCCCTCGCCGCAGCCAATAGGGCTTGTT |
| | 552 | CGCAGTACCAATTTTACTTTGTCTACTACCTCAACATGCCTAATATATTCC |
| | 553 | ACTGACATACGTCACAGTCCTAG |
| | 554 | GATTATGCCAACAAATACCATTGTTGTTCCCAGTTATTTAACAAGCCC |
| | 555 | CAGTAAGAAATAATTGATTATGCCAACAAACAAGCCCTATTGGCTGC |
| | 556 | CCACTCGCAGTACCAATTTTACTTTGCCTCAACATGCCTAATATATTCC |
| | 557 | ATACCACTCGCAGTACCAATTTTACCCTCAACATGCCTAATATATTCC |
| | 558 | TCAGTGGACAATGTTATAGTACAC |
| | 559 | CCACTCGCAGTACAAATTTTACTTTGCCTCAACATGCCTAATATATTCC |
| | 560 | ATACCACTCGCAGTACAAATTTTACCCTCAACATGCCTAATATATTCC |
| | 561 | CATCAGTGGATAATGTTATAGTACAC |
| | 562 | GCGCAGTACTAATTTTACATTGTCCCCTCAACATGCCTAACATATTCC |
| | 563 | ATACAACGCGCACTACTAATTTTACCCTCAACATGCCTAACATATTCC |
| | 564 | GATTTACCTTTGGCCCAGTG |
| | 565 | TAGATGATACTGAAAATTCCCCGTTGCCTATAATACATAGTTGCGTTTG |
| | 566 | CCTGAGTCTACATTATATAACCCTGA |
| | 567 | CCCACTAAGGCCAACACCTAATGTACGCAGCGATTGGTATGG |
| | 568 | CAGCTGATTCAGTAGTAGTAGACAA |
| | 569 | GGCACAGGGACACAACAATGGTAAATTGGTACTGCGAGTGGTA |
| | 570 | TGACATACGTGACAGTCCTAGT |
| | 571 | TTGTGCAGCCAATAGGGCTTGTTAAGTATATGCCCCCTCGCCTA |
| | 572 | CTCTATTCCAAAAATGCCTAGCA |
| | 573 | CCTAGTAGTTATGTATATGCCCCCTC |
| | 574 | TACAATTCAGTAGGTATAGTGTCCCCT |
| | 575 | GTGGGTCTATGGTATCCTCAGACTC |
| | 576 | CCACTCGCAGTACCAATTTTACTTTGCATCAGTGGACAATGTTATACTACAC |
| | 577 | TACCACTCGCAGTACCAATTTTACCATCAGTGGACAATGTTATAGTACAC |
| | 578 | CCATTGTTGTGTCCCTGTGCCTCTATGGTATCCTCAGACTCCC |
| | 579 | CAACAAATACCATTGTTGTGTCCCTCTATGGTATCCTCAGACTCCC |
| | 580 | CCTCCAACAAAAATCCTAAGGACAGCCAATGGCAGGAACACAGCC |
| | 581 | CTCCAACAAAAATCCTAAGGACAGCCAATGGCAGGAACACAGCCT |
| | 582 | GATTTACCTTTGGCCCAGTGC |
| | 583 | TATAATGGATGCCCACTAAGGCCGCCTGTGTTGCTGTTGAAATAGG |
| | 584 | ACCCTGATACGCAGCGATTG |
| | 585 | GTTATGTATATGCCCCCTCG |
| | 586 | CAACGCGCAGTACTAATTTTACATTGCATCAGTGGATAATGTTATAGTACAC |
| | 587 | TACAACGCGCAGTACTAATTTTACCATCAGTGGATAATGTTATAGTACAC |
| | 588 | GTTATGTGTATGCCCCCTCG |
| | 589 | CAACAAATACCATTGTTGTGTCCCTCTATGGTGTCCTCTGACTCCC |
| | 590 | CCAATCATCCAAAATAGCAGGATTC |
| | 591 | TAGATGATACTGAAAATTCCCCGTTGCCTATAATACATAGTTGCGTTTG |
| | 592 | CCTGAGTCTACATTATATAACCCTGA |
| | 593 | CCCACTAAGGCCAACACCTAATGTACGCAGCGATTGGTATGG |
| | 594 | GATTTACCTTTGGCCCAGTG |

In addition, typical examples of the sequences in the fifth sequence group corresponding to the nucleic acid probe will be shown below.

TABLE 5

| Sequence group | SEQ ID No. | Sequence (5'→°3') |
|---|---|---|
| Fifth sequence group | 595 | ATTATGTGCTGCCATATCTACTTCAGAAACTAC |
| | 596 | AACCAATAAGGTTTATTGAATATTTGGGCATC |
| | 597 | ACCAATAAGGTTTATTGAATATTTGGGCATCAGA |
| | 598 | CAATAAGGTTTATTGAATATTTGGGCATCAG |
| | 599 | ATAAGGTTTATTGAATATTTGGGCATCACAG |

TABLE 5-continued

| Sequence group | SEQ ID No. | Sequence (5'→3') |
|---|---|---|
| | 600 | AAGGTTTATTGAATATTTGGGCATCAGAGG |
| | 601 | AAATGCAGGTGTCGATAATAGAGAATGTAT |
| | 602 | AAATGCAGGTGTGGATAATAGAGAATGTA |
| | 603 | ATTATGTGCTGCCATATCTACTTCAGAAAC |
| | 604 | GTGCTGCCATATCTACTTCAGAAACTACAT |
| | 605 | TATGTGCTGCCATATCTACTTCAGAAACTACATA |
| | 606 | ACTTCAGAAACTACATATAAAAATACTAACTTTAA |
| | 607 | TTATGTGCTGCCATATCTACTTCAGAAACT |
| | 608 | CTACTTCAGAAACTACATATAAAAATACTAACTT |
| | 609 | TCAGAAACTACATATAAAAATACTAACTTTAAGGAG |
| | 610 | AACTACATATAAAAATACTAACTTTAAGGAGTACCTA |
| | 611 | ATGTGCTGCCATATCTACTTCAGAAACTACATATAAAA |
| | 612 | TGCCATATCTACTTCAGAAACTACATATAAAAATACT |
| | 613 | TCTACACAGTCTCCTGTACCTGGGCAATATG |
| | 614 | AATATGTGCTTCTACACAGTCTCCTGTACCT |
| | 615 | CTCCTCTACGTGGGCAATATGATGCTACCAA |
| | 616 | CACGTCTAATGTTTCTGAGGACGTTAGGGA |
| | 617 | GTCTAATGTTTCTGAGGACGTTAGGGA |
| | 618 | TAATGTTTCTGAGGACGTTAGGGA |
| | 619 | TAATGTTTCTGAGGACGTTAGGGACAATGTG |
| | 620 | TAATGTTTCTGAGGACGTTAGGGACAATG |
| | 621 | AATGTTTCTGAGGACGTTAGCGACAATGTG |
| | 622 | AATATGTCCTTCTACACAGTCTCCTCTACC |
| | 623 | TGCTTCTACACAGTCTCCTGTACCTGGGCA |
| | 624 | TGCTTCTACACAGTCTCCTGTACCTGGGCA |
| | 625 | ACCTGGGCAATATGATGCTACCAAATTTAA |
| | 626 | CCTGTACCTGGGCAATATGATGCTACCAAATTTAA |
| | 627 | TGGTCCTGGCACTGATAATAGGGAATGTATATCAATGG |
| | 628 | ATAATAGGGAATGTATATCAATGGATTATAAACAAACAC |
| | 629 | GGCACTGATAATAGGGAATGTATATCAATGGATTATAAA |
| | 630 | TGGTCCTGGCACTGATAATAGGGAATGTAT |
| | 631 | ATAATAGGGAATGTATATCAATGGATTATAAA |
| | 632 | ATAATAGGGAATGTATATCAATGGATTATAAAC |
| | 633 | ATAATAGCGAATGTATATCAATGGATTATAAACAAAC |
| | 634 | TGCTGCAATTGCAAACAGTCATACTACATT |
| | 635 | AACAGTGATACTACATTTAAAAGTAGTAATTTTAA |
| | 636 | TTATCCATCGATTATAAACAAACACAGTTATGTTT |
| | 637 | TTATCCATGGATTATAAACAAACACAGTTATGTTTAC |
| | 638 | TTATCCATGGATTATAAACAAACACAGTTATGTTTACTTGGA |
| | 639 | ACAAGGTCATAATAATGGTATTTGTTGGGG |
| | 640 | GTAGTTCCTGAACCTTTAATGTACAGGTCA |
| | 641 | CAAGGTCATAATAATGGTATTTGTTGGGGC |
| | 642 | ATGTTTATCCATGGATTATAAACAAACACAGTTAT |
| | 643 | TTATCCATGGATTATAAACAAACACAGTTA |
| | 644 | TTATCCATGGATTATAAACAAACACAGTTATGT |
| | 645 | TGGACAACCGGGTGCTGATAATAGGGAATG |
| | 646 | TGGACAACCGGGTGCTGATAATA |
| | 647 | GATAATAGGGAATGTTTATCCATGGATTATAAACAA |
| | 648 | AGGGAATGTTTATCCATGGATTATAAACAAACAC |
| | 649 | AGGGAATGTTTATCCATGGATTATAAACAA |
| | 650 | AATGTTTATCCATGGATTATAAACAAACACAGT |
| | 651 | ACTTTATGCACACAAGTAACTAGTGACAGT |
| | 652 | ACTAGTGACAGTACATATAAAAATGAAAATTTTAA |
| | 653 | ATGGATTTTACTACATTACAAGCTAATAAAA |
| | 654 | TTTGGTGCAATGGATTTTACTACATTACAAGCTA |
| | 655 | GTGCAATGGATTTTACTACATTACAAGCTAATA |
| | 656 | ATAACAGGGAATGCATTTCTATGGATTAT |
| | 657 | TTCTGCTGTCTCTTCTAGTGACAGTACATA |
| | 658 | TCTAGTGACAGTACATATAAAAATGACAATTTTAA |
| | 659 | TCTATAGAGTCTTCCATACCTTCTACATATGATCCT |
| | 660 | TGGGCCTTATGTAGCCAATAAGGCTTATTAAATAACTG |
| | 661 | GCCAATAAGGCTTATTAAATAACTGGGAATCAGAG |
| | 662 | CAATAAGGCTTATTAAATAACTGGGAATCA |
| | 663 | AATAAGGCTTATTAAATAACTGGGAATCAGA |
| | 664 | TCTTCCATACCTTCTACATATGATCCTTCTAA |
| | 665 | TCCATACCTTCTACATATGATCCTTCTAAGTTTAAGGAAT |
| | 666 | TTATCTACCTCTATAGAGTCTTCCATACCTTCTACA |
| | 667 | ATACCTTCTACATATGATCCTTCTAAGTTTAAG |
| | 668 | TTCTACATATGATCCTTCTAAGTTTAAGGAATATACC |
| | 669 | TATGTAGCCAATAAGGCTTATTAAATAACTGGGA |
| | 670 | ACCAATAAGGACAGTAGGGATAATGTGTCT |
| | 671 | ACCAATAAGGACAGTAGGGATAATGTGT |
| | 672 | ACCAATAAGGACAGTAGGGATAATGTG |
| | 673 | CCTCTATAGAGTCTTCCATACCTTCTACAT |
| | 674 | TCCATACCTTCTACATATGATCCTTCTAAGTTTAA |
| | 675 | GTTATTACGCAGGATGTTAGGGATAATGTG |
| | 676 | AGCTACACGCTGTTATTACGCAGGATCTTAGG |
| | 677 | ACGCACGATCTTAGGGATAATGTCTCAGTTGAT |

TABLE 5-continued

| Sequence group | SEQ ID No. | Sequence (5'→°3') |
|---|---|---|
| | 678 | CTACAGCTGTTATTACGCAGGATGTTAGGGATAATGTGTC |
| | 679 | ACAGCTGTTATTACGCAGGATGTTAGGGAT |
| | 680 | TGTTATTACGCAGGATGTTAGGGATAATGT |
| | 681 | TTACGCAGGATGTTAGGGATAATCTGTCAG |
| | 682 | TACACAAAATCCTGTGCCAAGTACATATGA |
| | 683 | CCTGTGCCAAGTACATATGACCCTACTAAGTTTAA |
| | 684 | GACAACAAACAGACTCAGTTATGTATAATAGGCTGTGC |
| | 685 | TCATCATATTTATTAAATAAGGGATGACCACT |
| | 686 | ACATCTGTTGACAACAAACAGACTCAGTTATGTA |
| | 687 | ATCATATTTATTAAATAAGGGATGACCACTAAGG |
| | 688 | TGTTGACAACAAACAGACTCAGTTATGTATAAT |
| | 689 | TATTTATTAAATAAGGGATGACCACTAAGGCCA |
| | 690 | TTGACAACAAACAGACTCAGTTATGTATAATAGGCT |
| | 691 | GCGGTTTCCCCAACATTTACTCCAAGTAACTTT |
| | 692 | TCCCCAACATTTACTCCAAGTAACTTTAAGC |
| | 693 | AAACAGACTCAGTTATGTATAATAGGCTGTG |
| | 694 | CAGACTCAGTTATGTATAATAGGCTGTGCT |
| | 695 | TCTGTTGACAACAAACAGACTCAGTTATGTATAATAGG |
| | 696 | TCTGTTGACAACAAACAGACTCAGTTATGTATAAT |
| | 697 | GTTGACAACAAACAGACTCAGTTATGTATAATAGG |
| | 698 | TGTTGACAACAAACAGACTCAGTTATGTATAATAGG |
| | 699 | TCTGTTGACAACAAACAGACTCAGTTATGTATAATAGGCT |
| | 700 | GCTGCGGTTTCCCCAACATTTACTCCAAGT |
| | 701 | GCGGTTTCCCCAACATTTACTCCAAGTAAC |
| | 702 | GCGGTTTCCCCAACATTTACTCCAAGTAACTTTAA |
| | 703 | TAATGGCATATGTTGGGGCAATCAGTTGTTTGTCACAG |
| | 704 | ACTAGGAGTAGGAAAAAAAGCACTGCTTTG |
| | 705 | GGGCCACAATAATGGCATATGTTGGGCAATCAGTTGTT |
| | 706 | TATGTTGGGGCAATCAGTTGTTTGTCACAGTT |
| | 707 | TAGGAGTAGGAAAAAAAGCACTGCTTTGTA |
| | 708 | CACAATAATGGCATATGTTGGGGCAATCACT |
| | 709 | ACAATAATGGCATATGTTGGGGCAATCAGTTGTTTGT |
| | 710 | TACGGTTTATTAAATAATTGGGATTCTGAG |
| | 711 | GAGGTTAAAAAGGAAAGCACATATAAAAATGAAAATTTTA |
| | 712 | TTTATGTGCTGAGGTTAAAAAGGAAAGCACA |
| | 713 | TTGTAACCAGTACGGTTTATTAAATAATTGGGA |
| | 714 | GTTAAAAAGGAAAGCACATATAAAAATGAAAT |
| | 715 | TAAAAAGGAAAGCACATATAAAAATGAAAATTTTAAGGAA |
| | 716 | GGAAAGCACATATAAAAATGAAAATTTTAAGGAATACCTT |
| | 717 | TGTAACCAGTACGGTTTATTAAATAATTGGGATTCTGA |
| | 718 | TGTGCTGAGGTTAAAAAGGAAAGCACATATAAAAATGAAA |
| | 719 | CCAGTACGGTTTATTAAATAATTGGGATTC |
| | 720 | CTGAGGTTAAAAAGGAAAGCACATATAAAA |
| | 721 | TTAAAAAGGAAAGCACATATAAAAATGAAAAT |
| | 722 | CTGAGGTTAAAAAGGAAAGCACATATAAAAT |
| | 723 | TGCTGAGGTTAAAAAGGAAAGCACATATAAA |
| | 724 | AAAAAGGAAAGCACATATAAAAATGAAAATTTTAAGGA |
| | 725 | TGCTGAGGTTAAAAAGGAAAGCACATATAAAAA |
| | 726 | TGCTGAGGTTAAAAAGGAAAGCACATATAAAAAT |
| | 727 | TTTATGTGCTGAGGTTAAAAAGGAAAGCACATATAAAAATGAAAA |
| | 728 | TTTATGTGCTGAGGTTAAAAAGGAAAGCACATATAAAAAT |
| | 729 | TTTATGTGCTGAGGTTAAAAAGGAAAGCACATATA |
| | 730 | GGTAAACCTGGTATAGATAATAGGGAATGT |
| | 731 | TGGTAAACCTGGTATAGATAATAGGGAATGT |
| | 732 | TTTATGTGCTGAGGTTAAAAAGGAAAGCAC |
| | 733 | CCTTGGGCACGTTGCAACCAATAAGGTTTATTAAATACT |
| | 734 | TTAGTACTGCTACAGAACAGTTAAGTAAATATGATGCACG |
| | 735 | GGCACGTTGCAACCAATAAGGTTTATTAAATAACTGTGCC |
| | 736 | CGTTGCAACCAATAAGGTTTATTAAATAACTGTGCCTC |
| | 737 | GCTACAGAACAGTTAAGTAAATATGATGCACGAAAAT |
| | 738 | TTATTATGGCCTTGGGCACGTTGCAACCAATAAGGTTT |
| | 739 | ACAGAACAGTTAAGTAAATATGATGCACGAAAA |
| | 740 | ACCAATAAGGTTTATTAAATAACTGTGCCTCAGAC |
| | 741 | AGAACAGTTAAGTAAATATGATGCACGAAAAATTAATCAG |
| | 742 | TAACATGACTATTAGTACTGCTACAGAACAGTTAAGTAAA |
| | 743 | GTAAATATGATGCACGAAAAATTAATCAGTACCTTAG |
| | 744 | TGACTATTAGTACTGCTACAGAACAGTTAAGTAAATATGA |
| | 745 | GAACAGTTAAGTAAATATGATGCACGAAAAA |
| | 746 | TACTGCTACAGAACAGTTAAGTAAATATGATGCACG |
| | 747 | AATAATAATGTTATAGAAGATACTAGGGAC |
| | 748 | ATAGTAGGGACAATATATCAGTTGATGGCA |
| | 749 | TATTAGTACTGCTACAGAACAGTTAAGTAA |
| | 750 | ACAGAACAGTTAAGTAAATATGATGCACGA |
| | 751 | GAACAGTTAAGTAAATATGATGCACGAAAAATTAA |
| | 752 | AGGTCATCCGGGACAGCCTCGCCAAGTTTT |
| | 753 | TTACCTCAGAATCACAATTATTTAATAAGCCT |
| | 754 | CTTTAATATAAAGGTCATCCGGGACAGCCTCG |
| | 755 | CAGAATCACAATTATTTAATAAGCCTTATT |

TABLE 5-continued

| Sequence group | SEQ ID No. | Sequence (5'→3') |
|---|---|---|
| | 756 | CCAATGGCTGTCCCCTACCTATTTCAAGGC |
| | 757 | CACAGCCAGGGTCTGATAACAGGGAATGCTT |
| | 758 | TGGCTGTCCCCTACCTATTTCAAGGCCTAC |
| | 759 | GGGTCTGATAACAGGGAATGCTTATCTATG |
| | 760 | CACAGCCAGGGTCTGATAACAGGGAATGCT |
| | 761 | CAGGGAATGCTTATCTATGGATTATAAACA |
| | 762 | CACTGAAGTAACTAAGGAAGGTACATATAA |
| | 763 | ATTATGCACTGAAGTAACTAAGGAAGGTAC |
| | 764 | ACTAAGGAAGGTACATATAAAAATGATAATTTTAA |
| | 765 | TGATACCAAAGATACACGTCATAATGTATCTG |
| | 766 | ATCTGCTGTTGATACCAAAGATACACGTGA |
| | 767 | GCCCCGACCGATTTCAACACCTACACAGGC |
| | 768 | GCCCCGACCGATTTCAACACCTACACAGGCCCAGACCAA |
| | 769 | ACCAAAGATACACGTGATAATCTATCTGTGGATTATA |
| | 770 | CCCGACCGATTTCAACACCTACACAGGCCCAGAC |
| | 771 | CTGTTCATACCAAAGATACACGTGATAATG |
| | 772 | GTTGATACCAAAGATACACGTGATAATGTATCTGTGGA |
| | 773 | CGATTTCAACACCTACACAGGCCCAGACCA |
| | 774 | ATCTGCTGTTGATACCAAAGATACACGTGA |
| | 775 | CTGCTGTTGATACCAAAGATACACGTGA |
| | 776 | TCTGCTGTTGATACCAAAGATACACGTGAT |
| | 777 | ATCTGCTGTTGATACCAAAGATACACGTGATAATG |
| | 778 | GTTGATACCAAAGATACACGTGATAATGTATCTGTGG |
| | 779 | TCTGCTGTTGATACCAAAGATACACGTGATAATGTATCTG |
| | 780 | TCTATTCCTAATGTATACACACCTACCAGT |
| | 781 | TCTATTCCTAATGTATACACACCTACCAGTTTTAA |
| | 782 | TCCTAGTAGTTATGTATATGCCCCCTCGCCT |
| | 783 | AGTAGTTATGTATATGCCCCCTCGCCTAGT |
| | 784 | AGTAGTTATGTGTATGCCCCCTCGCCTAGC |
| | 785 | TGAATCAGCTGTACCAAATATTTATGATCCT |
| | 786 | AGACTCTACTGTACCAGCTGTGTATGATTCT |
| | 787 | TTCCTCCAACAAAAATCCTAAGGACAGTAG |
| | 788 | TTCCTCCAACAAAAATCCTAAGGACAGTA |
| | 789 | TCCTAAGGACAGTAGGGAATATGTTTCAGT |
| | 790 | TCAGTGGACTATAAACAAACGCAACTATG |
| | 791 | TCCACTACTACAGACTCTACTGTACCAGCT |
| | 792 | GCTGTACCAAATATTTATGATCCTAATAAATTTAA |
| | 793 | TTTGTCTACTACTACTGAATCAGCTGTACCAAA |
| | 794 | ACTGTACCAGCTGTGTATGATTCTAATAAATTTAA |

Hereinafter, the method of detecting a nucleic acid according to the present invention will be described specifically with reference to Examples.

(1) Synthetic Oligonucleotide

A nucleic acid primer for use in the detection of human papilloma virus and identification of its genotype is prepared in combination of the sequences described in Table 1 above. More specifically, sequences in the first and the second sequence groups, sequences in the first and third sequence groups, or sequences complementary to the sequences in the second sequence groups and sequences in third sequence groups are bound to each other directly or via a spacer. Alternatively, a sequence in the fourth sequence group or a sequence complementary thereto is prepared. Any method known to those skilled in the art may be used in preparing the primers.

(2) LAMP Reaction Solution

The LAMP reaction solution had the composition shown in the following Table 6. The template used was a plasmid DNA containing cloned HPV16.

TABLE 6

| Reagent | Volume |
|---|---|
| Sterilized ultrapure water | 1.5 μL |
| Bst DNA polymerase | 1 μL |
| Buffer | 12.5 μL |
| Tris HCl(pH8.0) | 40 mM |

TABLE 6-continued

| Reagent | Volume |
|---|---|
| KCl | 20 mM |
| MgSO4 | 16 mM |
| (NH4)2SO4 | 20 mM |
| Tween20 | 0.2% |
| Betaine | 1.6 M |
| dNTP | 2.8 mM |
| F3-primer(10 μM) | 0.5 μL |
| B3-primer(10 μM) | 0.5 μL |
| FIP-primer(10 μM) | 4 μL |
| BIP-primer(10 μM) | 4 μL |
| Template (cloned HPV16) | 1 μL |
| Total | 25 μL |

In addition, the nucleic acid primer for LAMP amplification reaction shown in the following Table 7 was used as the same time.

TABLE 7

Nucleic acid primer sequence for LAMP amplification

| Title | SEQ ID No. | Sequence (5' → 3') |
|---|---|---|
| FIP primer | 12 | GAAAAATAAACTGTAAATCATATTCTTTGTTACTGTGGTAGATACTAC |

TABLE 7-continued

Nucleic acid primer sequence
for LAMP amplification

| Title | SEQ ID No. | Sequence (5' → 3') |
|---|---|---|
| F3 primer | 13 | GCACAGGGCCACAATAATGG |
| BIP primer | 14 | TTTTTGGGAAGTAAATTTAAAGGACGTCCTAAAGGAAACTGATC |
| B3 primer | 15 | CCTGCTTGTAGTAAAAATTT |

(3) Nucleic Acid Amplification by Lamp Method

The nucleic acid amplification is carried out at a temperature of 58° C. for 1 hour. A sample added with sterilized water instead of the template is used as the negative control. Analysis of the amplified LAMP products by agarose gel electrophoresis reveals a ladder-shaped pattern characteristic to LAMP products. On the other hand, no amplification is observed with a sample containing no template DNA. It is thus possible to perform sequence-specific amplification of the papilloma virus by using a selected primer set.

Figure 5:
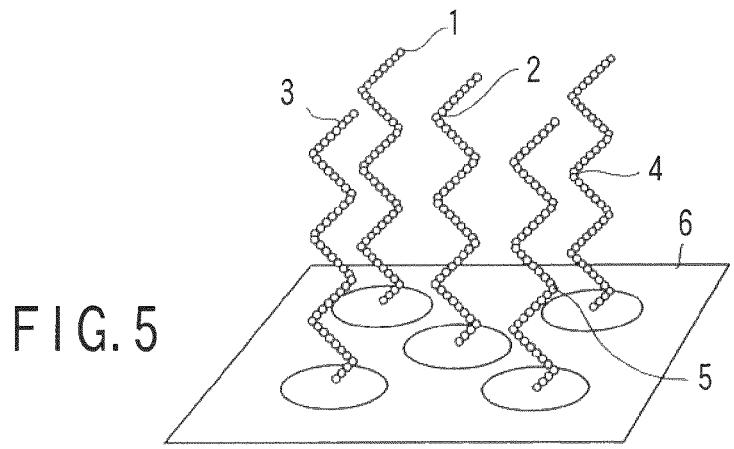
FIG. 5 is a schematic view illustrating an example of a DNA chip for identification of HPV genotype.

(4) Preparation of Nucleic Acid Probe-Immobilized Slide Glass (FIG. 5)

The DNA probes 1-5 were immobilized on the slide glass 6. The nucleic acid sequence of them is shown in Table 8-1.

TABLE 8-1

Probe sequence

| Title | SEQ ID No. | Complementary sequence (5' → 3') |
|---|---|---|
| HPV16 | 7 | TCTGAACTAGATATGGCAGCACATAATGAC |
| HPV18 | 8 | TGCCCAGGTACAGGAGACTGTGTAGAAGCA |
| HPV26 | 9 | AGTGGATGCAGATGCTGCAGATAATGTACT |
| HPV31 | 10 | GTATCACTGTTTGCAATTGCAGCACAAACA |
| rDNA | 11 | CTGGACGAAGACTGACGCTC |

*The terminal is modified by amino group.

HPV's 16 to 31 were used as sequences specific to the subtypes of HPV, while the rDNA's as negative controls. Each probe was modified with an amino group at the terminal, and was immobilized on a carbodiimide-treated slide glass substrate by spotting the probe solution thereon. Finally, the substrate was washed with ultrapure water and air-dried, to give a DNA chip.

(5) Hybridization of LAMP Products to Nucleic Acid Probe

The LAMP products amplified in (3) above were used as a nucleic acid sample. The DNA chip prepared in (4) was hybridized by dipping it into the LAMP product solution containing 2×SSC salt added and leaving it therein at 35° C. for 60 minutes. Subsequently, Cy5-labelled nucleic acid of SEQ ID No. 7 was added thereto, and the mixture was left at 35° C. for 15 minutes and washed with ultrapure water slightly. The fluorescence intensity was detected by using Tyhoon manufactured by Amersham.

(6) Results

Fluorescence measurement showed significant emission only on HPV16 probe-immobilized spots, indicating that it was possible to detect nucleic acids amplified by LAMP reaction specifically to the sequence.

Figure 6:
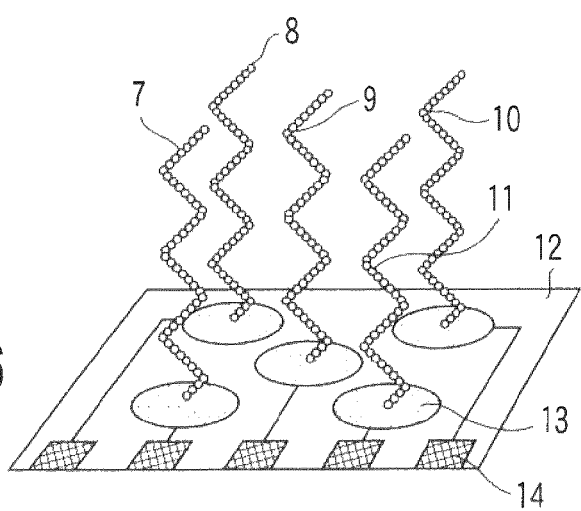
FIG. 6 is a schematic view illustrating another example of the DNA chip for identification of HPV genotype.

(7) Preparation of Nucleic Acid Probe-Immobilized Electrode (FIG. 6)

The DNA probes 7-11 were immobilized on the electrode 13 placed on the support 12. The nucleic acid sequence of them is shown in Table 8-2. Connection part 14 may be placed on the support 12.

TABLE 8-2

Probe sequence

| Title | SEQ ID No. | Complementary sequence (5' → 3') |
|---|---|---|
| HPV16 | 7 | TCTGAAGTAGATATGGCAGCACATAATGAC |
| HPV18 | 8 | TGCCCAGGTACAGGAGACTGTGTAGAAGCA |
| HPV26 | 9 | AGTGGATGCAGATGCTGCAGATAATGTACT |
| HPV31 | 10 | GTATCACTGTTTGCAATTGCAGCACAAACA |
| rDNA | 11 | CTGGACGAAGACTGACGCTC |

*The terminal is modified by thiol group.

HPV's 16 to 31 are used as sequences specific to the subtypes of HPV, while the rDNA's as negative controls. Each probe is modified with an amino group at the terminal, and is immobilized on a gold electrode by spotting the probe solution thereon. Finally, the substrate is washed with ultrapure water and air-dried, to give a DNA chip.

(8) Hybridization of LAMP Products to Nucleic Acid Probe

The DNA chip prepared in (7) is hybridized by dipping it into the LAMP product solution containing added 2×SSC salt and leaving it therein at 35° C. for 60 minutes. The electrode is dipped into a phosphate buffer solution containing a 50 μM intercalating agent Hoechst 33258 for 15 minutes, and the oxidative current response of the Hoechst 33258 molecule is determined, (9) Result Voltammetric analysis indicates that significant current signals are detectable only on the spots carrying the immobilized HPV16 probe. For this reason, it has been clear that it is possible to detect nucleic acids amplified by LAMP reaction sequence-specifically.

(10) Multiamplification by LAMP Method 1

Figure 7:
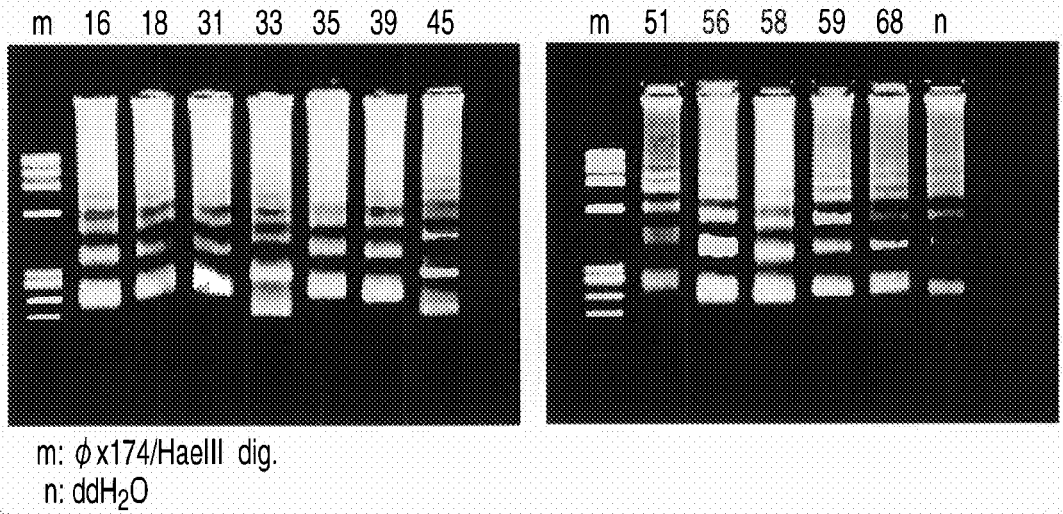
FIG. 7 is a chart showing an example of electrophoretic photographs after LAMP amplification.
Figure 8:
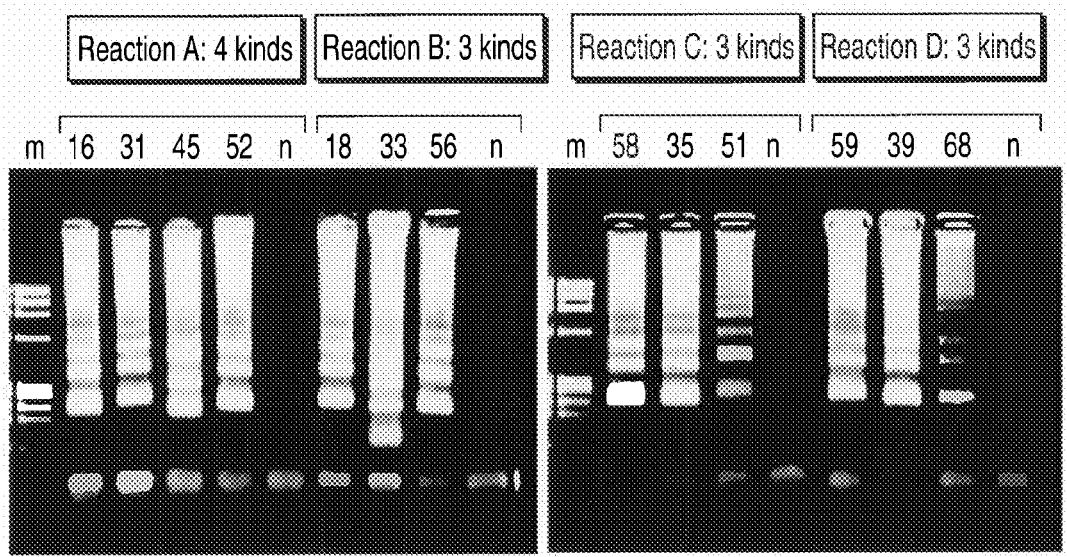
FIG. 8 is a chart showing another example of the electrophoretic photographs after LAMP amplification.

Amplification according to a kind of template was performed by using the primer shown in Table 9. As a result, a ladder-shaped band characteristic to LAMP amplification was observed, and genotype-specific amplification was confirmed (FIG. 7). Then, amplification according to a kind of template by using multiple primers, i.e., multiple mixed primer sets respectively in groups A to D, confirmed genotype-specific amplification (FIG. 8).

TABLE 9

| Group | Type | SEQ ID No. |
|---|---|---|
| A | 16 | 116 |
|  |  | 117 |
|  |  | 210 |
|  |  | 211 |
| B | 18 | 120 |
|  |  | 121 |
|  |  | 212 |
|  |  | 213 |
| C | 58 | 125 |
|  |  | 128 |
|  |  | 230 |
|  |  | 231 |

TABLE 9-continued

| Group | Type | SEQ ID No. |
|---|---|---|
| C | 35 | 136 |
|   |    | 137 |
|   |    | 232 |
|   |    | 233 |
| B | 56 | 142 |
|   |    | 143 |
|   |    | 234 |
|   |    | 235 |
| A | 31 | 147 |
|   |    | 148 |
|   |    | 214 |
|   |    | 217 |
| A | 45 | 152 |
|   |    | 158 |
|   |    | 218 |
|   |    | 220 |
| B | 33 | 165 |
|   |    | 167 |
|   |    | 222 |
|   |    | 225 |
| A | 52 | 171 |
|   |    | 174 |
|   |    | 226 |
|   |    | 228 |
| D | 59 | 179 |
|   |    | 180 |
|   |    | 236 |
|   |    | 237 |
| D | 39 | 187 |
|   |    | 188 |
|   |    | 240 |
|   |    | 242 |
| C | 51 | 194 |
|   |    | 196 |
|   |    | 244 |
|   |    | 245 |
| D | 68 | 202 |
|   |    | 203 |
|   |    | 247 |
|   |    | 253 |

(11) Detection of LAMP Multiamplification Products 1

The amplification products shown in FIG. 8 were detected by using a current-detecting DNA chip carrying the probes of sequence numbers 605, 623, 635, 652, 683, 763, and 793 immobilized on the same chip. The probes are designed to react specifically with the nucleic acids of sequence numbers of 16, 18, 31, 33, 45, 58, and 68, respectively. Reaction of the sample amplified only by using the templates 16 and 18 resulted in increase in current only on the electrodes corresponding to the templates, indicating genotype-specific detection (FIG. 9).

(12) Multiamplification by LAMP Method 2

Primer sets of groups A to D shown in Table 10 were mixed respectively to give multiple primer sets. The amplification of a kind of template was performed by using the multiple primer sets. The amplification was performed at a template concentration of $10^3$ copies/reaction at 65 degrees for 2 hours. As a result, genotype-specific amplification was confirmed (FIG. 10).

TABLE 10

| Group | Type | SEQ ID No. |
|---|---|---|
| A | 16 | 254 |
|   |    | 255 |
|   |    | 257 |
|   |    | 258 |
| B | 18 | 120 |
|   |    | 121 |
|   |    | 212 |
|   |    | 213 |
| C | 58 | 125 |
|   |    | 128 |
|   |    | 230 |
|   |    | 231 |
| B | 35 | 136 |
|   |    | 139 |
|   |    | 232 |
|   |    | 233 |
| B | 56 | 142 |
|   |    | 143 |
|   |    | 234 |
|   |    | 235 |
| A | 31 | 147 |
|   |    | 148 |
|   |    | 214 |
|   |    | 217 |
| A | 45 | 281 |
|   |    | 388 |
|   |    | 284 |
|   |    | 285 |
| C | 33 | 379 |
|   |    | 380 |
|   |    | 381 |
|   |    | 382 |
| A | 52 | 171 |
|   |    | 174 |
|   |    | 404 |
|   |    | 403 |
| D | 59 | 302 |
|   |    | 303 |
|   |    | 304 |
|   |    | 305 |
| D | 39 | 187 |
|   |    | 188 |
|   |    | 240 |
|   |    | 242 |
| C | 51 | 286 |
|   |    | 287 |
|   |    | 288 |
|   |    | 289 |
| D | 68 | 202 |
|   |    | 411 |
|   |    | 250 |
|   |    | 253 |

(13) Detection of LAMP Multiamplification Products 2

The amplification products shown in FIG. 10 were detected by using a current-detecting DNA chip carrying the probes of SEQ ID No. 602, 623, 635, 647, 657, 681, 694, 750, 762, 774, and 793 immobilized on the same chip. The probes are designed to react specifically with the nucleic acids of sequence numbers of 16, 18, 31, 33, 35, 45, 51, 56, 58, 59, and 68, respectively. Reaction of the sample obtained by amplification by using each of the 11 kinds of templates resulted in increase in current only on the electrode corresponding to the template, indicating genotype specific detection of 11 kinds of genotypes.

(14) Multiamplification by LAMP Method 3

Primer sets of groups A to D shown in Table 11 were mixed respectively to give multiple primer sets. Specifically, tube A contains primer sets with primers 16, 35, and 59; tube B contains a primer set with primers 18, 39, and 56; tube C contains a primer set with primers 45, 51, 58, and 68; and tube D contains a primer set with primers 31, 33, and 52. Further, tube E contained primers of SEQ ID Nos. 801, 802, 803, and 804 prepared for amplification of human β-globin gene (Table 12). The amplification of a kind of template was performed by using the multiple primer sets respectively. A plasmid corresponding to each HPV type was used as the template, and the hybridization was performed at a concentration of 10³ copies/reaction at 63° C. for 1.5 hours, which confirmed genotype-specific amplification.

TABLE 11

| Group | Type | SEQ ID No. |
|---|---|---|
| A | 16 | 126 |
| | | 128 |
| | | 132 |
| | | 136 |
| | | 138 |
| | 35 | 277 |
| | | 281 |
| | | 278 |
| | | 276 |
| | | 280 |
| | 59 | 526 |
| | | 527 |
| | | 524 |
| | | 523 |
| | | 529 |
| B | 18 | 162 |
| | | 164 |
| | | 167 |
| | | 166 |
| | | 170 |
| | 39 | 319 |
| | | 320 |
| | | 327 |
| | | 324 |
| | | 328 |
| | 56 | 453 |
| | | 454 |
| | | 457 |
| | | 456 |
| | | 458 |
| C | 45 | 366 |
| | | 363 |
| | | 361 |
| | | 359 |
| | | 370 |
| | 51 | 395 |
| | | 388 |
| | | 399 |
| | | 391 |
| | | 402 |
| | 58 | 477 |
| | | 475 |
| | | 474 |
| | | 476 |
| | | 480 |
| | 68 | 548 |
| | | 546 |
| | | 549 |
| | | 547 |
| | | 572 |
| D | 31 | 210 |
| | | 208 |
| | | 203 |
| | | 205 |
| | | 214 |
| | 33 | 248 |
| | | 251 |
| | | 242 |
| | | 244 |
| | | 255 |
| | 52 | 420 |
| | | 422 |
| | | 425 |
| | | 429 |
| | | 431 |

TABLE 12

| Group | SEQ ID No. | Sequence (5' → 3') |
|---|---|---|
| β-globin | 795 | TGATGGTATGGGGCCAAGAG |
| | 796 | GAGGTCTAAGTGATGACAGCCGCTGAGGGTTTGAAGTCCAACTCC |
| | 797 | AATCTACTCCCAGGAGCAGGGCTAGTGAACACAGTTGTGTCAGAAG |
| | 798 | GAGTCAGATGCACCATGGTG |
| | 799 | TGAGGTCTAAGTGATGACAGCCGCTGAGGGTTTGAAGTCCAACTCC |
| | 800 | AATCTACTCCCAGGAGCAGGGAAGTGAACACAGTTGTGTCAGAAGC |
| | 801 | AGGGCTGAGGGTTTGAAGTC |
| | 802 | TGAGGTCTAAGTGATGACAGCCGCAACTCCTAAGCCAGTGCCAGA |
| | 803 | CTAGGGTTGGCCAATCTACTCCCAATAGATGGCTCTGCCCTGAC |
| | 804 | TGAACACAGTTGTGTCAGAAGC |

(15) Detection of LAMP Multiamplification Products 3

The amplification products above were detected by using a current-detecting DNA chip carrying the probes of SEQ ID Nos. 600, 623, 630, 641, 654, 673, 676, 699, 725, 750, 752, 771, and 783 on a single chip. These probes are designed to react specifically with the sequences of 16, 18, 31, 33, 35, 39, 45, 51, 52, 56, 58, 59, and 68, respectively. The oligonucleotide of SEQ ID No. 813 as a probe for detecting β-globin gene was immobilized as the positive control of reaction, and the oligonucleotide of SEQ ID No. 814 was immobilized as the negative control on the same substrate (Table 13). Reaction of the sample obtained by amplification by using each of the 13 kinds of templates resulted in increase in current only on the electrode corresponding to the template, indicating genotype specific detection of the 13 kinds of genotypes.

TABLE 13

| Group | SEQ ID No. | Sequence (5' → 3') |
|---|---|---|
| Positive control | 805 | ATAAAAGTCAGGGCAGAGCCATCTATTGCTTAC |
| | 806 | TCAGGGCAGAGCCATCTATTGCTTACATTT |
| | 807 | GTCAGGGCAGAGCCATCTATTGCTTACATTTGCTT |
| | 808 | AGGGCAGGAGCCAGGGCTGGGCATAAAAGTCAGGG |
| | 809 | AAAGTCAGGGCAGAGCCATCTATTGCTTACATTTG |
| | 810 | TGGGCATAAAAGTCAGGGCAGAGCCATC |
| | 811 | CAGGAGCAGGGAGGGCAGGAGCCAGGGCTGGGCAT |
| | 812 | CAGGGAGGGCAGGAGCCAGGGCTGGGCAT |
| | 813 | CAGGAGCAGGGAGGGCAGGAGCCAGGG |
| Negative control | 814 | GACTATAAACATGCTTTCCGTGGCA |

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A set of isolated nucleic acid primers suitable for LAMP amplification and detection of human papilloma virus genotypes, wherein the set of nucleic acid primers is selected from the group consisting of:

Set 1 consisting of five nucleic acid primers consisting of SEQ ID Nos. 136, 132, 126, 128, and 138;
Set 2 consisting of five nucleic acid primers consisting of SEQ ID Nos. 278, 277, 276, 281 and 280;
Set 3 consisting of five nucleic acid primers consisting of SEQ ID Nos. 527, 524, 526, 523, and 529;
Set 4 consisting of five nucleic acid primers consisting of SEQ ID Nos. 164, 167, 162, 166, and 170;
Set 5 consisting of five nucleic acid primers consisting of SEQ ID Nos. 320, 327, 319, 324, and 328;
Set 6 consisting of five nucleic acid primers consisting of SEQ ID Nos. 454, 457, 453, 456, and 458;
Set 7 consisting of five nucleic acid primers consisting of SEQ ID Nos. 363, 359, 366, 361, and 370;
Set 8 consisting of five nucleic acid primers consisting of SEQ ID Nos. 399, 391, 395, 388, and 402;
Set 9 consisting of five nucleic acid primers consisting of SEQ ID Nos. 474, 476, 477, 475, and 480;
Set 10 consisting of five nucleic acid primers consisting of SEQ ID Nos. 549, 547, 548, 546, and 572;
Set 11 consisting of five nucleic acid primers consisting of SEQ ID Nos. 208, 203, 210, 205, and 214;

Set 12 consisting of five nucleic acid primers consisting of SEQ ID Nos. 251, 244, 248, 242, 255; and Set 13 consisting of five nucleic acid primers consisting of SEQ ID Nos. 422, 425, 420, 429, and 431.

2. A mixture of primer sets suitable for LAMP amplification and detection of human papilloma virus genotypes, selected from the group consisting of:

Mixture A comprising Set 1, 2 and 3 according to claim 1;
Mixture B comprising Set 4, 5 and 6 according to claim 1;
Mixture C comprising Set 7, 8, 9 and 10 according to claim 1; and
Mixture D comprising Set 11, 12 and 13 according to claim 1.

3. A detection kit suitable for detecting human papilloma virus genotypes, comprising at least one Primer-Probe Set selected from the group consisting of:

Primer-Probe Set 1 consisting of Set 1 according to claim 1 and at least one nucleic acid probe consisting of one of SEQ ID Nos. 600 and 597, Primer-Probe Set 2 consisting of Set 2 according to claim 1 and a nucleic acid probe consisting of SEQ ID No. 654, Primer-Probe Set 3 consisting of Set 3 according to claim 1 and at least one nucleic acid probe consisting of one of SEQ ID Nos. 771 and 768, Primer-Probe Set 4 consisting of Set 4 according to claim 1 and a nucleic acid probe consisting of SEQ ID No. 623, Primer-Probe Set 5 consisting of Set 5 according to claim 1 and at least one nucleic acid probe consisting of one of SEQ ID Nos. 673 and 667, Primer-Probe Set 6 consisting of Set 6 according to claim 1 and at least one nucleic acid probe consisting of one of SEQ ID Nos. 750 and 741, Primer-Probe Set 7 consisting of Set 7 according to claim 1 and a nucleic acid probe consisting of SEQ ID No. 676, Primer-Probe Set 8 consisting of Set 8 according to claim 1 and at least one nucleic acid probe consisting of one of SEQ ID Nos. 699 and 684, Primer-Probe Set 9 consisting of Set 9 according to claim 1 and a nucleic acid probe consisting of SEQ ID No. 752, Primer-Probe Set 10 consisting of set 10 according to claim 1 and a nucleic acid probe consisting of SEQ ID No. 783, Primer-Probe Set 11 consisting of Set 11 according to claim 1 and a nucleic acid probe consisting of SEQ ID No. 630, Primer-Probe Set 12 consisting of Set 12 according to claim 1 and a nucleic acid probe consisting of SEQ ID No. 641, and Primer-Probe Set 13 consisting of Set 13 according to claim 1 and at least one nucleic acid probe consisting of one of SEQ ID Nos. 725 and 713.

4. The kit according to claim 3, wherein the nucleic acid probe is immobilized on a support surface.

5. The kit according to claim 4, wherein the support surface is an electrode.

6. A detection kit suitable for detecting human papilloma virus genotypes, comprising at least one Detection Set selected from the group consisting of Detection set A, B, C, and D, wherein:

Detection Set A comprises:

Primer-Probe Set 1 consisting of Set 1 according to claim 1 and at least one nucleic acid probe consisting of one of SEQ ID Nos. 600 and 597, Primer-Probe Set 2 consisting of Set 2 according to claim 1 and a nucleic acid probe consisting of SEQ ID No. 654, and Primer-Probe Set 3 consisting of Set 3 according to claim 1 and at least one nucleic acid probe consisting of one of SEQ ID Nos. 771 and 768;

Detection Set B comprises:

Primer-Probe Set 4 consisting of Set 4 according to claim 1 and a nucleic acid probe consisting of SEQ ID No. 623, Primer-Probe Set 5 consisting of Set 5 according to claim 1 and at least one nucleic acid probe consisting of one of SEQ ID Nos. 673 and 667, and Primer-Probe Set 6 consisting of Set 6 according to claim 1 and at least one nucleic acid probe consisting of one of SEQ ID Nos. 750 and 741;

Detection Set C comprises:

Primer-Probe Set 7 consisting of Set 7 according to claim 1 and a nucleic acid probe consisting of SEQ ID No. 676, Primer-Probe Set 8 consisting of Set 8 according to claim 1 and at least one nucleic acid probe consisting of one of SEQ ID Nos. 699 and 684, and Primer-Probe Set 9 consisting of Set 9 according to claim 1 and a nucleic acid probe consisting of SEQ ID No. 752, and Primer-Probe Set 10 consisting of Set 10 according to claim 1 and a nucleic acid probe consisting of SEQ ID No. 783; and Detection Set D comprises:

Primer-Probe Set 11 consisting of Set 11 according to claim 1 and a nucleic acid probe consisting of SEQ ID No. 630, Primer-Probe Set 12 consisting of Set 12 according to claim 1 and a nucleic acid probe consisting of SEQ ID No. 641, and Primer-Probe Set 13 consisting of Set 13 according to claim 1 and at least one nucleic acid probe consisting of one of SEQ ID Nos. 725 and 713.

7. A detection kit suitable for detecting genotypes of human papilloma virus, comprising at least one mixture of primer sets and a DNA chip, wherein:

the mixture is selected from the group consisting of:

Mixture A comprising Set 1, 2, and 3 according to claim 1;
Mixture B comprising Set 4, 5, and 6 according to claim 1;
Mixture C comprising Set 7, 8, 9, and 10 according to claim 1; and
Mixture D comprising Set 11, 12, and 13 according to claim 1; and wherein:

the DNA chip comprises nucleic acid probes consisting of:
one of SEQ ID Nos. 600 and 597;
SEQ ID No. 654;
one of SEQ ID Nos. 771 and 768;
SEQ ID No. 623;
one of SEQ ID Nos. 673 and 667;
one of SEQ ID Nos. 750 and 741;
SEQ ID No. 676;
one of SEQ ID Nos. 699 and 684;
SEQ ID No. 752;
SEQ ID No. 783;
SEQ ID No. 630;
SEQ ID No. 641; and
one of SEQ ID Nos. 725 and 713 and wherein the nucleic acid probes are immobilized on a support surface.

* * * * *

UNITED STATES PATENT AND TRADEMARK OFFICE
CERTIFICATE OF CORRECTION

| | | |
|---|---|---|
| PATENT NO. | : 7,910,719 B2 | Page 1 of 1 |
| APPLICATION NO. | : 12/134420 | |
| DATED | : March 22, 2011 | |
| INVENTOR(S) | : Koji Hashimoto et al. | |

It is certified that error appears in the above-identified patent and that said Letters Patent is hereby corrected as shown below:

On the title page, Item (63), the Related U.S. Application Data information is incorrect. Item (63) should read:

-- Related U.S. Application Data

(63) Continuation of application No. PCT/JP2006/325010, filed on Dec. 8, 2006. --

Signed and Sealed this
Tenth Day of May, 2011

David J. Kappos
*Director of the United States Patent and Trademark Office*

SEQUENCE LISTING

<160> NUMBER OF SEQ ID NOS: 815

<210> SEQ ID NO 1
<211> LENGTH: 25
<212> TYPE: DNA
<213> ORGANISM: Human papillomavirus

<400> SEQUENCE: 1
gaatatgatt tacagtttat ttttc                                         25

<210> SEQ ID NO 2
<211> LENGTH: 23
<212> TYPE: DNA
<213> ORGANISM: Human papillomavirus

<400> SEQUENCE: 2
tttgttactg ttgttgatac tac                                           23

<210> SEQ ID NO 3
<211> LENGTH: 20
<212> TYPE: DNA
<213> ORGANISM: Human papillomavirus

<400> SEQUENCE: 3
gcacagggcc acaataatgg                                               20

<210> SEQ ID NO 4
<211> LENGTH: 30
<212> TYPE: DNA
<213> ORGANISM: Human papillomavirus

<400> SEQUENCE: 4
gtcattatgt gctgccatat ctacttcaga                                    30

<210> SEQ ID NO 5
<211> LENGTH: 20
<212> TYPE: DNA
<213> ORGANISM: Human papillomavirus

<400> SEQUENCE: 5
gatcagtttc ctttaggacg                                               20

<210> SEQ ID NO 6
<211> LENGTH: 20
<212> TYPE: DNA
<213> ORGANISM: Human papillomavirus

<400> SEQUENCE: 6 aaattttac tacaagcagg                                                20

<210> SEQ ID NO 7
<211> LENGTH: 30
<212> TYPE: DNA
<213> ORGANISM: Human papillomavirus

<400> SEQUENCE: 7
tctgaagtag atatggcagc acataatgac                                    30

<210> SEQ ID NO 8
<211> LENGTH: 30
<212> TYPE: DNA
<213> ORGANISM: Human papillomavirus

```
<400> SEQUENCE: 8
tgcccaggta caggagactg tgtagaagca                                    30

<210> SEQ ID NO 9
<211> LENGTH: 30
<212> TYPE: DNA
<213> ORGANISM: Human papillomavirus

<400> SEQUENCE: 9
agtggatgca gatgctgcag ataatgtact                                    30

<210> SEQ ID NO 10
<211> LENGTH: 30
<212> TYPE: DNA
<213> ORGANISM: Human papillomavirus

<400> SEQUENCE: 10
gtatcactgt ttgcaattgc agcacaaaca                                    30

<210> SEQ ID NO 11
<211> LENGTH: 20
<212> TYPE: DNA
<213> ORGANISM: Escherichia coli

<400> SEQUENCE: 11
ctggacgaag actgacgctc                                               20

<210> SEQ ID NO 12
<211> LENGTH: 48
<212> TYPE: DNA
<213> ORGANISM: Human papillomavirus

<400> SEQUENCE: 12
gaaaaataaa ctgtaaatca tattctttgt tactgtggta gatactac                48

<210> SEQ ID NO 13
<211> LENGTH: 20
<212> TYPE: DNA
<213> ORGANISM: Human papillomavirus

<400> SEQUENCE: 13
gcacagggcc acaataatgg                                               20

<210> SEQ ID NO 14
<211> LENGTH: 44
<212> TYPE: DNA
<213> ORGANISM: Human papillomavirus

<400> SEQUENCE: 14
tttttgggaa gtaaatttaa aggacgtcct aaaggaaact gatc                    44

<210> SEQ ID NO 15
<211> LENGTH: 20
<212> TYPE: DNA
<213> ORGANISM: Human papillomavirus

<400> SEQUENCE: 15
cctgcttgta gtaaaaattt                                               20

<210> SEQ ID NO 16
<211> LENGTH: 20
<212> TYPE: DNA
<213> ORGANISM: Human papillomavirus
```

```
<400> SEQUENCE: 16
tgatttacag tttattttc                                          20

<210> SEQ ID NO 17
<211> LENGTH: 25
<212> TYPE: DNA
<213> ORGANISM: Human papillomavirus

<400> SEQUENCE: 17
gaatatgatt tacagtttat ttttc                                   25

<210> SEQ ID NO 18
<211> LENGTH: 28
<212> TYPE: DNA
<213> ORGANISM: Human papillomavirus

<400> SEQUENCE: 18
gaagaatatg atttacagtt tattttc                                 28

<210> SEQ ID NO 19
<211> LENGTH: 28
<212> TYPE: DNA
<213> ORGANISM: Human papillomavirus

<400> SEQUENCE: 19
gaggaatatg atttacagtt tatttttc                                28

<210> SEQ ID NO 20
<211> LENGTH: 25
<212> TYPE: DNA
<213> ORGANISM: Human papillomavirus

<400> SEQUENCE: 20
gagtatgatt tacaatttat ttttc                                   25

<210> SEQ ID NO 21
<211> LENGTH: 25
<212> TYPE: DNA
<213> ORGANISM: Human papillomavirus

<400> SEQUENCE: 21
gagtttgatt tacagtttat ttttc                                   25

<210> SEQ ID NO 22
<211> LENGTH: 25
<212> TYPE: DNA
<213> ORGANISM: Human papillomavirus

<400> SEQUENCE: 22
gaatttgatt tacaatttat ttttc                                   25

<210> SEQ ID NO 23
<211> LENGTH: 25
<212> TYPE: DNA
<213> ORGANISM: Human papillomavirus

<400> SEQUENCE: 23
gaatatgatt tacagtttat ttttc                                   25

<210> SEQ ID NO 24
<211> LENGTH: 25
<212> TYPE: DNA
<213> ORGANISM: Human papillomavirus
```

```
<400> SEQUENCE: 24
gaatatgatt tgcagtttat ttttc                                          25

<210> SEQ ID NO 25
<211> LENGTH: 25
<212> TYPE: DNA
<213> ORGANISM: Human papillomavirus

<400> SEQUENCE: 25
gaatatgaat tacagtttgt gtttc                                          25

<210> SEQ ID NO 26
<211> LENGTH: 25
<212> TYPE: DNA
<213> ORGANISM: Human papillomavirus

<400> SEQUENCE: 26
gaatttgatt tacaatttat atttc                                          25

<210> SEQ ID NO 27
<211> LENGTH: 25
<212> TYPE: DNA
<213> ORGANISM: Human papillomavirus

<400> SEQUENCE: 27
gaatatgata tacagtttat atttc                                          25

<210> SEQ ID NO 28
<211> LENGTH: 25
<212> TYPE: DNA
<213> ORGANISM: Human papillomavirus

<400> SEQUENCE: 28
gaatatgatc tacagtttgt ttttc                                          25

<210> SEQ ID NO 29
<211> LENGTH: 25
<212> TYPE: DNA
<213> ORGANISM: Human papillomavirus

<400> SEQUENCE: 29
gagtatgacc tgcagtttgt gtttc                                          25

<210> SEQ ID NO 30
<211> LENGTH: 25
<212> TYPE: DNA
<213> ORGANISM: Human papillomavirus

<400> SEQUENCE: 30
gaatatgatt tacagtttat ttttc                                          25

<210> SEQ ID NO 31
<211> LENGTH: 25
<212> TYPE: DNA
<213> ORGANISM: Human papillomavirus

<400> SEQUENCE: 31
gagtatgatt tacaatttat atttc                                          25

<210> SEQ ID NO 32
<211> LENGTH: 25
<212> TYPE: DNA
<213> ORGANISM: Human papillomavirus
```

```
<400> SEQUENCE: 32
gagtttgatt tgcagtttat ttttc                                        25

<210> SEQ ID NO 33
<211> LENGTH: 25
<212> TYPE: DNA
<213> ORGANISM: Human papillomavirus

<400> SEQUENCE: 33
gaatatgatg tgcaatttat atttc                                        25

<210> SEQ ID NO 34
<211> LENGTH: 25
<212> TYPE: DNA
<213> ORGANISM: Human papillomavirus

<400> SEQUENCE: 34
gaatatgatt tacagtttat ttttc                                        25

<210> SEQ ID NO 35
<211> LENGTH: 25
<212> TYPE: DNA
<213> ORGANISM: Human papillomavirus

<400> SEQUENCE: 35
gagtatgaat tgcaatttat ttttc                                        25

<210> SEQ ID NO 36
<211> LENGTH: 25
<212> TYPE: DNA
<213> ORGANISM: Human papillomavirus

<400> SEQUENCE: 36
gaatttgatt tacaatttat ttttc                                        25

<210> SEQ ID NO 37
<211> LENGTH: 25
<212> TYPE: DNA
<213> ORGANISM: Human papillomavirus

<400> SEQUENCE: 37
gaatatgaat tacaatttgt gtttc                                        25

<210> SEQ ID NO 38
<211> LENGTH: 25
<212> TYPE: DNA
<213> ORGANISM: Human papillomavirus

<400> SEQUENCE: 38
gaatatgaat tacaatttgt ttttc                                        25

<210> SEQ ID NO 39
<211> LENGTH: 25
<212> TYPE: DNA
<213> ORGANISM: Human papillomavirus

<400> SEQUENCE: 39
gaatatgact tacagtttgt ttttc                                        25

<210> SEQ ID NO 40
<211> LENGTH: 25
<212> TYPE: DNA
<213> ORGANISM: Human papillomavirus
```

```
<400> SEQUENCE: 40
gagtttgatt tgcaatttat ttttc                                25

<210> SEQ ID NO 41
<211> LENGTH: 25
<212> TYPE: DNA
<213> ORGANISM: Human papillomavirus

<400> SEQUENCE: 41
gaatatgaac tacagtttgt gtttc                                25

<210> SEQ ID NO 42
<211> LENGTH: 25
<212> TYPE: DNA
<213> ORGANISM: Human papillomavirus

<400> SEQUENCE: 42
gaatatgatt tgcaatttat atttc                                25

<210> SEQ ID NO 43
<211> LENGTH: 25
<212> TYPE: DNA
<213> ORGANISM: Human papillomavirus

<400> SEQUENCE: 43
gaaahataaa ytgyaadtca taytc                                25

<210> SEQ ID NO 44
<211> LENGTH: 20
<212> TYPE: DNA
<213> ORGANISM: Human papillomavirus

<400> SEQUENCE: 44
tttgttactg tggtagatac                                      20

<210> SEQ ID NO 45
<211> LENGTH: 23
<212> TYPE: DNA
<213> ORGANISM: Human papillomavirus

<400> SEQUENCE: 45
tttgttactg tggtagatac tac                                  23

<210> SEQ ID NO 46
<211> LENGTH: 23
<212> TYPE: DNA
<213> ORGANISM: Human papillomavirus

<400> SEQUENCE: 46
tttgttactg tggtagatac cac                                  23

<210> SEQ ID NO 47
<211> LENGTH: 23
<212> TYPE: DNA
<213> ORGANISM: Human papillomavirus

<400> SEQUENCE: 47
tttgttactg tggtagatac cac                                  23

<210> SEQ ID NO 48
<211> LENGTH: 23
<212> TYPE: DNA
<213> ORGANISM: Human papillomavirus
```

```
<400> SEQUENCE: 48
tttgttactg tagttgatac tac                                          23

<210> SEQ ID NO 49
<211> LENGTH: 23
<212> TYPE: DNA
<213> ORGANISM: Human papillomavirus

<400> SEQUENCE: 49
tttgttactg ttgttgatac tac                                          23

<210> SEQ ID NO 50
<211> LENGTH: 23
<212> TYPE: DNA
<213> ORGANISM: Human papillomavirus

<400> SEQUENCE: 50
tttgttactg tggtagatac cac                                          23

<210> SEQ ID NO 51
<211> LENGTH: 23
<212> TYPE: DNA
<213> ORGANISM: Human papillomavirus

<400> SEQUENCE: 51
tttgttactg ttgtggacac cac                                          23

<210> SEQ ID NO 52
<211> LENGTH: 23
<212> TYPE: DNA
<213> ORGANISM: Human papillomavirus

<400> SEQUENCE: 52
tttgttactg tggtagatac cac                                          23

<210> SEQ ID NO 53
<211> LENGTH: 23
<212> TYPE: DNA
<213> ORGANISM: Human papillomavirus

<400> SEQUENCE: 53
tttctaactg ttgtggatac tac                                          23

<210> SEQ ID NO 54
<211> LENGTH: 23
<212> TYPE: DNA
<213> ORGANISM: Human papillomavirus

<400> SEQUENCE: 54
tttgttactg tggtagatac cac                                          23

<210> SEQ ID NO 55
<211> LENGTH: 23
<212> TYPE: DNA
<213> ORGANISM: Human papillomavirus

<400> SEQUENCE: 55
tttttaactg ttgtagatac tac                                          23

<210> SEQ ID NO 56
<211> LENGTH: 23
<212> TYPE: DNA
<213> ORGANISM: Human papillomavirus
```

```
<400> SEQUENCE: 56
tttgttactg tagttgatac aac                                           23

<210> SEQ ID NO 57
<211> LENGTH: 23
<212> TYPE: DNA
<213> ORGANISM: Human papillomavirus

<400> SEQUENCE: 57
tttcttactg ttgtggacac tac                                           23

<210> SEQ ID NO 58
<211> LENGTH: 23
<212> TYPE: DNA
<213> ORGANISM: Human papillomavirus

<400> SEQUENCE: 58
tttgttacag ttgtagacac cac                                           23

<210> SEQ ID NO 59
<211> LENGTH: 23
<212> TYPE: DNA
<213> ORGANISM: Human papillomavirus

<400> SEQUENCE: 59
tttttaactg tggttgatac tac                                           23

<210> SEQ ID NO 60
<211> LENGTH: 23
<212> TYPE: DNA
<213> ORGANISM: Human papillomavirus

<400> SEQUENCE: 60
tttgttactg tagtggacac tac                                           23

<210> SEQ ID NO 61
<211> LENGTH: 23
<212> TYPE: DNA
<213> ORGANISM: Human papillomavirus

<400> SEQUENCE: 61
tttattacct gtgttgatac tac                                           23

<210> SEQ ID NO 62
<211> LENGTH: 23
<212> TYPE: DNA
<213> ORGANISM: Human papillomavirus

<400> SEQUENCE: 62
tttgtcacag ttgtggatac cac                                           23

<210> SEQ ID NO 63
<211> LENGTH: 23
<212> TYPE: DNA
<213> ORGANISM: Human papillomavirus

<400> SEQUENCE: 63
tttgtaactg ttgtggatac cac                                           23

<210> SEQ ID NO 64
<211> LENGTH: 23
<212> TYPE: DNA
<213> ORGANISM: Human papillomavirus
```

-continued

```
<400> SEQUENCE: 64
tttgttactg tagtagatac tac                                               23

<210> SEQ ID NO 65
<211> LENGTH: 23
<212> TYPE: DNA
<213> ORGANISM: Human papillomavirus

<400> SEQUENCE: 65
tttgttaccg tggttgatac cac                                               23

<210> SEQ ID NO 66
<211> LENGTH: 23
<212> TYPE: DNA
<213> ORGANISM: Human papillomavirus

<400> SEQUENCE: 66
tttgtaaccg ttgtggatac cac                                               23

<210> SEQ ID NO 67
<211> LENGTH: 23
<212> TYPE: DNA
<213> ORGANISM: Human papillomavirus

<400> SEQUENCE: 67
tttgttactg ttgtggatac tac                                               23

<210> SEQ ID NO 68
<211> LENGTH: 23
<212> TYPE: DNA
<213> ORGANISM: Human papillomavirus

<400> SEQUENCE: 68
tttcttactg ttgtggatac cac                                               23

<210> SEQ ID NO 69
<211> LENGTH: 23
<212> TYPE: DNA
<213> ORGANISM: Human papillomavirus

<400> SEQUENCE: 69
tttkttachg tkgtdgatac yac                                               23

<210> SEQ ID NO 70
<211> LENGTH: 20
<212> TYPE: DNA
<213> ORGANISM: Human papillomavirus

<400> SEQUENCE: 70
gcacagggcc acaataatgg                                                   20

<210> SEQ ID NO 71
<211> LENGTH: 20
<212> TYPE: DNA
<213> ORGANISM: Human papillomavirus

<400> SEQUENCE: 71
gcacagggac ataacaatgg                                                   20

<210> SEQ ID NO 72
<211> LENGTH: 20
<212> TYPE: DNA
<213> ORGANISM: Human papillomavirus
```

```
<400> SEQUENCE: 72
gcgcagggcc acaataatgg                                           20

<210> SEQ ID NO 73
<211> LENGTH: 20
<212> TYPE: DNA
<213> ORGANISM: Human papillomavirus

<400> SEQUENCE: 73
gcacagggac ataataatgg                                           20

<210> SEQ ID NO 74
<211> LENGTH: 20
<212> TYPE: DNA
<213> ORGANISM: Human papillomavirus

<400> SEQUENCE: 74
gcccagggcc acaacaatgg                                           20

<210> SEQ ID NO 75
<211> LENGTH: 20
<212> TYPE: DNA
<213> ORGANISM: Human papillomavirus

<400> SEQUENCE: 75
gctcagggtt taaacaatgg                                           20

<210> SEQ ID NO 76
<211> LENGTH: 20
<212> TYPE: DNA
<213> ORGANISM: Human papillomavirus

<400> SEQUENCE: 76
gctcagggtt taaacaatgg                                           20

<210> SEQ ID NO 77
<211> LENGTH: 20
<212> TYPE: DNA
<213> ORGANISM: Human papillomavirus

<400> SEQUENCE: 77
gcccagggac ataacaatgg                                           20

<210> SEQ ID NO 78
<211> LENGTH: 20
<212> TYPE: DNA
<213> ORGANISM: Human papillomavirus

<400> SEQUENCE: 78
gctcagggac ataacaatgg                                           20

<210> SEQ ID NO 79
<211> LENGTH: 20
<212> TYPE: DNA
<213> ORGANISM: Human papillomavirus

<400> SEQUENCE: 79
gcccagggac acaataatgg                                           20

<210> SEQ ID NO 80
<211> LENGTH: 20
<212> TYPE: DNA
<213> ORGANISM: Human papillomavirus
```

-continued

```
<400> SEQUENCE: 80
gcacagggtc ataacaatgg                                          20

<210> SEQ ID NO 81
<211> LENGTH: 20
<212> TYPE: DNA
<213> ORGANISM: Human papillomavirus

<400> SEQUENCE: 81
gcacagggtc ataataatgg                                          20

<210> SEQ ID NO 82
<211> LENGTH: 20
<212> TYPE: DNA
<213> ORGANISM: Human papillomavirus

<400> SEQUENCE: 82
gcacagggac acaataatgg                                          20

<210> SEQ ID NO 83
<211> LENGTH: 20
<212> TYPE: DNA
<213> ORGANISM: Human papillomavirus

<400> SEQUENCE: 83
gctcagggac acaataatgg                                          20

<210> SEQ ID NO 84
<211> LENGTH: 20
<212> TYPE: DNA
<213> ORGANISM: Human papillomavirus

<400> SEQUENCE: 84
gcacaaggtc ataataatgg                                          20

<210> SEQ ID NO 85
<211> LENGTH: 20
<212> TYPE: DNA
<213> ORGANISM: Human papillomavirus

<400> SEQUENCE: 85
gcccagggac aaaacaatgg                                          20

<210> SEQ ID NO 86
<211> LENGTH: 20
<212> TYPE: DNA
<213> ORGANISM: Human papillomavirus

<400> SEQUENCE: 86
gcacaaggcc ataataatgg                                          20

<210> SEQ ID NO 87
<211> LENGTH: 20
<212> TYPE: DNA
<213> ORGANISM: Human papillomavirus

<400> SEQUENCE: 87
gcccagggcc acaacaatgg                                          20

<210> SEQ ID NO 88
<211> LENGTH: 20
<212> TYPE: DNA
<213> ORGANISM: Human papillomavirus
```

```
<400> SEQUENCE: 88
gcccagggcc ataacaatgg                                               20

<210> SEQ ID NO 89
<211> LENGTH: 20
<212> TYPE: DNA
<213> ORGANISM: Human papillomavirus

<400> SEQUENCE: 89
gcacaaggac acaataatgg                                               20

<210> SEQ ID NO 90
<211> LENGTH: 14
<212> TYPE: DNA
<213> ORGANISM: Human papillomavirus

<400> SEQUENCE: 90
ggacataata atgg                                                     14

<210> SEQ ID NO 91
<211> LENGTH: 20
<212> TYPE: DNA
<213> ORGANISM: Human papillomavirus

<400> SEQUENCE: 91
gcgcagggcc acaataatgg                                               20

<210> SEQ ID NO 92
<211> LENGTH: 20
<212> TYPE: DNA
<213> ORGANISM: Human papillomavirus

<400> SEQUENCE: 92
gcccagggcc ataacaatgg                                               20

<210> SEQ ID NO 93
<211> LENGTH: 20
<212> TYPE: DNA
<213> ORGANISM: Human papillomavirus

<400> SEQUENCE: 93
gcgcagggtc acaataatgg                                               20

<210> SEQ ID NO 94
<211> LENGTH: 20
<212> TYPE: DNA
<213> ORGANISM: Human papillomavirus

<400> SEQUENCE: 94
gcgcagggcc acaataatgg                                               20

<210> SEQ ID NO 95
<211> LENGTH: 20
<212> TYPE: DNA
<213> ORGANISM: Human papillomavirus

<400> SEQUENCE: 95
gcccagggac ataataatgg                                               20

<210> SEQ ID NO 96
<211> LENGTH: 20
<212> TYPE: DNA
<213> ORGANISM: Human papillomavirus
```

```
<400> SEQUENCE: 96
gcccagggtc aaaacaatgg                                               20

<210> SEQ ID NO 97
<211> LENGTH: 20
<212> TYPE: DNA
<213> ORGANISM: Human papillomavirus

<400> SEQUENCE: 97
gcgcagggcc acaataatgg                                               20

<210> SEQ ID NO 98
<211> LENGTH: 20
<212> TYPE: DNA
<213> ORGANISM: Human papillomavirus

<400> SEQUENCE: 98
gcccaaggcc ataataatgg                                               20

<210> SEQ ID NO 99
<211> LENGTH: 20
<212> TYPE: DNA
<213> ORGANISM: Human papillomavirus

<400> SEQUENCE: 99
gcacaaggtc ataacaatgg                                               20

<210> SEQ ID NO 100
<211> LENGTH: 20
<212> TYPE: DNA
<213> ORGANISM: Human papillomavirus

<400> SEQUENCE: 100
gctcagggtt taaacaatgg                                               20

<210> SEQ ID NO 101
<211> LENGTH: 20
<212> TYPE: DNA
<213> ORGANISM: Human papillomavirus

<400> SEQUENCE: 101
gcccagggcc acaacaatgg                                               20

<210> SEQ ID NO 102
<211> LENGTH: 20
<212> TYPE: DNA
<213> ORGANISM: Human papillomavirus

<400> SEQUENCE: 102
gcacagggtc ataataatgg                                               20

<210> SEQ ID NO 103
<211> LENGTH: 20
<212> TYPE: DNA
<213> ORGANISM: Human papillomavirus

<400> SEQUENCE: 103
gcacagggac ataacaatgg                                               20

<210> SEQ ID NO 104
<211> LENGTH: 20
<212> TYPE: DNA
<213> ORGANISM: Human papillomavirus
```

```
<400> SEQUENCE: 104
gcacagggtc ataataatgg                                              20

<210> SEQ ID NO 105
<211> LENGTH: 20
<212> TYPE: DNA
<213> ORGANISM: Human papillomavirus

<400> SEQUENCE: 105
gcccagggac ataacaatgg                                              20

<210> SEQ ID NO 106
<211> LENGTH: 20
<212> TYPE: DNA
<213> ORGANISM: Human papillomavirus

<400> SEQUENCE: 106
gcacagggac acaacaatgg                                              20

<210> SEQ ID NO 107
<211> LENGTH: 20
<212> TYPE: DNA
<213> ORGANISM: Human papillomavirus

<400> SEQUENCE: 107
gcacagggac ataacaatgg                                              20

<210> SEQ ID NO 108
<211> LENGTH: 20
<212> TYPE: DNA
<213> ORGANISM: Human papillomavirus

<400> SEQUENCE: 108
gcccagggaa ctaataatgg                                              20

<210> SEQ ID NO 109
<211> LENGTH: 20
<212> TYPE: DNA
<213> ORGANISM: Human papillomavirus

<400> SEQUENCE: 109
gcccagggtc ataataatgg                                              20

<210> SEQ ID NO 110
<211> LENGTH: 20
<212> TYPE: DNA
<213> ORGANISM: Human papillomavirus

<400> SEQUENCE: 110
gcacagggtc ataataatgg                                              20

<210> SEQ ID NO 111
<211> LENGTH: 20
<212> TYPE: DNA
<213> ORGANISM: Human papillomavirus

<400> SEQUENCE: 111
gcgcaaggcc acaataatgg                                              20

<210> SEQ ID NO 112
<211> LENGTH: 20
<212> TYPE: DNA
<213> ORGANISM: Human papillomavirus
```

```
<400> SEQUENCE: 112
gcacagggac ataataatgg                                              20

<210> SEQ ID NO 113
<211> LENGTH: 20
<212> TYPE: DNA
<213> ORGANISM: Human papillomavirus

<400> SEQUENCE: 113
gcccagggac ataataatgg                                              20

<210> SEQ ID NO 114
<211> LENGTH: 20
<212> TYPE: DNA
<213> ORGANISM: Human papillomavirus

<400> SEQUENCE: 114 gcgcgggtc ataacaatgg                                               20

<210> SEQ ID NO 115
<211> LENGTH: 20
<212> TYPE: DNA
<213> ORGANISM: Human papillomavirus

<400> SEQUENCE: 115
gcmcagggwc ataayaatgg                                              20

<210> SEQ ID NO 116
<211> LENGTH: 21
<212> TYPE: DNA
<213> ORGANISM: Human papillomavirus

<400> SEQUENCE: 116
gcgtgtagta tcaacaacag t                                            21

<210> SEQ ID NO 117
<211> LENGTH: 43
<212> TYPE: DNA
<213> ORGANISM: Human papillomavirus

<400> SEQUENCE: 117
ccttattggt tacaacgagc acaacaaata gttggttacc cca                    43

<210> SEQ ID NO 118
<211> LENGTH: 21
<212> TYPE: DNA
<213> ORGANISM: Human papillomavirus

<400> SEQUENCE: 118
ggtgaaaatg taccagacga t                                            21

<210> SEQ ID NO 119
<211> LENGTH: 44
<212> TYPE: DNA
<213> ORGANISM: Human papillomavirus

<400> SEQUENCE: 119
agaggtaacc atagaaccac tagggtctac tgcaaattta gcca                   44

<210> SEQ ID NO 120
<211> LENGTH: 19
<212> TYPE: DNA
<213> ORGANISM: Human papillomavirus
```

-continued

```
<400> SEQUENCE: 120
agtagatatg gcagcacat                                                  19

<210> SEQ ID NO 121
<211> LENGTH: 41
<212> TYPE: DNA
<213> ORGANISM: Human papillomavirus

<400> SEQUENCE: 121
acagggccac aataatggca tgacatattt gtactgcgtg t                         41

<210> SEQ ID NO 122
<211> LENGTH: 20
<212> TYPE: DNA
<213> ORGANISM: Human papillomavirus

<400> SEQUENCE: 122
cattaaaggc tctgggtcta                                                 20

<210> SEQ ID NO 123
<211> LENGTH: 44
<212> TYPE: DNA
<213> ORGANISM: Human papillomavirus

<400> SEQUENCE: 123
gcatcagagg taaccataga accactgcaa atttagccag ttca                      44

<210> SEQ ID NO 124
<211> LENGTH: 22
<212> TYPE: DNA
<213> ORGANISM: Human papillomavirus

<400> SEQUENCE: 124
ttccagtcct ccaaaatagt gg                                              22

<210> SEQ ID NO 125
<211> LENGTH: 48
<212> TYPE: DNA
<213> ORGANISM: Human papillomavirus

<400> SEQUENCE: 125
atactacacg cagtacaaat atgtctgtca taacgtctgc agttaagg                  48

<210> SEQ ID NO 126
<211> LENGTH: 25
<212> TYPE: DNA
<213> ORGANISM: Human papillomavirus

<400> SEQUENCE: 126
caaattattt tcctacacct agtgg                                           25

<210> SEQ ID NO 127
<211> LENGTH: 44
<212> TYPE: DNA
<213> ORGANISM: Human papillomavirus

<400> SEQUENCE: 127
gttggttacc ccaacaaatg cctctatggt tacctctgat gccc                      44

<210> SEQ ID NO 128
<211> LENGTH: 22
<212> TYPE: DNA
<213> ORGANISM: Human papillomavirus
```

```
<400> SEQUENCE: 128
gtcataacgt ctgcagttaa gg                                              22

<210> SEQ ID NO 129
<211> LENGTH: 24
<212> TYPE: DNA
<213> ORGANISM: Human papillomavirus

<400> SEQUENCE: 129
gtcgtaggta ctccttaaag ttag                                            24

<210> SEQ ID NO 130
<211> LENGTH: 46
<212> TYPE: DNA
<213> ORGANISM: Human papillomavirus

<400> SEQUENCE: 130
atactacacg cagtacaaat atgtctcccc atgtcgtagg tactcc                    46

<210> SEQ ID NO 131
<211> LENGTH: 43
<212> TYPE: DNA
<213> ORGANISM: Human papillomavirus

<400> SEQUENCE: 131
ctacacgcag tacaaatatg tctccccatg tcgtaggtac tcc                       43

<210> SEQ ID NO 132
<211> LENGTH: 40
<212> TYPE: DNA
<213> ORGANISM: Human papillomavirus

<400> SEQUENCE: 132
cacgcagtac aaatatgtca ccccatgtcg taggtactcc                           40

<210> SEQ ID NO 133
<211> LENGTH: 46
<212> TYPE: DNA
<213> ORGANISM: Human papillomavirus

<400> SEQUENCE: 133
ctacacgcag tacaaatatg tcgtagtttc tgaagtagat atggca                    46

<210> SEQ ID NO 134
<211> LENGTH: 46
<212> TYPE: DNA
<213> ORGANISM: Human papillomavirus

<400> SEQUENCE: 134
ctacacgcag tacaaatatg tctatgtagt ttctgaagta gatatg                    46

<210> SEQ ID NO 135
<211> LENGTH: 41
<212> TYPE: DNA
<213> ORGANISM: Human papillomavirus

<400> SEQUENCE: 135
gtggccctgt gctcgttgtt ctatggttac ctctgatgcc c                         41

<210> SEQ ID NO 136
<211> LENGTH: 39
<212> TYPE: DNA
<213> ORGANISM: Human papillomavirus
```

```
<400> SEQUENCE: 136
gtggccctgt gctcgttgtc tatggttacc tctgatgcc                    39

<210> SEQ ID NO 137
<211> LENGTH: 25
<212> TYPE: DNA
<213> ORGANISM: Human papillomavirus

<400> SEQUENCE: 137
gtgctgccat atctacttca gaaac                                   25

<210> SEQ ID NO 138
<211> LENGTH: 27
<212> TYPE: DNA
<213> ORGANISM: Human papillomavirus

<400> SEQUENCE: 138
gctgccatat ctacttcaga aactaca                                 27

<210> SEQ ID NO 139
<211> LENGTH: 25
<212> TYPE: DNA
<213> ORGANISM: Human papillomavirus

<400> SEQUENCE: 139
aaccaataag gtttattgaa tattt                                   25

<210> SEQ ID NO 140
<211> LENGTH: 25
<212> TYPE: DNA
<213> ORGANISM: Human papillomavirus

<400> SEQUENCE: 140
ccaataaggt ttattgaata tttgg                                   25

<210> SEQ ID NO 141
<211> LENGTH: 45
<212> TYPE: DNA
<213> ORGANISM: Human papillomavirus

<400> SEQUENCE: 141
ttatgcagca aatgcaggtg tggcccctat aggtggtttg caacc             45

<210> SEQ ID NO 142
<211> LENGTH: 20
<212> TYPE: DNA
<213> ORGANISM: Human papillomavirus

<400> SEQUENCE: 142
ccctataggt ggtttgcaac                                         20

<210> SEQ ID NO 143
<211> LENGTH: 20
<212> TYPE: DNA
<213> ORGANISM: Human papillomavirus

<400> SEQUENCE: 143
gtacatgggg atcctttgcc                                         20

<210> SEQ ID NO 144
<211> LENGTH: 52
<212> TYPE: DNA
<213> ORGANISM: Human papillomavirus
```

-continued

<400> SEQUENCE: 144
acagaaaatg ctagtgctta tgcagccaat tgtgtttgtt tgtaatccat ag    52

<210> SEQ ID NO 145
<211> LENGTH: 44
<212> TYPE: DNA
<213> ORGANISM: Human papillomavirus

<400> SEQUENCE: 145
cacagaaaat gctagtgctt attgtgtttg tttgtaatcc atag    44

<210> SEQ ID NO 146
<211> LENGTH: 45
<212> TYPE: DNA
<213> ORGANISM: Human papillomavirus

<400> SEQUENCE: 146
ataaaggatg gccactaatg cccgtgtagg tgttgaggta ggtcg    45

<210> SEQ ID NO 147
<211> LENGTH: 25
<212> TYPE: DNA
<213> ORGANISM: Human papillomavirus

<400> SEQUENCE: 147
cctgacacct cattttataa tccag    25

<210> SEQ ID NO 148
<211> LENGTH: 20
<212> TYPE: DNA
<213> ORGANISM: Human papillomavirus

<400> SEQUENCE: 148
atccagatac acagcggctg    20

<210> SEQ ID NO 149
<211> LENGTH: 38
<212> TYPE: DNA
<213> ORGANISM: Human papillomavirus

<400> SEQUENCE: 149
ccacacctaa tggctgacca cacacagcgg ctggtttg    38

<210> SEQ ID NO 150
<211> LENGTH: 40
<212> TYPE: DNA
<213> ORGANISM: Human papillomavirus

<400> SEQUENCE: 150
gccactaatg cccacaccta atgacacagc ggctggtttg    40

<210> SEQ ID NO 151
<211> LENGTH: 19
<212> TYPE: DNA
<213> ORGANISM: Human papillomavirus

<400> SEQUENCE: 151
ccaacagtac cagccctat    19

<210> SEQ ID NO 152
<211> LENGTH: 41
<212> TYPE: DNA
<213> ORGANISM: Human papillomavirus

```
<400> SEQUENCE: 152
tggtgtcaga accatatggc gacaaacatt tgttcccttc g            41

<210> SEQ ID NO 153
<211> LENGTH: 22
<212> TYPE: DNA
<213> ORGANISM: Human papillomavirus

<400> SEQUENCE: 153
cacagttatt caggatggtg at                                  22

<210> SEQ ID NO 154
<211> LENGTH: 43
<212> TYPE: DNA
<213> ORGANISM: Human papillomavirus

<400> SEQUENCE: 154
ggaacttcac ttttgttagc ctgttggttc atactggctt tgg           43

<210> SEQ ID NO 155
<211> LENGTH: 20
<212> TYPE: DNA
<213> ORGANISM: Human papillomavirus

<400> SEQUENCE: 155
ccctataggt ggtttgcaac                                     20

<210> SEQ ID NO 156
<211> LENGTH: 52
<212> TYPE: DNA
<213> ORGANISM: Human papillomavirus

<400> SEQUENCE: 156
acagaaaatg ctagtgctta tgcagccaat tgtgtttgtt tgtaatccat ag  52

<210> SEQ ID NO 157
<211> LENGTH: 25
<212> TYPE: DNA
<213> ORGANISM: Human papillomavirus

<400> SEQUENCE: 157
cctgacacct cattttataa tccag                               25

<210> SEQ ID NO 158
<211> LENGTH: 38
<212> TYPE: DNA
<213> ORGANISM: Human papillomavirus

<400> SEQUENCE: 158
ccacacctaa tggctgacca cacacagcgg ctggtttg                 38

<210> SEQ ID NO 159
<211> LENGTH: 40
<212> TYPE: DNA
<213> ORGANISM: Human papillomavirus

<400> SEQUENCE: 159
gccactaatg cccacaccta atgacacagc ggctggtttg               40

<210> SEQ ID NO 160
<211> LENGTH: 25
<212> TYPE: DNA
<213> ORGANISM: Human papillomavirus
```

```
<400> SEQUENCE: 160
aagttccaat cctctaaaat actgc                                           25

<210> SEQ ID NO 161
<211> LENGTH: 48
<212> TYPE: DNA
<213> ORGANISM: Human papillomavirus

<400> SEQUENCE: 161
accactcgca gtaccaattt aactgaatat aggacataac atctgcag                  48

<210> SEQ ID NO 162
<211> LENGTH: 21
<212> TYPE: DNA
<213> ORGANISM: Human papillomavirus

<400> SEQUENCE: 162
tgtattctcc ctctccaagt g                                               21

<210> SEQ ID NO 163
<211> LENGTH: 47
<212> TYPE: DNA
<213> ORGANISM: Human papillomavirus

<400> SEQUENCE: 163
taattgatta tgccagcaaa caccctctat tgttacctct gactccc                   47

<210> SEQ ID NO 164
<211> LENGTH: 43
<212> TYPE: DNA
<213> ORGANISM: Human papillomavirus

<400> SEQUENCE: 164
gccagcaaac accattgtta ctctattgtt acctctgact ccc                       43

<210> SEQ ID NO 165
<211> LENGTH: 45
<212> TYPE: DNA
<213> ORGANISM: Human papillomavirus

<400> SEQUENCE: 165
gccagcaaac accattgtta tgctctattg ttacctctga ctccc                     45

<210> SEQ ID NO 166
<211> LENGTH: 24
<212> TYPE: DNA
<213> ORGANISM: Human papillomavirus

<400> SEQUENCE: 166
gaatatagga cataacatct gcag                                            24

<210> SEQ ID NO 167
<211> LENGTH: 46
<212> TYPE: DNA
<213> ORGANISM: Human papillomavirus

<400> SEQUENCE: 167
accactcgca gtaccaattt aaccctcaac atgtctgcta tactgc                    46

<210> SEQ ID NO 168
<211> LENGTH: 45
<212> TYPE: DNA
<213> ORGANISM: Human papillomavirus
```

```
<400> SEQUENCE: 168
ccactcgcag taccaattta accctcaaca tgtctgctat actgc          45

<210> SEQ ID NO 169
<211> LENGTH: 43
<212> TYPE: DNA
<213> ORGANISM: Human papillomavirus

<400> SEQUENCE: 169
ccactcgcag taccaattta acctcaacat gtctgctata ctg            43

<210> SEQ ID NO 170
<211> LENGTH: 20
<212> TYPE: DNA
<213> ORGANISM: Human papillomavirus

<400> SEQUENCE: 170
accctgtgcc ttatgtaacc                                      20

<210> SEQ ID NO 171
<211> LENGTH: 48
<212> TYPE: DNA
<213> ORGANISM: Human papillomavirus

<400> SEQUENCE: 171
gatgacactg aaagttccca tgcgcccaaa atacataact gtgtctgc       48

<210> SEQ ID NO 172
<211> LENGTH: 47
<212> TYPE: DNA
<213> ORGANISM: Human papillomavirus

<400> SEQUENCE: 172
gatgacactg aaagttccca tgccccaaaa tacataactg tgtctgc        47

<210> SEQ ID NO 173
<211> LENGTH: 19
<212> TYPE: DNA
<213> ORGANISM: Human papillomavirus

<400> SEQUENCE: 173
agtgttcccc aatagcagg                                       19

<210> SEQ ID NO 174
<211> LENGTH: 20
<212> TYPE: DNA
<213> ORGANISM: Human papillomavirus

<400> SEQUENCE: 174
cagtgttccc caatagcagg                                      20

<210> SEQ ID NO 175
<211> LENGTH: 49
<212> TYPE: DNA
<213> ORGANISM: Human papillomavirus

<400> SEQUENCE: 175
gacactgaaa gttcccatgc cgctgtgtct gcttataatc tacagacac      49

<210> SEQ ID NO 176
<211> LENGTH: 44
<212> TYPE: DNA
<213> ORGANISM: Human papillomavirus
```

```
<400> SEQUENCE: 176
taaaatggat gcccactaag gcctgctgga gtggaaattg gccg                    44

<210> SEQ ID NO 177
<211> LENGTH: 21
<212> TYPE: DNA
<213> ORGANISM: Human papillomavirus

<400> SEQUENCE: 177
cctgaaacac aacgtttagt g                                            21

<210> SEQ ID NO 178
<211> LENGTH: 20
<212> TYPE: DNA
<213> ORGANISM: Human papillomavirus

<400> SEQUENCE: 178
cacaacgttt agtgtgggcc                                              20

<210> SEQ ID NO 179
<211> LENGTH: 27
<212> TYPE: DNA
<213> ORGANISM: Human papillomavirus

<400> SEQUENCE: 179
acctgatact agtatttata atcctga                                      27

<210> SEQ ID NO 180
<211> LENGTH: 38
<212> TYPE: DNA
<213> ORGANISM: Human papillomavirus

<400> SEQUENCE: 180
gatgcccact aaggccaaca cgcctgtgct ggagtgga                          38

<210> SEQ ID NO 181
<211> LENGTH: 43
<212> TYPE: DNA
<213> ORGANISM: Human papillomavirus

<400> SEQUENCE: 181
cactaaggcc aacacctaaa ggcaacacaa cgtttagtgt ggg                    43

<210> SEQ ID NO 182
<211> LENGTH: 19
<212> TYPE: DNA
<213> ORGANISM: Human papillomavirus

<400> SEQUENCE: 182
agtgttcccc aatagcagg                                               19

<210> SEQ ID NO 183
<211> LENGTH: 49
<212> TYPE: DNA
<213> ORGANISM: Human papillomavirus

<400> SEQUENCE: 183
gacactgaaa gttcccatgc cgctgtgtct gcttataatc tacagacac              49

<210> SEQ ID NO 184
<211> LENGTH: 21
<212> TYPE: DNA
<213> ORGANISM: Human papillomavirus
```

```
<400> SEQUENCE: 184
cctgaaacac aacgtttagt g                                        21

<210> SEQ ID NO 185
<211> LENGTH: 27
<212> TYPE: DNA
<213> ORGANISM: Human papillomavirus

<400> SEQUENCE: 185
acctgatact agtatttata atcctga                                  27

<210> SEQ ID NO 186
<211> LENGTH: 38
<212> TYPE: DNA
<213> ORGANISM: Human papillomavirus

<400> SEQUENCE: 186
gatgcccact aaggccaaca cgcctgtgct ggagtgga                      38

<210> SEQ ID NO 187
<211> LENGTH: 43
<212> TYPE: DNA
<213> ORGANISM: Human papillomavirus

<400> SEQUENCE: 187
cactaaggcc aacacctaaa ggcaacacaa cgtttagtgt ggg                43

<210> SEQ ID NO 188
<211> LENGTH: 25
<212> TYPE: DNA
<213> ORGANISM: Human papillomavirus

<400> SEQUENCE: 188
ccaatcttcc aaaatagcag gattc                                    25

<210> SEQ ID NO 189
<211> LENGTH: 51
<212> TYPE: DNA
<213> ORGANISM: Human papillomavirus

<400> SEQUENCE: 189
accacacgta gtaccaatat gtcctgtgaa tatatgtcat tatgtctgca g        51

<210> SEQ ID NO 190
<211> LENGTH: 21
<212> TYPE: DNA
<213> ORGANISM: Human papillomavirus

<400> SEQUENCE: 190
catactttcc tacacctagc g                                        21

<210> SEQ ID NO 191
<211> LENGTH: 46
<212> TYPE: DNA
<213> ORGANISM: Human papillomavirus

<400> SEQUENCE: 191
aactgattgc cccaacaaat accctccatg gttacttcag atgcac             46

<210> SEQ ID NO 192
<211> LENGTH: 45
<212> TYPE: DNA
<213> ORGANISM: Human papillomavirus
```

-continued

```
<400> SEQUENCE: 192
ccattattgt gtccctgagc acctccatgg ttacttcaga tgcac         45

<210> SEQ ID NO 193
<211> LENGTH: 41
<212> TYPE: DNA
<213> ORGANISM: Human papillomavirus

<400> SEQUENCE: 193
ctgattgccc caacaaatac ctccatggtt acttcagatg c             41

<210> SEQ ID NO 194
<211> LENGTH: 41
<212> TYPE: DNA
<213> ORGANISM: Human papillomavirus

<400> SEQUENCE: 194
ctgattgccc caacaaatac ccatggttac ttcagatgca c             41

<210> SEQ ID NO 195
<211> LENGTH: 26
<212> TYPE: DNA
<213> ORGANISM: Human papillomavirus

<400> SEQUENCE: 195
gtgaatatat gtcattatgt ctgcag                              26

<210> SEQ ID NO 196
<211> LENGTH: 47
<212> TYPE: DNA
<213> ORGANISM: Human papillomavirus

<400> SEQUENCE: 196
accacacgta gtaccaatat gtcttcctca ccatgtctta aatactc       47

<210> SEQ ID NO 197
<211> LENGTH: 48
<212> TYPE: DNA
<213> ORGANISM: Human papillomavirus

<400> SEQUENCE: 197
accacacgta gtaccaatat gtcattcctc accatgtctt aaatactc      48

<210> SEQ ID NO 198
<211> LENGTH: 48
<212> TYPE: DNA
<213> ORGANISM: Human papillomavirus

<400> SEQUENCE: 198
cacacgtagt accaatatgt ctgattcctc accatgtctt aaatactc      48

<210> SEQ ID NO 199
<211> LENGTH: 44
<212> TYPE: DNA
<213> ORGANISM: Human papillomavirus

<400> SEQUENCE: 199
ccacacgtag taccaatatg tccctcacca tgtcttaaat actc          44

<210> SEQ ID NO 200
<211> LENGTH: 43
<212> TYPE: DNA
<213> ORGANISM: Human papillomavirus
```

```
<400> SEQUENCE: 200
ccacacgtag taccaatatg tcctcaccat gtcttaaata ctc          43

<210> SEQ ID NO 201
<211> LENGTH: 20
<212> TYPE: DNA
<213> ORGANISM: Human papillomavirus

<400> SEQUENCE: 201
cacgttgcat ccaatatggt                                    20

<210> SEQ ID NO 202
<211> LENGTH: 19
<212> TYPE: DNA
<213> ORGANISM: Human papillomavirus

<400> SEQUENCE: 202
cacgttgcat ccaatatgg                                     19

<210> SEQ ID NO 203
<211> LENGTH: 51
<212> TYPE: DNA
<213> ORGANISM: Human papillomavirus

<400> SEQUENCE: 203
cactgaaaac tctaatagat atgccggtgc aaccaagtaa acacagttgt g  51

<210> SEQ ID NO 204
<211> LENGTH: 19
<212> TYPE: DNA
<213> ORGANISM: Human papillomavirus

<400> SEQUENCE: 204
ccaataggtg gtttgcaac                                     19

<210> SEQ ID NO 205
<211> LENGTH: 20
<212> TYPE: DNA
<213> ORGANISM: Human papillomavirus

<400> SEQUENCE: 205
cctttacccc aatgctctcc                                    20

<210> SEQ ID NO 206
<211> LENGTH: 52
<212> TYPE: DNA
<213> ORGANISM: Human papillomavirus

<400> SEQUENCE: 206
cactgaaaac tctaatagat atgccggagt tgtgtttgtt tataatccat tg  52

<210> SEQ ID NO 207
<211> LENGTH: 45
<212> TYPE: DNA
<213> ORGANISM: Human papillomavirus

<400> SEQUENCE: 207
ctgaaaactc taatagatat gcctgtgttt gtttataatc cattg         45

<210> SEQ ID NO 208
<211> LENGTH: 46
<212> TYPE: DNA
<213> ORGANISM: Human papillomavirus
```

```
<400> SEQUENCE: 208
ggatgaccac taatacctac accctgtgtt ggtttagagg taggtc            46

<210> SEQ ID NO 209
<211> LENGTH: 26
<212> TYPE: DNA
<213> ORGANISM: Human papillomavirus

<400> SEQUENCE: 209
tcctgataca tcttttata atcctg                                   26

<210> SEQ ID NO 210
<211> LENGTH: 21
<212> TYPE: DNA
<213> ORGANISM: Human papillomavirus

<400> SEQUENCE: 210
aactcaacgc ttagtttggg c                                       21

<210> SEQ ID NO 211
<211> LENGTH: 49
<212> TYPE: DNA
<213> ORGANISM: Human papillomavirus

<400> SEQUENCE: 211
ccactaatac ctacacctaa tggctgcaaa ctcaacgctt agtttgggc          49

<210> SEQ ID NO 212
<211> LENGTH: 41
<212> TYPE: DNA
<213> ORGANISM: Human papillomavirus

<400> SEQUENCE: 212
cactaatacc tacacctaat ggcctcaacg cttagtttgg g                 41

<210> SEQ ID NO 213
<211> LENGTH: 23
<212> TYPE: DNA
<213> ORGANISM: Human papillomavirus

<400> SEQUENCE: 213
gacctacctc taaaccaaca cag                                     23

<210> SEQ ID NO 214
<211> LENGTH: 16
<212> TYPE: DNA
<213> ORGANISM: Human papillomavirus

<400> SEQUENCE: 214
taatggctgc ccgcga                                             16

<210> SEQ ID NO 215
<211> LENGTH: 19
<212> TYPE: DNA
<213> ORGANISM: Human papillomavirus

<400> SEQUENCE: 215
ccaataggtg gtttgcaac                                          19

<210> SEQ ID NO 216
<211> LENGTH: 52
<212> TYPE: DNA
<213> ORGANISM: Human papillomavirus
```

-continued

```
<400> SEQUENCE: 216
cactgaaaac tctaatagat atgccggagt tgtgtttgtt tataatccat tg          52

<210> SEQ ID NO 217
<211> LENGTH: 26
<212> TYPE: DNA
<213> ORGANISM: Human papillomavirus

<400> SEQUENCE: 217
tcctgataca tcttttata atcctg                                        26

<210> SEQ ID NO 218
<211> LENGTH: 49
<212> TYPE: DNA
<213> ORGANISM: Human papillomavirus

<400> SEQUENCE: 218
ccactaatac ctacacctaa tggctgcaaa ctcaacgctt agtttgggc              49

<210> SEQ ID NO 219
<211> LENGTH: 22
<212> TYPE: DNA
<213> ORGANISM: Human papillomavirus

<400> SEQUENCE: 219
ggaggtgtta aaccaaattg cc                                           22

<210> SEQ ID NO 220
<211> LENGTH: 48
<212> TYPE: DNA
<213> ORGANISM: Human papillomavirus

<400> SEQUENCE: 220
accactcgca gtactaatat gactatgtca taacttctgc agttaagg               48

<210> SEQ ID NO 221
<211> LENGTH: 47
<212> TYPE: DNA
<213> ORGANISM: Human papillomavirus

<400> SEQUENCE: 221
accactcgca gtactaatat gaccttctgc agttaaggta actttgc                47

<210> SEQ ID NO 222
<211> LENGTH: 22
<212> TYPE: DNA
<213> ORGANISM: Human papillomavirus

<400> SEQUENCE: 222 gcttttttc ccactcctag tg                                            22

<210> SEQ ID NO 223
<211> LENGTH: 46
<212> TYPE: DNA
<213> ORGANISM: Human papillomavirus

<400> SEQUENCE: 223
cctgattgcc ccaacaaata ccgatcaatg gttacttccg aatctc                 46

<210> SEQ ID NO 224
<211> LENGTH: 44
<212> TYPE: DNA
<213> ORGANISM: Human papillomavirus
```

<400> SEQUENCE: 224
cctgattgcc ccaacaaata ccagccatat tggctacaac gtgc                     44

<210> SEQ ID NO 225
<211> LENGTH: 24
<212> TYPE: DNA
<213> ORGANISM: Human papillomavirus

<400> SEQUENCE: 225
atgtcataac ttctgcagtt aagg                                          24

<210> SEQ ID NO 226
<211> LENGTH: 47
<212> TYPE: DNA
<213> ORGANISM: Human papillomavirus

<400> SEQUENCE: 226
accactcgca gtactaatat gacttcttca acatgtctta tatattc                 47

<210> SEQ ID NO 227
<211> LENGTH: 47
<212> TYPE: DNA
<213> ORGANISM: Human papillomavirus

<400> SEQUENCE: 227
ataccactcg cagtactaat atgttcttca acatgtctta tatattc                 47

<210> SEQ ID NO 228
<211> LENGTH: 49
<212> TYPE: DNA
<213> ORGANISM: Human papillomavirus

<400> SEQUENCE: 228
accactcgca gtactaatat gacattcttc aacatgtctt atatattct               49

<210> SEQ ID NO 229
<211> LENGTH: 49
<212> TYPE: DNA
<213> ORGANISM: Human papillomavirus

<400> SEQUENCE: 229
ataccactcg cagtactaat atgattcttc aacatgtctt atatattct               49

<210> SEQ ID NO 230
<211> LENGTH: 38
<212> TYPE: DNA
<213> ORGANISM: Human papillomavirus

<400> SEQUENCE: 230
cctggacaac cgggtgctgt tggaggctta catccaag                           38

<210> SEQ ID NO 231
<211> LENGTH: 44
<212> TYPE: DNA
<213> ORGANISM: Human papillomavirus

<400> SEQUENCE: 231
tatcctggac aaccgggtgc tcctgttgga ggcttacatc caag                    44

<210> SEQ ID NO 232
<211> LENGTH: 22
<212> TYPE: DNA
<213> ORGANISM: Human papillomavirus

```
<400> SEQUENCE: 232
ggaggcttac atccaagtaa ac                                            22

<210> SEQ ID NO 233
<211> LENGTH: 22
<212> TYPE: DNA
<213> ORGANISM: Human papillomavirus

<400> SEQUENCE: 233
gtacaagcaa cacctttacc cc                                            22

<210> SEQ ID NO 234
<211> LENGTH: 50
<212> TYPE: DNA
<213> ORGANISM: Human papillomavirus

<400> SEQUENCE: 234
gacactgaaa ccggtaacaa gtatccactg tgtttgttta taatccatgg              50

<210> SEQ ID NO 235
<211> LENGTH: 46
<212> TYPE: DNA
<213> ORGANISM: Human papillomavirus

<400> SEQUENCE: 235
ggatgaccac ttatgccaac gccacaacga ttagtatggg catgtg                  46

<210> SEQ ID NO 236
<211> LENGTH: 24
<212> TYPE: DNA
<213> ORGANISM: Human papillomavirus

<400> SEQUENCE: 236
cctgacacct cctttataa ccct                                           24

<210> SEQ ID NO 237
<211> LENGTH: 23
<212> TYPE: DNA
<213> ORGANISM: Human papillomavirus

<400> SEQUENCE: 237
cctgacacct cctttataa ccc                                            23

<210> SEQ ID NO 238
<211> LENGTH: 45
<212> TYPE: DNA
<213> ORGANISM: Human papillomavirus

<400> SEQUENCE: 238
cacttatgcc aacgcctaat gggatacaca acgattagta tgggc                   45

<210> SEQ ID NO 239
<211> LENGTH: 43
<212> TYPE: DNA
<213> ORGANISM: Human papillomavirus

<400> SEQUENCE: 239
ggatgaccac ttatgccaac gcacaacgat tagtatgggc atg                     43

<210> SEQ ID NO 240
<211> LENGTH: 23
<212> TYPE: DNA
<213> ORGANISM: Human papillomavirus
```

```
<400> SEQUENCE: 240
gctgccctct acctatttca agg                                          23

<210> SEQ ID NO 241
<211> LENGTH: 20
<212> TYPE: DNA
<213> ORGANISM: Human papillomavirus

<400> SEQUENCE: 241
cacctttacc ccaatgttcc                                              20

<210> SEQ ID NO 242
<211> LENGTH: 22
<212> TYPE: DNA
<213> ORGANISM: Human papillomavirus

<400> SEQUENCE: 242
gtcatattag tactgcgagt gg                                           22

<210> SEQ ID NO 243
<211> LENGTH: 40
<212> TYPE: DNA
<213> ORGANISM: Human papillomavirus

<400> SEQUENCE: 243
ccgggtgctg ataataggga cctgttggag gcttacatcc                        40

<210> SEQ ID NO 244
<211> LENGTH: 38
<212> TYPE: DNA
<213> ORGANISM: Human papillomavirus

<400> SEQUENCE: 244
ccatattggc tacaacgtgc tacctgattg ccccaaca                          38

<210> SEQ ID NO 245
<211> LENGTH: 40
<212> TYPE: DNA
<213> ORGANISM: Human papillomavirus

<400> SEQUENCE: 245
ccatattggc tacaacgtgc accaaatacc tgattgcccc                        40

<210> SEQ ID NO 246
<211> LENGTH: 22
<212> TYPE: DNA
<213> ORGANISM: Human papillomavirus

<400> SEQUENCE: 246
gtgcacaagg tcataataat gg                                           22

<210> SEQ ID NO 247
<211> LENGTH: 19
<212> TYPE: DNA
<213> ORGANISM: Human papillomavirus

<400> SEQUENCE: 247
agtatgggca tgtgtaggc                                               19

<210> SEQ ID NO 248
<211> LENGTH: 20
<212> TYPE: DNA
<213> ORGANISM: Human papillomavirus
```

```
<210> SEQ ID NO 248
<211> LENGTH: 20
<212> TYPE: DNA
<213> ORGANISM: Human papillomavirus

<400> SEQUENCE: 248
agggctggta cattaggaga                                              20

<210> SEQ ID NO 249
<211> LENGTH: 19
<212> TYPE: DNA
<213> ORGANISM: Human papillomavirus

<400> SEQUENCE: 249
tgttcccgat gacctgtac                                               19

<210> SEQ ID NO 250
<211> LENGTH: 39
<212> TYPE: DNA
<213> ORGANISM: Human papillomavirus

<400> SEQUENCE: 250
cttgttaccg gtttcagtgt cagcagccat taggcgttg                         39

<210> SEQ ID NO 251
<211> LENGTH: 38
<212> TYPE: DNA
<213> ORGANISM: Human papillomavirus

<400> SEQUENCE: 251
gcactgcttt gaatagaggc actgttcccg atgacctg                          38

<210> SEQ ID NO 252
<211> LENGTH: 45
<212> TYPE: DNA
<213> ORGANISM: Human papillomavirus

<400> SEQUENCE: 252
gtaaccattg atccactagg agtgaaaggt tcaggaacta ctgcc                  45

<210> SEQ ID NO 253
<211> LENGTH: 26
<212> TYPE: DNA
<213> ORGANISM: Human papillomavirus

<400> SEQUENCE: 253
gtagttcctg aacctttaat gtacag                                       26

<210> SEQ ID NO 254
<211> LENGTH: 21
<212> TYPE: DNA
<213> ORGANISM: Human papillomavirus

<400> SEQUENCE: 254
gcactgcttt gaatagaggc a                                            21

<210> SEQ ID NO 255
<211> LENGTH: 27
<212> TYPE: DNA
<213> ORGANISM: Human papillomavirus

<400> SEQUENCE: 255
cagtagttcc tgaacctttta atgtaca                                     27

<210> SEQ ID NO 256
<211> LENGTH: 22
<212> TYPE: DNA
<213> ORGANISM: Human papillomavirus
```

```
<400> SEQUENCE: 256
ggaggcttac atccaagtaa ac                                            22

<210> SEQ ID NO 257
<211> LENGTH: 50
<212> TYPE: DNA
<213> ORGANISM: Human papillomavirus

<400> SEQUENCE: 257
gacactgaaa ccggtaacaa gtatccactg tgtttgttta taatccatgg              50

<210> SEQ ID NO 258
<211> LENGTH: 24
<212> TYPE: DNA
<213> ORGANISM: Human papillomavirus

<400> SEQUENCE: 258
cctgacacct cctttataa ccct                                           24

<210> SEQ ID NO 259
<211> LENGTH: 45
<212> TYPE: DNA
<213> ORGANISM: Human papillomavirus

<400> SEQUENCE: 259
cacttatgcc aacgcctaat gggatacaca acgattagta tgggc                   45

<210> SEQ ID NO 260
<211> LENGTH: 20
<212> TYPE: DNA
<213> ORGANISM: Human papillomavirus

<400> SEQUENCE: 260
caaatcctgt gtctaccatg                                               20

<210> SEQ ID NO 261
<211> LENGTH: 42
<212> TYPE: DNA
<213> ORGANISM: Human papillomavirus

<400> SEQUENCE: 261
ggcacacctt gtaatgctaa ctccccgtct tgtagtacag tg                      42

<210> SEQ ID NO 262
<211> LENGTH: 22
<212> TYPE: DNA
<213> ORGANISM: Human papillomavirus

<400> SEQUENCE: 262
atgttggtaa ctctggtaac tc                                            22

<210> SEQ ID NO 263
<211> LENGTH: 44
<212> TYPE: DNA
<213> ORGANISM: Human papillomavirus

<400> SEQUENCE: 263
ggaggcctac aacctattaa acaggtacag ataacaggga atgc                    44

<210> SEQ ID NO 264
<211> LENGTH: 25
<212> TYPE: DNA
<213> ORGANISM: Human papillomavirus
```

```
<400> SEQUENCE: 264
aattgtgttt gtttataatc catag                                          25

<210> SEQ ID NO 265
<211> LENGTH: 18
<212> TYPE: DNA
<213> ORGANISM: Human papillomavirus

<400> SEQUENCE: 265
tgcaccaaat cctgtgtc                                                  18

<210> SEQ ID NO 266
<211> LENGTH: 39
<212> TYPE: DNA
<213> ORGANISM: Human papillomavirus

<400> SEQUENCE: 266
gctaaccagg taaaagcagg ataccatgtc cccgtcttg                            39

<210> SEQ ID NO 267
<211> LENGTH: 22
<212> TYPE: DNA
<213> ORGANISM: Human papillomavirus

<400> SEQUENCE: 267
aactctggta actctggtac ag                                             22

<210> SEQ ID NO 268
<211> LENGTH: 44
<212> TYPE: DNA
<213> ORGANISM: Human papillomavirus

<400> SEQUENCE: 268
ggaggcctac aacctattaa acaacaggga atgcatttct atgg                      44

<210> SEQ ID NO 269
<211> LENGTH: 26
<212> TYPE: DNA
<213> ORGANISM: Human papillomavirus

<400> SEQUENCE: 269
caattgtgtt tgtttataat ccatag                                         26

<210> SEQ ID NO 270
<211> LENGTH: 20
<212> TYPE: DNA
<213> ORGANISM: Human papillomavirus

<400> SEQUENCE: 270
gatatttgca aatggaactg                                                20

<210> SEQ ID NO 271
<211> LENGTH: 41
<212> TYPE: DNA
<213> ORGANISM: Human papillomavirus

<400> SEQUENCE: 271
gacggggaca tggtagacac atatatctag gggaacatca c                         41

<210> SEQ ID NO 272
<211> LENGTH: 21
<212> TYPE: DNA
<213> ORGANISM: Human papillomavirus
```

-continued

<400> SEQUENCE: 272
gtgtttaata ggttgtaggc c    21

<210> SEQ ID NO 273
<211> LENGTH: 42
<212> TYPE: DNA
<213> ORGANISM: Human papillomavirus

<400> SEQUENCE: 273
ctcctgcttt tacctggtta gctcctatag gtgaacattg gg    42

<210> SEQ ID NO 274
<211> LENGTH: 20
<212> TYPE: DNA
<213> ORGANISM: Human papillomavirus

<400> SEQUENCE: 274
attacaaggt gtgccttttc    20

<210> SEQ ID NO 275
<211> LENGTH: 21
<212> TYPE: DNA
<213> ORGANISM: Human papillomavirus

<400> SEQUENCE: 275
ggatatttgc aaatggaact g    21

<210> SEQ ID NO 276
<211> LENGTH: 42
<212> TYPE: DNA
<213> ORGANISM: Human papillomavirus

<400> SEQUENCE: 276
gggacatggt agacacagga catatatcta ggggaacatc ac    42

<210> SEQ ID NO 277
<211> LENGTH: 19
<212> TYPE: DNA
<213> ORGANISM: Human papillomavirus

<400> SEQUENCE: 277
cctataggtg aacattggg    19

<210> SEQ ID NO 278
<211> LENGTH: 43
<212> TYPE: DNA
<213> ORGANISM: Human papillomavirus

<400> SEQUENCE: 278
gtttagtaac tccaaaggag gacaaaggca caccttgtaa tgc    43

<210> SEQ ID NO 279
<211> LENGTH: 20
<212> TYPE: DNA
<213> ORGANISM: Human papillomavirus

<400> SEQUENCE: 279
attctcctgc ttttacctgg    20

<210> SEQ ID NO 280
<211> LENGTH: 22
<212> TYPE: DNA
<213> ORGANISM: Human papillomavirus

```
<400> SEQUENCE: 280
cattctcctg cttttacctg gt                                              22

<210> SEQ ID NO 281
<211> LENGTH: 22
<212> TYPE: DNA
<213> ORGANISM: Human papillomavirus

<400> SEQUENCE: 281
atcctctaaa atggacgggt tc                                              22

<210> SEQ ID NO 282
<211> LENGTH: 50
<212> TYPE: DNA
<213> ORGANISM: Human papillomavirus

<400> SEQUENCE: 282
caacccgtag tacaaatatg tctgatatgt cataacatct gctgttagtg                50

<210> SEQ ID NO 283
<211> LENGTH: 25
<212> TYPE: DNA
<213> ORGANISM: Human papillomavirus

<400> SEQUENCE: 283
ctagttattt tcctactcct agtgg                                           25

<210> SEQ ID NO 284
<211> LENGTH: 47
<212> TYPE: DNA
<213> ORGANISM: Human papillomavirus

<400> SEQUENCE: 284
caattggtta ctccaacaaa taccctctat ggtaacctcc gatgcac                   47

<210> SEQ ID NO 285
<211> LENGTH: 46
<212> TYPE: DNA
<213> ORGANISM: Human papillomavirus

<400> SEQUENCE: 285
ccattattat ggccttgtgc acgctctatg gtaacctccg atgcac                    46

<210> SEQ ID NO 286
<211> LENGTH: 45
<212> TYPE: DNA
<213> ORGANISM: Human papillomavirus

<400> SEQUENCE: 286
atggccttgt gcacgttgca acctctatgg taacctccga tgcac                     45

<210> SEQ ID NO 287
<211> LENGTH: 38
<212> TYPE: DNA
<213> ORGANISM: Human papillomavirus

<400> SEQUENCE: 287
ggccttgtgc acgttgccta tggtaacctc cgatgcac                             38

<210> SEQ ID NO 288
<211> LENGTH: 38
<212> TYPE: DNA
<213> ORGANISM: Human papillomavirus
```

```
<400> SEQUENCE: 288
gccttgtgca cgttgcacta tggtaacctc cgatgcac                              38

<210> SEQ ID NO 289
<211> LENGTH: 24
<212> TYPE: DNA
<213> ORGANISM: Human papillomavirus

<400> SEQUENCE: 289
atgtcataac atctgctgtt agtg                                             24

<210> SEQ ID NO 290
<211> LENGTH: 24
<212> TYPE: DNA
<213> ORGANISM: Human papillomavirus

<400> SEQUENCE: 290
atgtcataac atctgctgtt agtg                                             24

<210> SEQ ID NO 291
<211> LENGTH: 49
<212> TYPE: DNA
<213> ORGANISM: Human papillomavirus

<400> SEQUENCE: 291
caacccgtag tacaaatatg tctgttcttc accatgcctt aaatattcc                  49

<210> SEQ ID NO 292
<211> LENGTH: 41
<212> TYPE: DNA
<213> ORGANISM: Human papillomavirus

<400> SEQUENCE: 292
cccgtagtac aaatatgtct gcaccatgcc ttaaatattc c                          41

<210> SEQ ID NO 293
<211> LENGTH: 43
<212> TYPE: DNA
<213> ORGANISM: Human papillomavirus

<400> SEQUENCE: 293
cccgtagtac aaatatgtct gttcaccatg ccttaaatat tcc                        43

<210> SEQ ID NO 294
<211> LENGTH: 44
<212> TYPE: DNA
<213> ORGANISM: Human papillomavirus

<400> SEQUENCE: 294
cccgtagtac aaatatgtct gcttcaccat gccttaaata ttcc                       44

<210> SEQ ID NO 295
<211> LENGTH: 24
<212> TYPE: DNA
<213> ORGANISM: Human papillomavirus

<400> SEQUENCE: 295
ccaatatggt ttattaaata tttg                                             24

<210> SEQ ID NO 296
<211> LENGTH: 25
<212> TYPE: DNA
<213> ORGANISM: Human papillomavirus
```

```
<400> SEQUENCE: 296
caatatggtt tattaaatat ttgtg                                    25

<210> SEQ ID NO 297
<211> LENGTH: 26
<212> TYPE: DNA
<213> ORGANISM: Human papillomavirus

<400> SEQUENCE: 297
caatatggtt tattaaatat ttgtgc                                   26

<210> SEQ ID NO 298
<211> LENGTH: 47
<212> TYPE: DNA
<213> ORGANISM: Human papillomavirus

<400> SEQUENCE: 298
gttggtaact ctggtaactc tggggaggcc tacaacctat taaacac            47

<210> SEQ ID NO 299
<211> LENGTH: 46
<212> TYPE: DNA
<213> ORGANISM: Human papillomavirus

<400> SEQUENCE: 299
gttggtaact ctggtaactc tgggaggcct acaacctatt aaacac             46

<210> SEQ ID NO 300
<211> LENGTH: 22
<212> TYPE: DNA
<213> ORGANISM: Human papillomavirus

<400> SEQUENCE: 300
cccaatgttc acctatagga gg                                       22

<210> SEQ ID NO 301
<211> LENGTH: 21
<212> TYPE: DNA
<213> ORGANISM: Human papillomavirus

<400> SEQUENCE: 301
gccttttccc caatgttcac c                                        21

<210> SEQ ID NO 302
<211> LENGTH: 52
<212> TYPE: DNA
<213> ORGANISM: Human papillomavirus

<400> SEQUENCE: 302
tggtaactct ggtaactctg gtacagccta caacctatta aacacaattg tg      52

<210> SEQ ID NO 303
<211> LENGTH: 45
<212> TYPE: DNA
<213> ORGANISM: Human papillomavirus

<400> SEQUENCE: 303
ggatgaccac taatacctac tccgtttggt ttgggcctgt acagg               45

<210> SEQ ID NO 304
<211> LENGTH: 44
<212> TYPE: DNA
<213> ORGANISM: Human papillomavirus
```

-continued

```
<400> SEQUENCE: 304
ggatgaccac taatacctac tccgtttggt ttgggcctgt acag        44

<210> SEQ ID NO 305
<211> LENGTH: 23
<212> TYPE: DNA
<213> ORGANISM: Human papillomavirus

<400> SEQUENCE: 305
ccagacacat cattttatga tcc        23

<210> SEQ ID NO 306
<211> LENGTH: 20
<212> TYPE: DNA
<213> ORGANISM: Human papillomavirus

<400> SEQUENCE: 306
ttatgatccc tgcctccagc        20

<210> SEQ ID NO 307
<211> LENGTH: 43
<212> TYPE: DNA
<213> ORGANISM: Human papillomavirus

<400> SEQUENCE: 307
gaccactaat acctactcct aatggcctgc ctccagcgtt tgg        43

<210> SEQ ID NO 308
<211> LENGTH: 18
<212> TYPE: DNA
<213> ORGANISM: Human papillomavirus

<400> SEQUENCE: 308
agcattacaa ggtgtgcc        18

<210> SEQ ID NO 309
<211> LENGTH: 43
<212> TYPE: DNA
<213> ORGANISM: Human papillomavirus

<400> SEQUENCE: 309
cagataacag ggaatgcatt tcaatgttca cctataggag gcc        43

<210> SEQ ID NO 310
<211> LENGTH: 18
<212> TYPE: DNA
<213> ORGANISM: Human papillomavirus

<400> SEQUENCE: 310
aagtaggtcg tggtcagc        18

<210> SEQ ID NO 311
<211> LENGTH: 46
<212> TYPE: DNA
<213> ORGANISM: Human papillomavirus

<400> SEQUENCE: 311
ccagagttac cagagttacc aacggagtag gtattagtgg tcatcc        46

<210> SEQ ID NO 312
<211> LENGTH: 24
<212> TYPE: DNA
<213> ORGANISM: Human papillomavirus
```

```
<400> SEQUENCE: 312
gattttcagt atcatccaat ttat                                          24

<210> SEQ ID NO 313
<211> LENGTH: 22
<212> TYPE: DNA
<213> ORGANISM: Human papillomavirus

<400> SEQUENCE: 313
cccaatgttc acctatagga gg                                            22

<210> SEQ ID NO 314
<211> LENGTH: 52
<212> TYPE: DNA
<213> ORGANISM: Human papillomavirus

<400> SEQUENCE: 314
tggtaactct ggtaactctg gtacagccta caacctatta aacacaattg tg           52

<210> SEQ ID NO 315
<211> LENGTH: 23
<212> TYPE: DNA
<213> ORGANISM: Human papillomavirus

<400> SEQUENCE: 315
ccagacacat cattttatga tcc                                           23

<210> SEQ ID NO 316
<211> LENGTH: 43
<212> TYPE: DNA
<213> ORGANISM: Human papillomavirus

<400> SEQUENCE: 316
gaccactaat acctactcct aatggcctgc ctccagcgtt tgg                     43

<210> SEQ ID NO 317
<211> LENGTH: 25
<212> TYPE: DNA
<213> ORGANISM: Human papillomavirus

<400> SEQUENCE: 317
ccaattgtcc aatatagagg aattc                                         25

<210> SEQ ID NO 318
<211> LENGTH: 49
<212> TYPE: DNA
<213> ORGANISM: Human papillomavirus

<400> SEQUENCE: 318
actacccgta gtaccaactt tacgacataa catcagttgt taatgtgac               49

<210> SEQ ID NO 319
<211> LENGTH: 21
<212> TYPE: DNA
<213> ORGANISM: Human papillomavirus

<400> SEQUENCE: 319
gttctgtata ctgcccctct c                                             21

<210> SEQ ID NO 320
<211> LENGTH: 46
<212> TYPE: DNA
<213> ORGANISM: Human papillomavirus
```

```
<400> SEQUENCE: 320
aacatatacc attgttgtgg cccttccatg gtaacctctg attccc            46

<210> SEQ ID NO 321
<211> LENGTH: 41
<212> TYPE: DNA
<213> ORGANISM: Human papillomavirus

<400> SEQUENCE: 321
gccttatgta gccaataagg cccagcggtt ccatggtaac c                 41

<210> SEQ ID NO 322
<211> LENGTH: 42
<212> TYPE: DNA
<213> ORGANISM: Human papillomavirus

<400> SEQUENCE: 322
gccttatgta gccaataagg cgcggttcca tggtaacctc tg                42

<210> SEQ ID NO 323
<211> LENGTH: 41
<212> TYPE: DNA
<213> ORGANISM: Human papillomavirus

<400> SEQUENCE: 323
gccaacatat accattgttg tcatggtaac ctctgattcc c                 41

<210> SEQ ID NO 324
<211> LENGTH: 26
<212> TYPE: DNA
<213> ORGANISM: Human papillomavirus

<400> SEQUENCE: 324
gacataacat cagttgttaa tgtgac                                  26

<210> SEQ ID NO 325
<211> LENGTH: 44
<212> TYPE: DNA
<213> ORGANISM: Human papillomavirus

<400> SEQUENCE: 325
actacccgta gtaccaactt tactccacgt gcctggtata ttcc              44

<210> SEQ ID NO 326
<211> LENGTH: 45
<212> TYPE: DNA
<213> ORGANISM: Human papillomavirus

<400> SEQUENCE: 326
actacccgta gtaccaactt tactccacgt gcctggtata ttcct             45

<210> SEQ ID NO 327
<211> LENGTH: 42
<212> TYPE: DNA
<213> ORGANISM: Human papillomavirus

<400> SEQUENCE: 327
ctacccgtag taccaacttt acccacgtgc ctggtatatt cc                42

<210> SEQ ID NO 328
<211> LENGTH: 20
<212> TYPE: DNA
<213> ORGANISM: Human papillomavirus
```

```
<400> SEQUENCE: 328
ccttatgtag ccaataaggc                                                     20

<210> SEQ ID NO 329
<211> LENGTH: 22
<212> TYPE: DNA
<213> ORGANISM: Human papillomavirus

<400> SEQUENCE: 329
ggccttatgt agccaataag gc                                                  22

<210> SEQ ID NO 330
<211> LENGTH: 45
<212> TYPE: DNA
<213> ORGANISM: Human papillomavirus

<400> SEQUENCE: 330
cagtagggat aatgtgtctg tggatgcctt tcccttaccc cagtg                         45

<210> SEQ ID NO 331
<211> LENGTH: 17
<212> TYPE: DNA
<213> ORGANISM: Human papillomavirus

<400> SEQUENCE: 331
aatggcggga acacagc                                                        17

<210> SEQ ID NO 332
<211> LENGTH: 24
<212> TYPE: DNA
<213> ORGANISM: Human papillomavirus

<400> SEQUENCE: 332
ccgtagatac attattgggc ttgc                                                24

<210> SEQ ID NO 333
<211> LENGTH: 52
<212> TYPE: DNA
<213> ORGANISM: Human papillomavirus

<400> SEQUENCE: 333
ctgaaaactc accattttca tcaacccaca actgtgtctg tttataatcc ac                 52

<210> SEQ ID NO 334
<211> LENGTH: 48
<212> TYPE: DNA
<213> ORGANISM: Human papillomavirus

<400> SEQUENCE: 334
ggtgagtttt cagtatcatc ctgtcccatt gggtgttggt attagtgg                      48

<210> SEQ ID NO 335
<211> LENGTH: 24
<212> TYPE: DNA
<213> ORGANISM: Human papillomavirus

<400> SEQUENCE: 335
ccagatgcat ccttatataa tcca                                                24

<210> SEQ ID NO 336
<211> LENGTH: 22
<212> TYPE: DNA
<213> ORGANISM: Human papillomavirus
```

```
<400> SEQUENCE: 336
gtttagtatg ggcttgtgta gg                                              22

<210> SEQ ID NO 337
<211> LENGTH: 47
<212> TYPE: DNA
<213> ORGANISM: Human papillomavirus

<400> SEQUENCE: 337
atgggtgtcc actaatacca acacgtttag tatgggcttg tgtaggg                   47

<210> SEQ ID NO 338
<211> LENGTH: 17
<212> TYPE: DNA
<213> ORGANISM: Human papillomavirus

<400> SEQUENCE: 338
aatggcggga acacagc                                                    17

<210> SEQ ID NO 339
<211> LENGTH: 52
<212> TYPE: DNA
<213> ORGANISM: Human papillomavirus

<400> SEQUENCE: 339
ctgaaaactc accattttca tcaacccaca actgtgtctg tttataatcc ac             52

<210> SEQ ID NO 340
<211> LENGTH: 24
<212> TYPE: DNA
<213> ORGANISM: Human papillomavirus

<400> SEQUENCE: 340
ccagatgcat ccttatataa tcca                                            24

<210> SEQ ID NO 341
<211> LENGTH: 47
<212> TYPE: DNA
<213> ORGANISM: Human papillomavirus

<400> SEQUENCE: 341
atgggtgtcc actaatacca acacgtttag tatgggcttg tgtaggg                   47

<210> SEQ ID NO 342
<211> LENGTH: 22
<212> TYPE: DNA
<213> ORGANISM: Human papillomavirus

<400> SEQUENCE: 342
tggtggaggg acaccaaaat tc                                              22

<210> SEQ ID NO 343
<211> LENGTH: 27
<212> TYPE: DNA
<213> ORGANISM: Human papillomavirus

<400> SEQUENCE: 343
ttccaatttt ctaatatact actattc                                         27

<210> SEQ ID NO 344
<211> LENGTH: 50
<212> TYPE: DNA
<213> ORGANISM: Human papillomavirus
```

-continued

```
<400> SEQUENCE: 344
cactacccgc agtactaatt taacatatga cataacctct gcagttaaag        50

<210> SEQ ID NO 345
<211> LENGTH: 48
<212> TYPE: DNA
<213> ORGANISM: Human papillomavirus

<400> SEQUENCE: 345
cactacccgc agtactaatt taacggatat atgacataac ctctgcag          48

<210> SEQ ID NO 346
<211> LENGTH: 48
<212> TYPE: DNA
<213> ORGANISM: Human papillomavirus

<400> SEQUENCE: 346
cactacccgc agtactaatt taaccctctg cagttaaagt aatagtgc          48

<210> SEQ ID NO 347
<211> LENGTH: 50
<212> TYPE: DNA
<213> ORGANISM: Human papillomavirus

<400> SEQUENCE: 347
cactacccgc agtactaatt taacctatgg atatatgaca taacctctgc        50

<210> SEQ ID NO 348
<211> LENGTH: 19
<212> TYPE: DNA
<213> ORGANISM: Human papillomavirus

<400> SEQUENCE: 348
tgtattcccc ttctcccag                                          19

<210> SEQ ID NO 349
<211> LENGTH: 19
<212> TYPE: DNA
<213> ORGANISM: Human papillomavirus

<400> SEQUENCE: 349
gtgaaacccc tggcagttg                                          19

<210> SEQ ID NO 350
<211> LENGTH: 48
<212> TYPE: DNA
<213> ORGANISM: Human papillomavirus

<400> SEQUENCE: 350
aaataccatt gttatggccc tggggctcta ttattacttc tgattctc          48

<210> SEQ ID NO 351
<211> LENGTH: 43
<212> TYPE: DNA
<213> ORGANISM: Human papillomavirus

<400> SEQUENCE: 351
ataccattgt tatggccctg ggtgtgtatt cccttctcc cag                43

<210> SEQ ID NO 352
<211> LENGTH: 43
<212> TYPE: DNA
<213> ORGANISM: Human papillomavirus
```

```
<400> SEQUENCE: 352
ataccattgt tatggccctg ggtgtattcc ccttctccca gtg                    43

<210> SEQ ID NO 353
<211> LENGTH: 47
<212> TYPE: DNA
<213> ORGANISM: Human papillomavirus

<400> SEQUENCE: 353
ataccattgt tatggccctg ggggctctat tattacttct gattctc                47

<210> SEQ ID NO 354
<211> LENGTH: 47
<212> TYPE: DNA
<213> ORGANISM: Human papillomavirus

<400> SEQUENCE: 354
caactgatta tgccaacaaa taccagccat attggttaca taaggcc                47

<210> SEQ ID NO 355
<211> LENGTH: 25
<212> TYPE: DNA
<213> ORGANISM: Human papillomavirus

<400> SEQUENCE: 355
tatgacataa cctctgcagt taaag                                        25

<210> SEQ ID NO 356
<211> LENGTH: 47
<212> TYPE: DNA
<213> ORGANISM: Human papillomavirus

<400> SEQUENCE: 356
cactacccgc agtactaatt taaccctcca catgtctact atactgc                47

<210> SEQ ID NO 357
<211> LENGTH: 49
<212> TYPE: DNA
<213> ORGANISM: Human papillomavirus

<400> SEQUENCE: 357
cactacccgc agtactaatt taacactata ctgcttaaac ttagtaggg              49

<210> SEQ ID NO 358
<211> LENGTH: 48
<212> TYPE: DNA
<213> ORGANISM: Human papillomavirus

<400> SEQUENCE: 358
ggatgataca gaaagtgctc atgccctaaa atacacagct gtgtttgc               48

<210> SEQ ID NO 359
<211> LENGTH: 41
<212> TYPE: DNA
<213> ORGANISM: Human papillomavirus

<400> SEQUENCE: 359
ggatgataca gaaagtgctc aaaatacaca gctgtgtttg c                      41

<210> SEQ ID NO 360
<211> LENGTH: 22
<212> TYPE: DNA
<213> ORGANISM: Human papillomavirus
```

```
<400> SEQUENCE: 360
caccaatagc aggtacacaa cc                                              22

<210> SEQ ID NO 361
<211> LENGTH: 21
<212> TYPE: DNA
<213> ORGANISM: Human papillomavirus

<400> SEQUENCE: 361
gtgctcacca atagcaggta c                                               21

<210> SEQ ID NO 362
<211> LENGTH: 52
<212> TYPE: DNA
<213> ORGANISM: Human papillomavirus

<400> SEQUENCE: 362
ggatgataca gaaagtgctc atgcagctgt tgcttataa tcaactgaca ca              52

<210> SEQ ID NO 363
<211> LENGTH: 45
<212> TYPE: DNA
<213> ORGANISM: Human papillomavirus

<400> SEQUENCE: 363
taaaatggat ggccacttag gccggtatgg aaattggtcg tgggc                     45

<210> SEQ ID NO 364
<211> LENGTH: 42
<212> TYPE: DNA
<213> ORGANISM: Human papillomavirus

<400> SEQUENCE: 364
ccacttaggc caatacctaa gtgtaggtat ggaaattggt cg                        42

<210> SEQ ID NO 365
<211> LENGTH: 21
<212> TYPE: DNA
<213> ORGANISM: Human papillomavirus

<400> SEQUENCE: 365
cctgaaacac aacgtttggt t                                               21

<210> SEQ ID NO 366
<211> LENGTH: 23
<212> TYPE: DNA
<213> ORGANISM: Human papillomavirus

<400> SEQUENCE: 366
gaaacacaac gtttggtttg ggc                                             23

<210> SEQ ID NO 367
<211> LENGTH: 46
<212> TYPE: DNA
<213> ORGANISM: Human papillomavirus

<400> SEQUENCE: 367
gccacttagg ccaataccta aggcatgtg taggtatgga aattgg                     46

<210> SEQ ID NO 368
<211> LENGTH: 44
<212> TYPE: DNA
<213> ORGANISM: Human papillomavirus
```

-continued

```
<400> SEQUENCE: 368
gccacttagg ccaataccta aagtgggcat gtgtaggtat ggaa         44

<210> SEQ ID NO 369
<211> LENGTH: 15
<212> TYPE: DNA
<213> ORGANISM: Human papillomavirus

<400> SEQUENCE: 369
aggctgccca cgacc                                         15

<210> SEQ ID NO 370
<211> LENGTH: 18
<212> TYPE: DNA
<213> ORGANISM: Human papillomavirus

<400> SEQUENCE: 370
caatacctaa aggctgcc                                      18

<210> SEQ ID NO 371
<211> LENGTH: 22
<212> TYPE: DNA
<213> ORGANISM: Human papillomavirus

<400> SEQUENCE: 371
caccaatagc aggtacacaa cc                                 22

<210> SEQ ID NO 372
<211> LENGTH: 52
<212> TYPE: DNA
<213> ORGANISM: Human papillomavirus

<400> SEQUENCE: 372
ggatgataca gaaagtgctc atgcagctgt ttgcttataa tcaactgaca ca    52

<210> SEQ ID NO 373
<211> LENGTH: 21
<212> TYPE: DNA
<213> ORGANISM: Human papillomavirus

<400> SEQUENCE: 373
cctgaaacac aacgtttggt t                                  21

<210> SEQ ID NO 374
<211> LENGTH: 46
<212> TYPE: DNA
<213> ORGANISM: Human papillomavirus

<400> SEQUENCE: 374
gccacttagg ccaataccta aaggcatgtg taggtatgga aattgg        46

<210> SEQ ID NO 375
<211> LENGTH: 44
<212> TYPE: DNA
<213> ORGANISM: Human papillomavirus

<400> SEQUENCE: 375
gccacttagg ccaataccta aagtgggcat gtgtaggtat ggaa         44

<210> SEQ ID NO 376
<211> LENGTH: 22
<212> TYPE: DNA
<213> ORGANISM: Human papillomavirus
```

```
<400> SEQUENCE: 376
ctgttcaaga atggtaggat cc                                              22

<210> SEQ ID NO 377
<211> LENGTH: 22
<212> TYPE: DNA
<213> ORGANISM: Human papillomavirus

<400> SEQUENCE: 377
tccactgttc aagaatggta gg                                              22

<210> SEQ ID NO 378
<211> LENGTH: 48
<212> TYPE: DNA
<213> ORGANISM: Human papillomavirus

<400> SEQUENCE: 378
taactattag cactgccact gcataagcca ttacctctgt agttaaag                  48

<210> SEQ ID NO 379
<211> LENGTH: 47
<212> TYPE: DNA
<213> ORGANISM: Human papillomavirus

<400> SEQUENCE: 379
taactattag cactgccact gcgtgtgtaa ataagccatt acctctg                   47

<210> SEQ ID NO 380
<211> LENGTH: 22
<212> TYPE: DNA
<213> ORGANISM: Human papillomavirus

<400> SEQUENCE: 380
atatactctg ctactcccag tg                                              22

<210> SEQ ID NO 381
<211> LENGTH: 20
<212> TYPE: DNA
<213> ORGANISM: Human papillomavirus

<400> SEQUENCE: 381
ggccgtgacc ctatagaaag                                                 20

<210> SEQ ID NO 382
<211> LENGTH: 46
<212> TYPE: DNA
<213> ORGANISM: Human papillomavirus

<400> SEQUENCE: 382
gctgattgtt ccagcaaatg ccggtctatg ataacatctg attctc                    46

<210> SEQ ID NO 383
<211> LENGTH: 44
<212> TYPE: DNA
<213> ORGANISM: Human papillomavirus

<400> SEQUENCE: 383
attattgtga ccctgcgcac ggatactctg ctactcccag tggg                      44

<210> SEQ ID NO 384
<211> LENGTH: 25
<212> TYPE: DNA
<213> ORGANISM: Human papillomavirus
```

```
<400> SEQUENCE: 384
taagccatta cctctgtagt taaag                                    25

<210> SEQ ID NO 385
<211> LENGTH: 45
<212> TYPE: DNA
<213> ORGANISM: Human papillomavirus

<400> SEQUENCE: 385
taactattag cactgccact gccttcccca tgcctaatat attgc               45

<210> SEQ ID NO 386
<211> LENGTH: 48
<212> TYPE: DNA
<213> ORGANISM: Human papillomavirus

<400> SEQUENCE: 386
atactaccag aagtacaaat ttaaccttcc ccatgcctaa tatattgc            48

<210> SEQ ID NO 387
<211> LENGTH: 47
<212> TYPE: DNA
<213> ORGANISM: Human papillomavirus

<400> SEQUENCE: 387
gcacaacaag atgttagaga taacacccaa taggtggagc acagcct             47

<210> SEQ ID NO 388
<211> LENGTH: 21
<212> TYPE: DNA
<213> ORGANISM: Human papillomavirus

<400> SEQUENCE: 388
ttgcatgtag tgccaatacc c                                        21

<210> SEQ ID NO 389
<211> LENGTH: 20
<212> TYPE: DNA
<213> ORGANISM: Human papillomavirus

<400> SEQUENCE: 389
gcatgtagtg ccaatacccc                                          20

<210> SEQ ID NO 390
<211> LENGTH: 46
<212> TYPE: DNA
<213> ORGANISM: Human papillomavirus

<400> SEQUENCE: 390
tgcacaacaa gatgttagag ataacacaat aggtggagca cagcct              46

<210> SEQ ID NO 391
<211> LENGTH: 42
<212> TYPE: DNA
<213> ORGANISM: Human papillomavirus

<400> SEQUENCE: 391
gcacaacaag atgttagaga taacaatagg tggagcacag cc                  42

<210> SEQ ID NO 392
<211> LENGTH: 40
<212> TYPE: DNA
<213> ORGANISM: Human papillomavirus
```

```
<400> SEQUENCE: 392
gcacaacaag atgttagaga taaataggtg gagcacagcc                              40

<210> SEQ ID NO 393
<211> LENGTH: 40
<212> TYPE: DNA
<213> ORGANISM: Human papillomavirus

<400> SEQUENCE: 393
gcacaacaag atgttagaga tcaataggtg gagcacagcc                              40

<210> SEQ ID NO 394
<211> LENGTH: 46
<212> TYPE: DNA
<213> ORGANISM: Human papillomavirus

<400> SEQUENCE: 394
tgctatgcgt gaattttctg tgtcttggtg ttggccttag tggtca                       46

<210> SEQ ID NO 395
<211> LENGTH: 19
<212> TYPE: DNA
<213> ORGANISM: Human papillomavirus

<400> SEQUENCE: 395
gttgaggtgg gcagaggac                                                     19

<210> SEQ ID NO 396
<211> LENGTH: 21
<212> TYPE: DNA
<213> ORGANISM: Human papillomavirus

<400> SEQUENCE: 396
ccagacacag ataggttggt g                                                  21

<210> SEQ ID NO 397
<211> LENGTH: 44
<212> TYPE: DNA
<213> ORGANISM: Human papillomavirus

<400> SEQUENCE: 397
ctatgcgtga attttctgtg tcatcccttg gtgttggcct tagt                         44

<210> SEQ ID NO 398
<211> LENGTH: 39
<212> TYPE: DNA
<213> ORGANISM: Human papillomavirus

<400> SEQUENCE: 398
ctatgcgtga attttctgtg cccttggtgt tggccttag                               39

<210> SEQ ID NO 399
<211> LENGTH: 40
<212> TYPE: DNA
<213> ORGANISM: Human papillomavirus

<400> SEQUENCE: 399
gctatgcgtg aattttctgt gcccttggtg ttggccttag                              40

<210> SEQ ID NO 400
<211> LENGTH: 25
<212> TYPE: DNA
<213> ORGANISM: Human papillomavirus
```

```
<400> SEQUENCE: 400
catcatattt attaaataag ggatg                                          25

<210> SEQ ID NO 401
<211> LENGTH: 22
<212> TYPE: DNA
<213> ORGANISM: Human papillomavirus

<400> SEQUENCE: 401
tttattaaat aagggatgac ca                                             22

<210> SEQ ID NO 402
<211> LENGTH: 27
<212> TYPE: DNA
<213> ORGANISM: Human papillomavirus

<400> SEQUENCE: 402
catatttatt aataaggga tgaccac                                         27

<210> SEQ ID NO 403
<211> LENGTH: 21
<212> TYPE: DNA
<213> ORGANISM: Human papillomavirus

<400> SEQUENCE: 403
ttgcatgtag tgccaatacc c                                              21

<210> SEQ ID NO 404
<211> LENGTH: 46
<212> TYPE: DNA
<213> ORGANISM: Human papillomavirus

<400> SEQUENCE: 404
tgcacaacaa gatgttagag ataacacaat aggtggagca cagcct                   46

<210> SEQ ID NO 405
<211> LENGTH: 19
<212> TYPE: DNA
<213> ORGANISM: Human papillomavirus

<400> SEQUENCE: 405
gttgaggtgg gcagaggac                                                 19

<210> SEQ ID NO 406
<211> LENGTH: 44
<212> TYPE: DNA
<213> ORGANISM: Human papillomavirus

<400> SEQUENCE: 406
ctatgcgtga attttctgtg tcatcccttg gtgttggcct tagt                     44

<210> SEQ ID NO 407
<211> LENGTH: 20
<212> TYPE: DNA
<213> ORGANISM: Human papillomavirus

<400> SEQUENCE: 407
cctcagcaca taaagtcatg                                                20

<210> SEQ ID NO 408
<211> LENGTH: 41
<212> TYPE: DNA
<213> ORGANISM: Human papillomavirus
```

<400> SEQUENCE: 408
gtactggtta caacgtgcgc agtggtatcc acaactgtga c                41

<210> SEQ ID NO 409
<211> LENGTH: 18
<212> TYPE: DNA
<213> ORGANISM: Human papillomavirus

<400> SEQUENCE: 409
gggtctaact ctggcaat                18

<210> SEQ ID NO 410
<211> LENGTH: 42
<212> TYPE: DNA
<213> ORGANISM: Human papillomavirus

<400> SEQUENCE: 410
ggattctgag gttaccatag aaccactgcc actgtacaaa gc                42

<210> SEQ ID NO 411
<211> LENGTH: 20
<212> TYPE: DNA
<213> ORGANISM: Human papillomavirus

<400> SEQUENCE: 411
cctcagcaca taaagtcatg                20

<210> SEQ ID NO 412
<211> LENGTH: 38
<212> TYPE: DNA
<213> ORGANISM: Human papillomavirus

<400> SEQUENCE: 412
cagggccaca ataatggcat acgagtggta tccacaac                38

<210> SEQ ID NO 413
<211> LENGTH: 18
<212> TYPE: DNA
<213> ORGANISM: Human papillomavirus

<400> SEQUENCE: 413
gggtctaact ctggcaat                18

<210> SEQ ID NO 414
<211> LENGTH: 42
<212> TYPE: DNA
<213> ORGANISM: Human papillomavirus

<400> SEQUENCE: 414
ggattctgag gttaccatag aaccactgcc actgtacaaa gc                42

<210> SEQ ID NO 415
<211> LENGTH: 22
<212> TYPE: DNA
<213> ORGANISM: Human papillomavirus

<400> SEQUENCE: 415
gtcctctaaa atagtggcat cc                22

<210> SEQ ID NO 416
<211> LENGTH: 19
<212> TYPE: DNA
<213> ORGANISM: Human papillomavirus -continued

```
<400> SEQUENCE: 416
ggggtaaggc caaattgcc                                                    19

<210> SEQ ID NO 417
<211> LENGTH: 48
<212> TYPE: DNA
<213> ORGANISM: Human papillomavirus

<400> SEQUENCE: 417
ccactcgtag cactaacatg acgtatgtca taacatcagc tgttaatg                    48

<210> SEQ ID NO 418
<211> LENGTH: 45
<212> TYPE: DNA
<213> ORGANISM: Human papillomavirus

<400> SEQUENCE: 418
ccactcgtag cactaacatg accctctaaa atagtggcat ccatc                       45

<210> SEQ ID NO 419
<211> LENGTH: 23
<212> TYPE: DNA
<213> ORGANISM: Human papillomavirus

<400> SEQUENCE: 419 gcttttttc ctactcctag tgg                                                23

<210> SEQ ID NO 420
<211> LENGTH: 20
<212> TYPE: DNA
<213> ORGANISM: Human papillomavirus

<400> SEQUENCE: 420
gccactgtac aaagcagtgc                                                   20

<210> SEQ ID NO 421
<211> LENGTH: 45
<212> TYPE: DNA
<213> ORGANISM: Human papillomavirus

<400> SEQUENCE: 421
actgattgcc ccaacatatg ccttctatgg taacctcaga atccc                       45

<210> SEQ ID NO 422
<211> LENGTH: 44
<212> TYPE: DNA
<213> ORGANISM: Human papillomavirus

<400> SEQUENCE: 422
attattgtgg ccctgcgcac gttctatggt aacctcagaa tccc                        44

<210> SEQ ID NO 423
<211> LENGTH: 38
<212> TYPE: DNA
<213> ORGANISM: Human papillomavirus

<400> SEQUENCE: 423
ccctgcgcac gttgtaacta tggtaacctc agaatccc                               38

<210> SEQ ID NO 424
<211> LENGTH: 42
<212> TYPE: DNA
<213> ORGANISM: Human papillomavirus
```

```
<400> SEQUENCE: 424
ccaacatatg ccattattgt gctatggtaa cctcagaatc cc                    42

<210> SEQ ID NO 425
<211> LENGTH: 45
<212> TYPE: DNA
<213> ORGANISM: Human papillomavirus

<400> SEQUENCE: 425
accactcgta gcactaacat gactcgccat gacgaaggta ttcct                 45

<210> SEQ ID NO 426
<211> LENGTH: 39
<212> TYPE: DNA
<213> ORGANISM: Human papillomavirus

<400> SEQUENCE: 426
ccactcgtag cactaacatg gccatgacga aggtattcc                        39

<210> SEQ ID NO 427
<211> LENGTH: 41
<212> TYPE: DNA
<213> ORGANISM: Human papillomavirus

<400> SEQUENCE: 427
ccactcgtag cactaacatg acgccatgac gaaggtattc c                     41

<210> SEQ ID NO 428
<211> LENGTH: 26
<212> TYPE: DNA
<213> ORGANISM: Human papillomavirus

<400> SEQUENCE: 428
gtatgtcata acatcagctg ttaatg                                      26

<210> SEQ ID NO 429
<211> LENGTH: 25
<212> TYPE: DNA
<213> ORGANISM: Human papillomavirus

<400> SEQUENCE: 429
tgaatgtatg tcataacatc agctg                                       25

<210> SEQ ID NO 430
<211> LENGTH: 43
<212> TYPE: DNA
<213> ORGANISM: Human papillomavirus

<400> SEQUENCE: 430
ccactcgtag cactaacatg actcgccatg acgaaggtat tcc                   43

<210> SEQ ID NO 431
<211> LENGTH: 24
<212> TYPE: DNA
<213> ORGANISM: Human papillomavirus

<400> SEQUENCE: 431
gctgaggtta aaaggaaag caca                                         24

<210> SEQ ID NO 432
<211> LENGTH: 26
<212> TYPE: DNA
<213> ORGANISM: Human papillomavirus
```

```
<400> SEQUENCE: 432
gactttatgt gctgaggtta aaaagg                                        26

<210> SEQ ID NO 433
<211> LENGTH: 28
<212> TYPE: DNA
<213> ORGANISM: Human papillomavirus

<400> SEQUENCE: 433
ctttatgtgc tgaggttaaa aggaaag                                       28

<210> SEQ ID NO 434
<211> LENGTH: 23
<212> TYPE: DNA
<213> ORGANISM: Human papillomavirus

<400> SEQUENCE: 434
ccagtacggt ttattaaata att                                           23

<210> SEQ ID NO 435
<211> LENGTH: 20
<212> TYPE: DNA
<213> ORGANISM: Human papillomavirus

<400> SEQUENCE: 435
gcgcacgttg taaccagtac                                               20

<210> SEQ ID NO 436
<211> LENGTH: 27
<212> TYPE: DNA
<213> ORGANISM: Human papillomavirus

<400> SEQUENCE: 436
gttgtaacca gtacggttta ttaaata                                       27

<210> SEQ ID NO 437
<211> LENGTH: 27
<212> TYPE: DNA
<213> ORGANISM: Human papillomavirus

<400> SEQUENCE: 437
cgttgtaacc agtacggttt attaaat                                       27

<210> SEQ ID NO 438
<211> LENGTH: 22
<212> TYPE: DNA
<213> ORGANISM: Human papillomavirus

<400> SEQUENCE: 438
cacctatagg aggtttgcat cc                                            22

<210> SEQ ID NO 439
<211> LENGTH: 53
<212> TYPE: DNA
<213> ORGANISM: Human papillomavirus

<400> SEQUENCE: 439
tgatactgaa accagtaaca aatatgctaa ctgagtctgc ttataatcca tag          53

<210> SEQ ID NO 440
<211> LENGTH: 25
<212> TYPE: DNA
<213> ORGANISM: Human papillomavirus
```

```
<400> SEQUENCE: 440
ccagatacat ctttttataa cccag                                    25

<210> SEQ ID NO 441
<211> LENGTH: 43
<212> TYPE: DNA
<213> ORGANISM: Human papillomavirus

<400> SEQUENCE: 441
aaaggatgcc cactaatacc cacaaaaccc aaaggttggt gtg                 43

<210> SEQ ID NO 442
<211> LENGTH: 20
<212> TYPE: DNA
<213> ORGANISM: Human papillomavirus

<400> SEQUENCE: 442
cctcagcaca taaagtcatg                                          20

<210> SEQ ID NO 443
<211> LENGTH: 40
<212> TYPE: DNA
<213> ORGANISM: Human papillomavirus

<400> SEQUENCE: 443
cagggccaca ataatggcat agtggtatcc acaactgtga                    40

<210> SEQ ID NO 444
<211> LENGTH: 18
<212> TYPE: DNA
<213> ORGANISM: Human papillomavirus

<400> SEQUENCE: 444
gccactgtac aaagcagt                                            18

<210> SEQ ID NO 445
<211> LENGTH: 42
<212> TYPE: DNA
<213> ORGANISM: Human papillomavirus

<400> SEQUENCE: 445
cacgttgtaa ccagtacggt ttttcctact cctagtggtt ct                 42

<210> SEQ ID NO 446
<211> LENGTH: 22
<212> TYPE: DNA
<213> ORGANISM: Human papillomavirus

<400> SEQUENCE: 446
cacctatagg aggtttgcat cc                                       22

<210> SEQ ID NO 447
<211> LENGTH: 53
<212> TYPE: DNA
<213> ORGANISM: Human papillomavirus

<400> SEQUENCE: 447
tgatactgaa accagtaaca aatatgctaa ctgagtctgc ttataatcca tag     53

<210> SEQ ID NO 448
<211> LENGTH: 25
<212> TYPE: DNA
<213> ORGANISM: Human papillomavirus
```

```
<400> SEQUENCE: 448
ccagatacat ctttttataa cccag                                          25

<210> SEQ ID NO 449
<211> LENGTH: 43
<212> TYPE: DNA
<213> ORGANISM: Human papillomavirus

<400> SEQUENCE: 449
aaaggatgcc cactaatacc cacaaaaccc aaaggttggt gtg                      43

<210> SEQ ID NO 450
<211> LENGTH: 22
<212> TYPE: DNA
<213> ORGANISM: Human papillomavirus

<400> SEQUENCE: 450
gtcctccagt aggttagcat tc                                             22

<210> SEQ ID NO 451
<211> LENGTH: 49
<212> TYPE: DNA
<213> ORGANISM: Human papillomavirus

<400> SEQUENCE: 451
agtactaaca tgactattag tactgctgcc ataacctctg cagacaaag                49

<210> SEQ ID NO 452
<211> LENGTH: 48
<212> TYPE: DNA
<213> ORGANISM: Human papillomavirus

<400> SEQUENCE: 452
atactactag aagtactaac atgactgcca taacctctgc agacaaag                 48

<210> SEQ ID NO 453
<211> LENGTH: 22
<212> TYPE: DNA
<213> ORGANISM: Human papillomavirus

<400> SEQUENCE: 453
gtatatgttg ctacgcctag tg                                             22

<210> SEQ ID NO 454
<211> LENGTH: 46
<212> TYPE: DNA
<213> ORGANISM: Human papillomavirus

<400> SEQUENCE: 454
aattgattac cccagcaaat gccgtctatg attacgtctg aggcac                   46

<210> SEQ ID NO 455
<211> LENGTH: 41
<212> TYPE: DNA
<213> ORGANISM: Human papillomavirus

<400> SEQUENCE: 455
ccccagcaaa tgccattatt ctatgattac gtctgaggca c                        41

<210> SEQ ID NO 456
<211> LENGTH: 22
<212> TYPE: DNA
<213> ORGANISM: Human papillomavirus
```

```
<400> SEQUENCE: 456
gccataacct ctgcagacaa ag                                              22

<210> SEQ ID NO 457
<211> LENGTH: 47
<212> TYPE: DNA
<213> ORGANISM: Human papillomavirus

<400> SEQUENCE: 457
atactactag aagtactaac atgaccctcc acatgtctaa ggtactg                   47

<210> SEQ ID NO 458
<211> LENGTH: 20
<212> TYPE: DNA
<213> ORGANISM: Human papillomavirus

<400> SEQUENCE: 458
gcacgttgca accaataagg                                                 20

<210> SEQ ID NO 459
<211> LENGTH: 46
<212> TYPE: DNA
<213> ORGANISM: Human papillomavirus

<400> SEQUENCE: 459
ggctggatga tactgaaagt tcccacaact gtgtttgctt gccatc                    46

<210> SEQ ID NO 460
<211> LENGTH: 19
<212> TYPE: DNA
<213> ORGANISM: Human papillomavirus

<400> SEQUENCE: 460
tccaatgttc acccatagc                                                  19

<210> SEQ ID NO 461
<211> LENGTH: 20
<212> TYPE: DNA
<213> ORGANISM: Human papillomavirus

<400> SEQUENCE: 461
ccaatgttca cccatagcgg                                                 20

<210> SEQ ID NO 462
<211> LENGTH: 47
<212> TYPE: DNA
<213> ORGANISM: Human papillomavirus

<400> SEQUENCE: 462
ggatgatact gaaagttcca atttagccac aactgtgttt gcttgcc                   47

<210> SEQ ID NO 463
<211> LENGTH: 45
<212> TYPE: DNA
<213> ORGANISM: Human papillomavirus

<400> SEQUENCE: 463
aaacaatgga tggccactta gccatgtgta ggtttggagg taggc                     45

<210> SEQ ID NO 464
<211> LENGTH: 21
<212> TYPE: DNA
<213> ORGANISM: Human papillomavirus
```

-continued

```
<400> SEQUENCE: 464
ttataatccg gaccaggaac g                                              21

<210> SEQ ID NO 465
<211> LENGTH: 20
<212> TYPE: DNA
<213> ORGANISM: Human papillomavirus

<400> SEQUENCE: 465
ataatccgga ccaggaacgg                                                20

<210> SEQ ID NO 466
<211> LENGTH: 44
<212> TYPE: DNA
<213> ORGANISM: Human papillomavirus

<400> SEQUENCE: 466
acaatggatg gccacttagc cgcatgtgta ggtttggagg tagg                     44

<210> SEQ ID NO 467
<211> LENGTH: 47
<212> TYPE: DNA
<213> ORGANISM: Human papillomavirus

<400> SEQUENCE: 467
ggatgatact gaaagttcca atttagccac aactgtgttt gcttgcc                  47

<210> SEQ ID NO 468
<211> LENGTH: 21
<212> TYPE: DNA
<213> ORGANISM: Human papillomavirus

<400> SEQUENCE: 468
ttataatccg gaccaggaac g                                              21

<210> SEQ ID NO 469
<211> LENGTH: 44
<212> TYPE: DNA
<213> ORGANISM: Human papillomavirus

<400> SEQUENCE: 469
acaatggatg gccacttagc cgcatgtgta ggtttggagg tagg                     44

<210> SEQ ID NO 470
<211> LENGTH: 19
<212> TYPE: DNA
<213> ORGANISM: Human papillomavirus

<400> SEQUENCE: 470
tccaatgttc acccatagc                                                 19

<210> SEQ ID NO 471
<211> LENGTH: 20
<212> TYPE: DNA
<213> ORGANISM: Human papillomavirus

<400> SEQUENCE: 471
caaagtccat gcatccaaac                                                20

<210> SEQ ID NO 472
<211> LENGTH: 41
<212> TYPE: DNA
<213> ORGANISM: Human papillomavirus
```

```
<400> SEQUENCE: 472
gcctgtaaca ataatgcagc tgcaccatgt caccatcctc a                    41

<210> SEQ ID NO 473
<211> LENGTH: 18
<212> TYPE: DNA
<213> ORGANISM: Human papillomavirus

<400> SEQUENCE: 473
aacagatatc ccgcacag                                              18

<210> SEQ ID NO 474
<211> LENGTH: 42
<212> TYPE: DNA
<213> ORGANISM: Human papillomavirus

<400> SEQUENCE: 474
gtgggaggtt tacagccaat taggtctgat aacagggaat gc                   42

<210> SEQ ID NO 475
<211> LENGTH: 20
<212> TYPE: DNA
<213> ORGANISM: Human papillomavirus

<400> SEQUENCE: 475
ccattgttat gaccttgtgc                                            20

<210> SEQ ID NO 476
<211> LENGTH: 41
<212> TYPE: DNA
<213> ORGANISM: Human papillomavirus

<400> SEQUENCE: 476
tccaactcct agtggctcta tagcgctgta gccaataagg c                    41

<210> SEQ ID NO 477
<211> LENGTH: 19
<212> TYPE: DNA
<213> ORGANISM: Human papillomavirus

<400> SEQUENCE: 477
gacgtgagca gatgtttgt                                             19

<210> SEQ ID NO 478
<211> LENGTH: 42
<212> TYPE: DNA
<213> ORGANISM: Human papillomavirus

<400> SEQUENCE: 478
ggataactgc agtattaccg gacctagggc tggaaaactt gg                   42

<210> SEQ ID NO 479
<211> LENGTH: 32
<212> TYPE: DNA
<213> ORGANISM: Human papillomavirus

<400> SEQUENCE: 479
gttacctcag aatcacaatt atttaataag cc                              32

<210> SEQ ID NO 480
<211> LENGTH: 28
<212> TYPE: DNA
<213> ORGANISM: Human papillomavirus
```

```
<400> SEQUENCE: 480
cctcagaatc acaattattt aataagcc                                      28

<210> SEQ ID NO 481
<211> LENGTH: 24
<212> TYPE: DNA
<213> ORGANISM: Human papillomavirus

<400> SEQUENCE: 481
cagtcctcca aaatattgga atcc                                          24

<210> SEQ ID NO 482
<211> LENGTH: 20
<212> TYPE: DNA
<213> ORGANISM: Human papillomavirus

<400> SEQUENCE: 482
aaccaaattg ccagtcctcc                                               20

<210> SEQ ID NO 483
<211> LENGTH: 50
<212> TYPE: DNA
<213> ORGANISM: Human papillomavirus

<400> SEQUENCE: 483
taccactcgt agcactaata tgacatatgt cattatctct gcagttagtg              50

<210> SEQ ID NO 484
<211> LENGTH: 48
<212> TYPE: DNA
<213> ORGANISM: Human papillomavirus

<400> SEQUENCE: 484
accactcgta gcactaatat gactatgtca ttatctctgc agttagtg                48

<210> SEQ ID NO 485
<211> LENGTH: 49
<212> TYPE: DNA
<213> ORGANISM: Human papillomavirus

<400> SEQUENCE: 485
accactcgta gcactaatat gacatatgtc attatctctg cagttagtg               49

<210> SEQ ID NO 486
<211> LENGTH: 49
<212> TYPE: DNA
<213> ORGANISM: Human papillomavirus

<400> SEQUENCE: 486
accactcgta gcactaatat gacgcagtta gtgtaatttt gcaaagctg               49

<210> SEQ ID NO 487
<211> LENGTH: 50
<212> TYPE: DNA
<213> ORGANISM: Human papillomavirus

<400> SEQUENCE: 487
taccactcgt agcactaata tgacgcagtt agtgtaatttt tgcaaagctg             50

<210> SEQ ID NO 488
<211> LENGTH: 25
<212> TYPE: DNA
<213> ORGANISM: Human papillomavirus
```

```
<400> SEQUENCE: 488
gtagtgcatt ttttccaact cctag                                          25

<210> SEQ ID NO 489
<211> LENGTH: 22
<212> TYPE: DNA
<213> ORGANISM: Human papillomavirus

<400> SEQUENCE: 489
ctgcagttat ccaaagtagt gc                                             22

<210> SEQ ID NO 490
<211> LENGTH: 45
<212> TYPE: DNA
<213> ORGANISM: Human papillomavirus

<400> SEQUENCE: 490
ctgattgccc cagcaaatgc cgctctatag ttacctcaga atcac                    45

<210> SEQ ID NO 491
<211> LENGTH: 42
<212> TYPE: DNA
<213> ORGANISM: Human papillomavirus

<400> SEQUENCE: 491
ctgattgccc cagcaaatgc cttggctaca gcgtgcacaa gg                       42

<210> SEQ ID NO 492
<211> LENGTH: 45
<212> TYPE: DNA
<213> ORGANISM: Human papillomavirus

<400> SEQUENCE: 492
ctgattgccc cagcaaatgc cggctctata gttacctcag aatca                    45

<210> SEQ ID NO 493
<211> LENGTH: 24
<212> TYPE: DNA
<213> ORGANISM: Human papillomavirus

<400> SEQUENCE: 493
atgtcattat ctctgcagtt agtg                                           24

<210> SEQ ID NO 494
<211> LENGTH: 48
<212> TYPE: DNA
<213> ORGANISM: Human papillomavirus

<400> SEQUENCE: 494
accactcgta gcactaatat gacttcttca acatgacgta catattcc                 48

<210> SEQ ID NO 495
<211> LENGTH: 20
<212> TYPE: DNA
<213> ORGANISM: Human papillomavirus

<400> SEQUENCE: 495
ctcaccagtg ggaggtttac                                                20

<210> SEQ ID NO 496
<211> LENGTH: 48
<212> TYPE: DNA
<213> ORGANISM: Human papillomavirus
```

<210> SEQ ID NO 496

<400> SEQUENCE: 496
ctgaaaccag taacagatat cccggccaat taaacataat tgtgtttg     48

<210> SEQ ID NO 497
<211> LENGTH: 44
<212> TYPE: DNA
<213> ORGANISM: Human papillomavirus

<400> SEQUENCE: 497
tgaaaccagt aacagatatc cgtccatag ataagcattc cctg     44

<210> SEQ ID NO 498
<211> LENGTH: 44
<212> TYPE: DNA
<213> ORGANISM: Human papillomavirus

<400> SEQUENCE: 498
tgaaaccagt aacagatatc cgaatccat agataagcat tccc     44

<210> SEQ ID NO 499
<211> LENGTH: 22
<212> TYPE: DNA
<213> ORGANISM: Human papillomavirus

<400> SEQUENCE: 499
taaccctgat acacaacgtt tg     22

<210> SEQ ID NO 500
<211> LENGTH: 43
<212> TYPE: DNA
<213> ORGANISM: Human papillomavirus

<400> SEQUENCE: 500
aggatgacca cttacgccaa cactctgggc atgtgtaggc ctt     43

<210> SEQ ID NO 501
<211> LENGTH: 20
<212> TYPE: DNA
<213> ORGANISM: Human papillomavirus

<400> SEQUENCE: 501
caatggctgt cccctaccta     20

<210> SEQ ID NO 502
<211> LENGTH: 22
<212> TYPE: DNA
<213> ORGANISM: Human papillomavirus

<400> SEQUENCE: 502
atggctgtcc cctacctatt tc     22

<210> SEQ ID NO 503
<211> LENGTH: 19
<212> TYPE: DNA
<213> ORGANISM: Human papillomavirus

<400> SEQUENCE: 503
cctttacccc aatgctcac     19

<210> SEQ ID NO 504
<211> LENGTH: 39
<212> TYPE: DNA
<213> ORGANISM: Human papillomavirus

```
<400> SEQUENCE: 504
agccagggtc tgataacagg gggaggttta cagccaatt          39

<210> SEQ ID NO 505
<211> LENGTH: 18
<212> TYPE: DNA
<213> ORGANISM: Human papillomavirus

<400> SEQUENCE: 505
aataggtagg ggacagcc                                 18

<210> SEQ ID NO 506
<211> LENGTH: 42
<212> TYPE: DNA
<213> ORGANISM: Human papillomavirus

<400> SEQUENCE: 506
gcgggatatc tgttactggt ttcagcgtaa gtggtcatcc tt      42

<210> SEQ ID NO 507
<211> LENGTH: 20
<212> TYPE: DNA
<213> ORGANISM: Human papillomavirus

<400> SEQUENCE: 507
ctcaccagtg ggaggtttac                               20

<210> SEQ ID NO 508
<211> LENGTH: 48
<212> TYPE: DNA
<213> ORGANISM: Human papillomavirus

<400> SEQUENCE: 508
ctgaaaccag taacagatat cccggccaat taaacataat tgtgtttg  48

<210> SEQ ID NO 509
<211> LENGTH: 22
<212> TYPE: DNA
<213> ORGANISM: Human papillomavirus

<400> SEQUENCE: 509
taaccctgat acacaacgtt tg                            22

<210> SEQ ID NO 510
<211> LENGTH: 43
<212> TYPE: DNA
<213> ORGANISM: Human papillomavirus

<400> SEQUENCE: 510
aggatgacca cttacgccaa cactctgggc atgtgtaggc ctt     43

<210> SEQ ID NO 511
<211> LENGTH: 25
<212> TYPE: DNA
<213> ORGANISM: Human papillomavirus

<400> SEQUENCE: 511
ccaatcctcc aaaatagtgg tattc                         25

<210> SEQ ID NO 512
<211> LENGTH: 48
<212> TYPE: DNA
<213> ORGANISM: Human papillomavirus
```

```
<400> SEQUENCE: 512
ctactcgcag caccaatctt tcgtatgaca ttacctctgt agttaatg        48

<210> SEQ ID NO 513
<211> LENGTH: 46
<212> TYPE: DNA
<213> ORGANISM: Human papillomavirus

<400> SEQUENCE: 513
ctactcgcag caccaatctt tcgaatgtat gacattacct ctgtag          46

<210> SEQ ID NO 514
<211> LENGTH: 47
<212> TYPE: DNA
<213> ORGANISM: Human papillomavirus

<400> SEQUENCE: 514
ctactcgcag caccaatctt tctgaatgta tgacattacc tctgtag         47

<210> SEQ ID NO 515
<211> LENGTH: 49
<212> TYPE: DNA
<213> ORGANISM: Human papillomavirus

<400> SEQUENCE: 515
acaattgatt gtgccaacat ataccggtct gtggttactt ctgattcac       49

<210> SEQ ID NO 516
<211> LENGTH: 21
<212> TYPE: DNA
<213> ORGANISM: Human papillomavirus

<400> SEQUENCE: 516
tatattcccc ttccccaagt g                                      21

<210> SEQ ID NO 517
<211> LENGTH: 48
<212> TYPE: DNA
<213> ORGANISM: Human papillomavirus

<400> SEQUENCE: 517
caattgattg tgccaacata taccggtctg tggttacttc tgattcac        48

<210> SEQ ID NO 518
<211> LENGTH: 46
<212> TYPE: DNA
<213> ORGANISM: Human papillomavirus

<400> SEQUENCE: 518
ttaaaccctg agccttgtgc agggtctgtg gttacttctg attcac          46

<210> SEQ ID NO 519
<211> LENGTH: 26
<212> TYPE: DNA
<213> ORGANISM: Human papillomavirus

<400> SEQUENCE: 519
gtatgacatt acctctgtag ttaatg                                 26

<210> SEQ ID NO 520
<211> LENGTH: 24
<212> TYPE: DNA
<213> ORGANISM: Human papillomavirus
```

<400> SEQUENCE: 520
gaatgtatga cattacctct gtag                                    24

<210> SEQ ID NO 521
<211> LENGTH: 25
<212> TYPE: DNA
<213> ORGANISM: Human papillomavirus

<400> SEQUENCE: 521
tgaatgtatg acattacctc tgtag                                   25

<210> SEQ ID NO 522
<211> LENGTH: 44
<212> TYPE: DNA
<213> ORGANISM: Human papillomavirus

<400> SEQUENCE: 522
ctactcgcag caccaatctt tccctccaca tgtctggcat attc               44

<210> SEQ ID NO 523
<211> LENGTH: 24
<212> TYPE: DNA
<213> ORGANISM: Human papillomavirus

<400> SEQUENCE: 523
gcaggtacac agccaataat acac                                    24

<210> SEQ ID NO 524
<211> LENGTH: 50
<212> TYPE: DNA
<213> ORGANISM: Human papillomavirus

<400> SEQUENCE: 524
gatgacactg aaaactctca tgtagcgctg agtttgttta taatccacag         50

<210> SEQ ID NO 525
<211> LENGTH: 45
<212> TYPE: DNA
<213> ORGANISM: Human papillomavirus

<400> SEQUENCE: 525
gatgacactg aaaactctca tgctgagttt gtttataatc cacag              45

<210> SEQ ID NO 526
<211> LENGTH: 27
<212> TYPE: DNA
<213> ORGANISM: Human papillomavirus

<400> SEQUENCE: 526
ccagataaca cagtatatga tcctaac                                 27

<210> SEQ ID NO 527
<211> LENGTH: 43
<212> TYPE: DNA
<213> ORGANISM: Human papillomavirus

<400> SEQUENCE: 527
cactgagtcc taccccctaaa ggttgtctca acgcttggtc tgg               43

<210> SEQ ID NO 528
<211> LENGTH: 40
<212> TYPE: DNA
<213> ORGANISM: Human papillomavirus

```
<400> SEQUENCE: 528
cactgagtcc taccccctaaa ggtctcaacg cttggtctgg                           40

<210> SEQ ID NO 529
<211> LENGTH: 25
<212> TYPE: DNA
<213> ORGANISM: Human papillomavirus

<400> SEQUENCE: 529
gctgttgata ccaaagatac acgtg                                           25

<210> SEQ ID NO 530
<211> LENGTH: 27
<212> TYPE: DNA
<213> ORGANISM: Human papillomavirus

<400> SEQUENCE: 530
ctgttgatac caaagataca cgtgata                                         27

<210> SEQ ID NO 531
<211> LENGTH: 25
<212> TYPE: DNA
<213> ORGANISM: Human papillomavirus

<400> SEQUENCE: 531
gataccaaag atacacgtga taatg                                           25

<210> SEQ ID NO 532
<211> LENGTH: 26
<212> TYPE: DNA
<213> ORGANISM: Human papillomavirus

<400> SEQUENCE: 532
gcatctgctg ttgataccaa agatac                                          26

<210> SEQ ID NO 533
<211> LENGTH: 21
<212> TYPE: DNA
<213> ORGANISM: Human papillomavirus

<400> SEQUENCE: 533
gatttcaaca cctacacagg c                                               21

<210> SEQ ID NO 534
<211> LENGTH: 24
<212> TYPE: DNA
<213> ORGANISM: Human papillomavirus

<400> SEQUENCE: 534
gcaggtacac agccaataat acac                                            24

<210> SEQ ID NO 535
<211> LENGTH: 50
<212> TYPE: DNA
<213> ORGANISM: Human papillomavirus

<400> SEQUENCE: 535
gatgacactg aaaactctca tgtagcgctg agtttgttta taatccacag                50

<210> SEQ ID NO 536
<211> LENGTH: 27
<212> TYPE: DNA
<213> ORGANISM: Human papillomavirus
```

-continued

<400> SEQUENCE: 536
ccagataaca cagtatatga tcctaac                                    27

<210> SEQ ID NO 537
<211> LENGTH: 43
<212> TYPE: DNA
<213> ORGANISM: Human papillomavirus

<400> SEQUENCE: 537
cactgagtcc taccccctaaa ggttgtctca acgcttggtc tgg                 43

<210> SEQ ID NO 538
<211> LENGTH: 18
<212> TYPE: DNA
<213> ORGANISM: Human papillomavirus

<400> SEQUENCE: 538
gtgccttgtg cagccaat                                              18

<210> SEQ ID NO 539
<211> LENGTH: 50
<212> TYPE: DNA
<213> ORGANISM: Human papillomavirus

<400> SEQUENCE: 539
gtagttatgt atatgcccccc tcgccgcttg ttaaataact gggagtctga          50

<210> SEQ ID NO 540
<211> LENGTH: 24
<212> TYPE: DNA
<213> ORGANISM: Human papillomavirus

<400> SEQUENCE: 540
acgtagggaa cagttatttg ctag                                       24

<210> SEQ ID NO 541
<211> LENGTH: 44
<212> TYPE: DNA
<213> ORGANISM: Human papillomavirus

<400> SEQUENCE: 541
tgtcacgtat gtcagtgccc ttaatggaat agagggggca tggt                 44

<210> SEQ ID NO 542
<211> LENGTH: 18
<212> TYPE: DNA
<213> ORGANISM: Human papillomavirus

<400> SEQUENCE: 542
aatggcagga acacagcc                                              18

<210> SEQ ID NO 543
<211> LENGTH: 50
<212> TYPE: DNA
<213> ORGANISM: Human papillomavirus

<400> SEQUENCE: 543
tgaaaattcc ccgttttcct ccaacgcgtt tgtttatagt ccactgaaac           50

<210> SEQ ID NO 544
<211> LENGTH: 21
<212> TYPE: DNA
<213> ORGANISM: Human papillomavirus

```
<400> SEQUENCE: 544
tgatacgcag cgattggtat g                                          21

<210> SEQ ID NO 545
<211> LENGTH: 39
<212> TYPE: DNA
<213> ORGANISM: Human papillomavirus

<400> SEQUENCE: 545
tgcccactaa ggccaacacc ggcctgtgtt ggtgttgaa                        39

<210> SEQ ID NO 546
<211> LENGTH: 25
<212> TYPE: DNA
<213> ORGANISM: Human papillomavirus

<400> SEQUENCE: 546
gttaaataac tgggagtctg aggat                                      25

<210> SEQ ID NO 547
<211> LENGTH: 44
<212> TYPE: DNA
<213> ORGANISM: Human papillomavirus

<400> SEQUENCE: 547
taagggcact gacatacgtg acagccatag acccactagg cgag                  44

<210> SEQ ID NO 548
<211> LENGTH: 24
<212> TYPE: DNA
<213> ORGANISM: Human papillomavirus

<400> SEQUENCE: 548
ctgcagatgt atatggagac agta                                       24

<210> SEQ ID NO 549
<211> LENGTH: 42
<212> TYPE: DNA
<213> ORGANISM: Human papillomavirus

<400> SEQUENCE: 549
agtgtcccct accatgcccc acgtagggaa cagttatttg ct                   42

<210> SEQ ID NO 550
<211> LENGTH: 18
<212> TYPE: DNA
<213> ORGANISM: Human papillomavirus

<400> SEQUENCE: 550
tgtgtccctg tgccttgt                                              18

<210> SEQ ID NO 551
<211> LENGTH: 44
<212> TYPE: DNA
<213> ORGANISM: Human papillomavirus

<400> SEQUENCE: 551
gtagttatgt atatgccccc tcgccgcagc caatagggct tgtt                  44

<210> SEQ ID NO 552
<211> LENGTH: 54
<212> TYPE: DNA
<213> ORGANISM: Human papillomavirus
```

```
<400> SEQUENCE: 552
cgcagtacca attttacttt gtctactact acctcaacat gcctaatata ttcc    54

<210> SEQ ID NO 553
<211> LENGTH: 23
<212> TYPE: DNA
<213> ORGANISM: Human papillomavirus

<400> SEQUENCE: 553
actgacatac gtgacagtcc tag                                      23

<210> SEQ ID NO 554
<211> LENGTH: 48
<212> TYPE: DNA
<213> ORGANISM: Human papillomavirus

<400> SEQUENCE: 554
gattatgcca acaaatacca ttgttgttcc cagttattta acaagccc           48

<210> SEQ ID NO 555
<211> LENGTH: 47
<212> TYPE: DNA
<213> ORGANISM: Human papillomavirus

<400> SEQUENCE: 555
cagtaagaaa taattgatta tgccaacaaa caagccctat tggctgc            47

<210> SEQ ID NO 556
<211> LENGTH: 49
<212> TYPE: DNA
<213> ORGANISM: Human papillomavirus

<400> SEQUENCE: 556
ccactcgcag taccaatttt actttgcctc aacatgccta atatattcc          49

<210> SEQ ID NO 557
<211> LENGTH: 48
<212> TYPE: DNA
<213> ORGANISM: Human papillomavirus

<400> SEQUENCE: 557
ataccactcg cagtaccaat tttaccctca acatgcctaa tatattcc           48

<210> SEQ ID NO 558
<211> LENGTH: 24
<212> TYPE: DNA
<213> ORGANISM: Human papillomavirus

<400> SEQUENCE: 558
tcagtggaca atgttatagt acac                                     24

<210> SEQ ID NO 559
<211> LENGTH: 49
<212> TYPE: DNA
<213> ORGANISM: Human papillomavirus

<400> SEQUENCE: 559
ccactcgcag tacaaatttt actttgcctc aacatgccta atatattcc          49

<210> SEQ ID NO 560
<211> LENGTH: 48
<212> TYPE: DNA
<213> ORGANISM: Human papillomavirus
```

<400> SEQUENCE: 560
ataccactcg cagtacaaat tttaccctca acatgcctaa tatattcc    48

<210> SEQ ID NO 561
<211> LENGTH: 26
<212> TYPE: DNA
<213> ORGANISM: Human papillomavirus

<400> SEQUENCE: 561
catcagtgga taatgttata gtacac    26

<210> SEQ ID NO 562
<211> LENGTH: 48
<212> TYPE: DNA
<213> ORGANISM: Human papillomavirus

<400> SEQUENCE: 562
gcgcagtact aattttacat tgtccctca acatgcctaa catattcc    48

<210> SEQ ID NO 563
<211> LENGTH: 48
<212> TYPE: DNA
<213> ORGANISM: Human papillomavirus

<400> SEQUENCE: 563
atacaacgcg cagtactaat tttaccctca acatgcctaa catattcc    48

<210> SEQ ID NO 564
<211> LENGTH: 20
<212> TYPE: DNA
<213> ORGANISM: Human papillomavirus

<400> SEQUENCE: 564
gatttacctt tggcccagtg    20

<210> SEQ ID NO 565
<211> LENGTH: 49
<212> TYPE: DNA
<213> ORGANISM: Human papillomavirus

<400> SEQUENCE: 565
tagatgatac tgaaaattcc ccgttgccta taatacatag ttgcgtttg    49

<210> SEQ ID NO 566
<211> LENGTH: 26
<212> TYPE: DNA
<213> ORGANISM: Human papillomavirus

<400> SEQUENCE: 566
cctgagtcta cattatataa ccctga    26

<210> SEQ ID NO 567
<211> LENGTH: 42
<212> TYPE: DNA
<213> ORGANISM: Human papillomavirus

<400> SEQUENCE: 567
cccactaagg ccaacaccta atgtacgcag cgattggtat gg    42

<210> SEQ ID NO 568
<211> LENGTH: 25
<212> TYPE: DNA
<213> ORGANISM: Human papillomavirus

```
<400> SEQUENCE: 568
cagctgattc agtagtagta gacaa                                           25

<210> SEQ ID NO 569
<211> LENGTH: 43
<212> TYPE: DNA
<213> ORGANISM: Human papillomavirus

<400> SEQUENCE: 569
ggcacaggga cacaacaatg gtaaattggt actgcgagtg gta                       43

<210> SEQ ID NO 570
<211> LENGTH: 22
<212> TYPE: DNA
<213> ORGANISM: Human papillomavirus

<400> SEQUENCE: 570
tgacatacgt gacagtccta gt                                              22

<210> SEQ ID NO 571
<211> LENGTH: 44
<212> TYPE: DNA
<213> ORGANISM: Human papillomavirus

<400> SEQUENCE: 571
ttgtgcagcc aatagggctt gttaagtata tgccccctcg ccta                      44

<210> SEQ ID NO 572
<211> LENGTH: 23
<212> TYPE: DNA
<213> ORGANISM: Human papillomavirus

<400> SEQUENCE: 572
ctctattcca aaaatgccta gca                                             23

<210> SEQ ID NO 573
<211> LENGTH: 26
<212> TYPE: DNA
<213> ORGANISM: Human papillomavirus

<400> SEQUENCE: 573
cctagtagtt atgtatatgc cccctc                                          26

<210> SEQ ID NO 574
<211> LENGTH: 27
<212> TYPE: DNA
<213> ORGANISM: Human papillomavirus

<400> SEQUENCE: 574
tacaattcag taggtatagt gtccct                                          27

<210> SEQ ID NO 575
<211> LENGTH: 25
<212> TYPE: DNA
<213> ORGANISM: Human papillomavirus

<400> SEQUENCE: 575
gtgggtctat ggtatcctca gactc                                           25

<210> SEQ ID NO 576
<211> LENGTH: 52
<212> TYPE: DNA
<213> ORGANISM: Human papillomavirus
```

-continued

<210> SEQ ID NO 577
<211> LENGTH: 50
<212> TYPE: DNA
<213> ORGANISM: Human papillomavirus

<400> SEQUENCE: 576
ccactcgcag taccaattt actttgcatc agtggacaat gttatagtac ac    52

<210> SEQ ID NO 577
<211> LENGTH: 50
<212> TYPE: DNA
<213> ORGANISM: Human papillomavirus

<400> SEQUENCE: 577
taccactcgc agtaccaatt ttaccatcag tggacaatgt tatagtacac    50

<210> SEQ ID NO 578
<211> LENGTH: 43
<212> TYPE: DNA
<213> ORGANISM: Human papillomavirus

<400> SEQUENCE: 578
ccattgttgt gtccctgtgc ctctatggta tcctcagact ccc    43

<210> SEQ ID NO 579
<211> LENGTH: 46
<212> TYPE: DNA
<213> ORGANISM: Human papillomavirus

<400> SEQUENCE: 579
caacaaatac cattgttgtg tccctctatg gtatcctcag actccc    46

<210> SEQ ID NO 580
<211> LENGTH: 45
<212> TYPE: DNA
<213> ORGANISM: Human papillomavirus

<400> SEQUENCE: 580
cctccaacaa aaatcctaag gacagccaat ggcaggaaca cagcc    45

<210> SEQ ID NO 581
<211> LENGTH: 45
<212> TYPE: DNA
<213> ORGANISM: Human papillomavirus

<400> SEQUENCE: 581
ctccaacaaa aatcctaagg acagccaatg gcaggaacac agcct    45

<210> SEQ ID NO 582
<211> LENGTH: 21
<212> TYPE: DNA
<213> ORGANISM: Human papillomavirus

<400> SEQUENCE: 582
gatttacctt tggcccagtg c    21

<210> SEQ ID NO 583
<211> LENGTH: 46
<212> TYPE: DNA
<213> ORGANISM: Human papillomavirus

<400> SEQUENCE: 583
tataatggat gcccactaag gccgcctgtg ttggtgttga aatagg    46

<210> SEQ ID NO 584
<211> LENGTH: 20
<212> TYPE: DNA
<213> ORGANISM: Human papillomavirus

<400> SEQUENCE: 584
accctgatac gcagcgattg                                               20

<210> SEQ ID NO 585
<211> LENGTH: 20
<212> TYPE: DNA
<213> ORGANISM: Human papillomavirus

<400> SEQUENCE: 585
gttatgtata tgcccctcg                                                20

<210> SEQ ID NO 586
<211> LENGTH: 52
<212> TYPE: DNA
<213> ORGANISM: Human papillomavirus

<400> SEQUENCE: 586
caacgcgcag tactaatttt acattgcatc agtggataat gttatagtac ac           52

<210> SEQ ID NO 587
<211> LENGTH: 50
<212> TYPE: DNA
<213> ORGANISM: Human papillomavirus

<400> SEQUENCE: 587
tacaacgcgc agtactaatt ttaccatcag tggataatgt tatagtacac              50

<210> SEQ ID NO 588
<211> LENGTH: 20
<212> TYPE: DNA
<213> ORGANISM: Human papillomavirus

<400> SEQUENCE: 588
gttatgtgta tgcccctcg                                                20

<210> SEQ ID NO 589
<211> LENGTH: 46
<212> TYPE: DNA
<213> ORGANISM: Human papillomavirus

<400> SEQUENCE: 589
caacaaatac cattgttgtg tccctctatg gtgtcctctg actccc                  46

<210> SEQ ID NO 590
<211> LENGTH: 25
<212> TYPE: DNA
<213> ORGANISM: Human papillomavirus

<400> SEQUENCE: 590
ccaatcatcc aaaatagcag gattc                                         25

<210> SEQ ID NO 591
<211> LENGTH: 49
<212> TYPE: DNA
<213> ORGANISM: Human papillomavirus

<400> SEQUENCE: 591
tagatgatac tgaaaattcc ccgttgccta taatacatag ttgcgtttg               49

<210> SEQ ID NO 592
<211> LENGTH: 26
<212> TYPE: DNA
<213> ORGANISM: Human papillomavirus

```
<400> SEQUENCE: 592
cctgagtcta cattatataa ccctga                                              26

<210> SEQ ID NO 593
<211> LENGTH: 42
<212> TYPE: DNA
<213> ORGANISM: Human papillomavirus

<400> SEQUENCE: 593
cccactaagg ccaacaccta atgtacgcag cgattggtat gg                            42

<210> SEQ ID NO 594
<211> LENGTH: 20
<212> TYPE: DNA
<213> ORGANISM: Human papillomavirus

<400> SEQUENCE: 594
gatttacctt tggcccagtg                                                     20

<210> SEQ ID NO 595
<211> LENGTH: 33
<212> TYPE: DNA
<213> ORGANISM: Human papillomavirus

<400> SEQUENCE: 595
attatgtgct gccatatcta cttcagaaac tac                                      33

<210> SEQ ID NO 596
<211> LENGTH: 32
<212> TYPE: DNA
<213> ORGANISM: Human papillomavirus

<400> SEQUENCE: 596
aaccaataag gtttattgaa tatttgggca tc                                       32

<210> SEQ ID NO 597
<211> LENGTH: 34
<212> TYPE: DNA
<213> ORGANISM: Human papillomavirus

<400> SEQUENCE: 597
accaataagg tttattgaat atttgggcat caga                                     34

<210> SEQ ID NO 598
<211> LENGTH: 31
<212> TYPE: DNA
<213> ORGANISM: Human papillomavirus

<400> SEQUENCE: 598
caataaggtt tattgaatat ttgggcatca g                                        31

<210> SEQ ID NO 599
<211> LENGTH: 31
<212> TYPE: DNA
<213> ORGANISM: Human papillomavirus

<400> SEQUENCE: 599
ataaggttta ttgaatattt gggcatcaga g                                        31

<210> SEQ ID NO 600
<211> LENGTH: 30
<212> TYPE: DNA
<213> ORGANISM: Human papillomavirus
```

```
<400> SEQUENCE: 600
aaggtttatt gaatatttgg gcatcagagg                                        30

<210> SEQ ID NO 601
<211> LENGTH: 30
<212> TYPE: DNA
<213> ORGANISM: Human papillomavirus

<400> SEQUENCE: 601
aaatgcaggt gtggataata gagaatgtat                                        30

<210> SEQ ID NO 602
<211> LENGTH: 29
<212> TYPE: DNA
<213> ORGANISM: Human papillomavirus

<400> SEQUENCE: 602
aaatgcaggt gtggataata gagaatgta                                         29

<210> SEQ ID NO 603
<211> LENGTH: 30
<212> TYPE: DNA
<213> ORGANISM: Human papillomavirus

<400> SEQUENCE: 603
attatgtgct gccatatcta cttcagaaac                                        30

<210> SEQ ID NO 604
<211> LENGTH: 30
<212> TYPE: DNA
<213> ORGANISM: Human papillomavirus

<400> SEQUENCE: 604
gtgctgccat atctacttca gaaactacat                                        30

<210> SEQ ID NO 605
<211> LENGTH: 34
<212> TYPE: DNA
<213> ORGANISM: Human papillomavirus

<400> SEQUENCE: 605
tatgtgctgc catatctact tcagaaacta cata                                   34

<210> SEQ ID NO 606
<211> LENGTH: 35
<212> TYPE: DNA
<213> ORGANISM: Human papillomavirus

<400> SEQUENCE: 606
acttcagaaa ctacatataa aaatactaac tttaa                                  35

<210> SEQ ID NO 607
<211> LENGTH: 30
<212> TYPE: DNA
<213> ORGANISM: Human papillomavirus

<400> SEQUENCE: 607
ttatgtgctg ccatatctac ttcagaaact                                        30

<210> SEQ ID NO 608
<211> LENGTH: 34
<212> TYPE: DNA
<213> ORGANISM: Human papillomavirus
```

```
<400> SEQUENCE: 608
ctacttcaga aactacatat aaaaatacta actt                                34

<210> SEQ ID NO 609
<211> LENGTH: 36
<212> TYPE: DNA
<213> ORGANISM: Human papillomavirus

<400> SEQUENCE: 609
tcagaaacta catataaaaa tactaacttt aaggag                              36

<210> SEQ ID NO 610
<211> LENGTH: 37
<212> TYPE: DNA
<213> ORGANISM: Human papillomavirus

<400> SEQUENCE: 610
aactacatat aaaatacta actttaagga gtaccta                              37

<210> SEQ ID NO 611
<211> LENGTH: 38
<212> TYPE: DNA
<213> ORGANISM: Human papillomavirus

<400> SEQUENCE: 611
atgtgctgcc atatctactt cagaaactac atataaaa                            38

<210> SEQ ID NO 612
<211> LENGTH: 37
<212> TYPE: DNA
<213> ORGANISM: Human papillomavirus

<400> SEQUENCE: 612
tgccatatct acttcagaaa ctacatataa aaatact                             37

<210> SEQ ID NO 613
<211> LENGTH: 31
<212> TYPE: DNA
<213> ORGANISM: Human papillomavirus

<400> SEQUENCE: 613
tctacacagt ctcctgtacc tgggcaatat g                                   31

<210> SEQ ID NO 614
<211> LENGTH: 31
<212> TYPE: DNA
<213> ORGANISM: Human papillomavirus

<400> SEQUENCE: 614
aatatgtgct tctacacagt ctcctgtacc t                                   31

<210> SEQ ID NO 615
<211> LENGTH: 31
<212> TYPE: DNA
<213> ORGANISM: Human papillomavirus

<400> SEQUENCE: 615
ctcctgtacc tgggcaatat gatgctacca a                                   31

<210> SEQ ID NO 616
<211> LENGTH: 30
<212> TYPE: DNA
<213> ORGANISM: Human papillomavirus
```

```
<400> SEQUENCE: 616
cacgtctaat gtttctgagg acgttaggga                                    30

<210> SEQ ID NO 617
<211> LENGTH: 27
<212> TYPE: DNA
<213> ORGANISM: Human papillomavirus

<400> SEQUENCE: 617
gtctaatgtt tctgaggacg ttaggga                                       27

<210> SEQ ID NO 618
<211> LENGTH: 24
<212> TYPE: DNA
<213> ORGANISM: Human papillomavirus

<400> SEQUENCE: 618
taatgtttct gaggacgtta ggga                                          24

<210> SEQ ID NO 619
<211> LENGTH: 31
<212> TYPE: DNA
<213> ORGANISM: Human papillomavirus

<400> SEQUENCE: 619
taatgtttct gaggacgtta gggacaatgt g                                  31

<210> SEQ ID NO 620
<211> LENGTH: 29
<212> TYPE: DNA
<213> ORGANISM: Human papillomavirus

<400> SEQUENCE: 620
taatgtttct gaggacgtta gggacaatg                                     29

<210> SEQ ID NO 621
<211> LENGTH: 30
<212> TYPE: DNA
<213> ORGANISM: Human papillomavirus

<400> SEQUENCE: 621
aatgtttctg aggacgttag ggacaatgtg                                    30

<210> SEQ ID NO 622
<211> LENGTH: 30
<212> TYPE: DNA
<213> ORGANISM: Human papillomavirus

<400> SEQUENCE: 622
aatatgtgct tctacacagt ctcctgtacc                                    30

<210> SEQ ID NO 623
<211> LENGTH: 30
<212> TYPE: DNA
<213> ORGANISM: Human papillomavirus

<400> SEQUENCE: 623
tgcttctaca cagtctcctg tacctgggca                                    30

<210> SEQ ID NO 624
<211> LENGTH: 30
<212> TYPE: DNA
<213> ORGANISM: Human papillomavirus
```

```
<400> SEQUENCE: 624
tgcttctaca cagtctcctg tacctgggca                                    30

<210> SEQ ID NO 625
<211> LENGTH: 30
<212> TYPE: DNA
<213> ORGANISM: Human papillomavirus

<400> SEQUENCE: 625
acctgggcaa tatgatgcta ccaaatttaa                                    30

<210> SEQ ID NO 626
<211> LENGTH: 35
<212> TYPE: DNA
<213> ORGANISM: Human papillomavirus

<400> SEQUENCE: 626
cctgtacctg ggcaatatga tgctaccaaa tttaa                              35

<210> SEQ ID NO 627
<211> LENGTH: 38
<212> TYPE: DNA
<213> ORGANISM: Human papillomavirus

<400> SEQUENCE: 627
tggtcctggc actgataata gggaatgtat atcaatgg                           38

<210> SEQ ID NO 628
<211> LENGTH: 39
<212> TYPE: DNA
<213> ORGANISM: Human papillomavirus

<400> SEQUENCE: 628
ataataggga atgtatatca atggattata aacaaacac                          39

<210> SEQ ID NO 629
<211> LENGTH: 39
<212> TYPE: DNA
<213> ORGANISM: Human papillomavirus

<400> SEQUENCE: 629
ggcactgata atagggaatg tatatcaatg gattataaa                          39

<210> SEQ ID NO 630
<211> LENGTH: 30
<212> TYPE: DNA
<213> ORGANISM: Human papillomavirus

<400> SEQUENCE: 630
tggtcctggc actgataata gggaatgtat                                    30

<210> SEQ ID NO 631
<211> LENGTH: 32
<212> TYPE: DNA
<213> ORGANISM: Human papillomavirus

<400> SEQUENCE: 631
ataataggga atgtatatca atggattata aa                                 32

<210> SEQ ID NO 632
<211> LENGTH: 33
<212> TYPE: DNA
<213> ORGANISM: Human papillomavirus
```

| | | |
|---|---|---|
| <400> SEQUENCE: 632 | | |
| ataataggga atgtatatca atggattata aac | | 33 |
| | | |
| <210> SEQ ID NO 633 <211> LENGTH: 37 <212> TYPE: DNA <213> ORGANISM: Human papillomavirus | | |
| <400> SEQUENCE: 633 | | |
| ataataggga atgtatatca atggattata aacaaac | | 37 |
| | | |
| <210> SEQ ID NO 634 <211> LENGTH: 30 <212> TYPE: DNA <213> ORGANISM: Human papillomavirus | | |
| <400> SEQUENCE: 634 | | |
| tgctgcaatt gcaaacagtg atactacatt | | 30 |
| | | |
| <210> SEQ ID NO 635 <211> LENGTH: 35 <212> TYPE: DNA <213> ORGANISM: Human papillomavirus | | |
| <400> SEQUENCE: 635 | | |
| aacagtgata ctacatttaa aagtagtaat tttaa | | 35 |
| | | |
| <210> SEQ ID NO 636 <211> LENGTH: 35 <212> TYPE: DNA <213> ORGANISM: Human papillomavirus | | |
| <400> SEQUENCE: 636 | | |
| ttatccatgg attataaaca aacacagtta tgttt | | 35 |
| | | |
| <210> SEQ ID NO 637 <211> LENGTH: 37 <212> TYPE: DNA <213> ORGANISM: Human papillomavirus | | |
| <400> SEQUENCE: 637 | | |
| ttatccatgg attataaaca aacacagtta tgtttac | | 37 |
| | | |
| <210> SEQ ID NO 638 <211> LENGTH: 42 <212> TYPE: DNA <213> ORGANISM: Human papillomavirus | | |
| <400> SEQUENCE: 638 | | |
| ttatccatgg attataaaca aacacagtta tgtttacttg ga | | 42 |
| | | |
| <210> SEQ ID NO 639 <211> LENGTH: 30 <212> TYPE: DNA <213> ORGANISM: Human papillomavirus | | |
| <400> SEQUENCE: 639 | | |
| acaaggtcat aataatggta tttgttgggg | | 30 |
| | | |
| <210> SEQ ID NO 640 <211> LENGTH: 30 <212> TYPE: DNA <213> ORGANISM: Human papillomavirus | | |

```
<400> SEQUENCE: 640
gtagttcctg aacctttaat gtacaggtca                                      30

<210> SEQ ID NO 641
<211> LENGTH: 30
<212> TYPE: DNA
<213> ORGANISM: Human papillomavirus

<400> SEQUENCE: 641
caaggtcata ataatggtat ttgttggggc                                      30

<210> SEQ ID NO 642
<211> LENGTH: 35
<212> TYPE: DNA
<213> ORGANISM: Human papillomavirus

<400> SEQUENCE: 642
atgtttatcc atggattata aacaaacaca gttat                                35

<210> SEQ ID NO 643
<211> LENGTH: 30
<212> TYPE: DNA
<213> ORGANISM: Human papillomavirus

<400> SEQUENCE: 643
ttatccatgg attataaaca aacacagtta                                      30

<210> SEQ ID NO 644
<211> LENGTH: 33
<212> TYPE: DNA
<213> ORGANISM: Human papillomavirus

<400> SEQUENCE: 644
ttatccatgg attataaaca aacacagtta tgt                                  33

<210> SEQ ID NO 645
<211> LENGTH: 30
<212> TYPE: DNA
<213> ORGANISM: Human papillomavirus

<400> SEQUENCE: 645
tggacaaccg ggtgctgata atagggaatg                                      30

<210> SEQ ID NO 646
<211> LENGTH: 23
<212> TYPE: DNA
<213> ORGANISM: Human papillomavirus

<400> SEQUENCE: 646
tggacaaccg ggtgctgata ata                                             23

<210> SEQ ID NO 647
<211> LENGTH: 36
<212> TYPE: DNA
<213> ORGANISM: Human papillomavirus

<400> SEQUENCE: 647
gataataggg aatgtttatc catggattat aaacaa                               36

<210> SEQ ID NO 648
<211> LENGTH: 34
<212> TYPE: DNA
<213> ORGANISM: Human papillomavirus
```

```
<400> SEQUENCE: 648
agggaatgtt tatccatgga ttataaacaa acac                        34

<210> SEQ ID NO 649
<211> LENGTH: 30
<212> TYPE: DNA
<213> ORGANISM: Human papillomavirus

<400> SEQUENCE: 649
agggaatgtt tatccatgga ttataaacaa                             30

<210> SEQ ID NO 650
<211> LENGTH: 33
<212> TYPE: DNA
<213> ORGANISM: Human papillomavirus

<400> SEQUENCE: 650
aatgtttatc catggattat aaacaaacac agt                         33

<210> SEQ ID NO 651
<211> LENGTH: 30
<212> TYPE: DNA
<213> ORGANISM: Human papillomavirus

<400> SEQUENCE: 651
actttatgca cacaagtaac tagtgacagt                             30

<210> SEQ ID NO 652
<211> LENGTH: 35
<212> TYPE: DNA
<213> ORGANISM: Human papillomavirus

<400> SEQUENCE: 652
actagtgaca gtacatataa aaatgaaaat tttaa                       35

<210> SEQ ID NO 653
<211> LENGTH: 31
<212> TYPE: DNA
<213> ORGANISM: Human papillomavirus

<400> SEQUENCE: 653 atggattta ctacattaca agctaataaa a                            31

<210> SEQ ID NO 654
<211> LENGTH: 34
<212> TYPE: DNA
<213> ORGANISM: Human papillomavirus

<400> SEQUENCE: 654
tttggtgcaa tggattttac tacattacaa gcta                        34

<210> SEQ ID NO 655
<211> LENGTH: 33
<212> TYPE: DNA
<213> ORGANISM: Human papillomavirus

<400> SEQUENCE: 655
gtgcaatgga ttttactaca ttacaagcta ata                         33

<210> SEQ ID NO 656
<211> LENGTH: 29
<212> TYPE: DNA
<213> ORGANISM: Human papillomavirus
```

```
<400> SEQUENCE: 656
ataacaggga atgcatttct atggattat                                           29

<210> SEQ ID NO 657
<211> LENGTH: 30
<212> TYPE: DNA
<213> ORGANISM: Human papillomavirus

<400> SEQUENCE: 657
ttctgctgtg tcttctagtg acagtacata                                          30

<210> SEQ ID NO 658
<211> LENGTH: 35
<212> TYPE: DNA
<213> ORGANISM: Human papillomavirus

<400> SEQUENCE: 658
tctagtgaca gtacatataa aaatgacaat tttaa                                    35

<210> SEQ ID NO 659
<211> LENGTH: 36
<212> TYPE: DNA
<213> ORGANISM: Human papillomavirus

<400> SEQUENCE: 659
tctatagagt cttccatacc ttctacatat gatcct                                   36

<210> SEQ ID NO 660
<211> LENGTH: 38
<212> TYPE: DNA
<213> ORGANISM: Human papillomavirus

<400> SEQUENCE: 660
tgggccttat gtagccaata aggcttatta ataactg                                  38

<210> SEQ ID NO 661
<211> LENGTH: 35
<212> TYPE: DNA
<213> ORGANISM: Human papillomavirus

<400> SEQUENCE: 661
gccaataagg cttattaaat aactgggaat cagag                                    35

<210> SEQ ID NO 662
<211> LENGTH: 30
<212> TYPE: DNA
<213> ORGANISM: Human papillomavirus

<400> SEQUENCE: 662
caataaggct tattaaataa ctgggaatca                                          30

<210> SEQ ID NO 663
<211> LENGTH: 31
<212> TYPE: DNA
<213> ORGANISM: Human papillomavirus

<400> SEQUENCE: 663
aataaggctt attaaataac tgggaatcag a                                        31

<210> SEQ ID NO 664
<211> LENGTH: 32
<212> TYPE: DNA
<213> ORGANISM: Human papillomavirus
```

<400> SEQUENCE: 664
tcttccatac cttctacata tgatccttct aa                32

<210> SEQ ID NO 665
<211> LENGTH: 40
<212> TYPE: DNA
<213> ORGANISM: Human papillomavirus

<400> SEQUENCE: 665
tccataccct ctacatatga tccttctaag tttaaggaat        40

<210> SEQ ID NO 666
<211> LENGTH: 36
<212> TYPE: DNA
<213> ORGANISM: Human papillomavirus

<400> SEQUENCE: 666
ttatctacct ctatagagtc ttccatacct tctaca            36

<210> SEQ ID NO 667
<211> LENGTH: 33
<212> TYPE: DNA
<213> ORGANISM: Human papillomavirus

<400> SEQUENCE: 667
ataccttcta catatgatcc ttctaagttt aag               33

<210> SEQ ID NO 668
<211> LENGTH: 37
<212> TYPE: DNA
<213> ORGANISM: Human papillomavirus

<400> SEQUENCE: 668
ttctacatat gatccttcta agtttaagga atatacc           37

<210> SEQ ID NO 669
<211> LENGTH: 34
<212> TYPE: DNA
<213> ORGANISM: Human papillomavirus

<400> SEQUENCE: 669
tatgtagcca ataaggctta ttaaataact ggga              34

<210> SEQ ID NO 670
<211> LENGTH: 30
<212> TYPE: DNA
<213> ORGANISM: Human papillomavirus

<400> SEQUENCE: 670
accaataagg acagtaggga taatgtgtct                   30

<210> SEQ ID NO 671
<211> LENGTH: 28
<212> TYPE: DNA
<213> ORGANISM: Human papillomavirus

<400> SEQUENCE: 671
accaataagg acagtaggga taatgtgt                     28

<210> SEQ ID NO 672
<211> LENGTH: 27
<212> TYPE: DNA
<213> ORGANISM: Human papillomavirus

<400> SEQUENCE: 672
accaataagg acagtaggga taatgtg    27

<210> SEQ ID NO 673
<211> LENGTH: 30
<212> TYPE: DNA
<213> ORGANISM: Human papillomavirus

<400> SEQUENCE: 673
cctctataga gtcttccata ccttctacat    30

<210> SEQ ID NO 674
<211> LENGTH: 35
<212> TYPE: DNA
<213> ORGANISM: Human papillomavirus

<400> SEQUENCE: 674
tccatacctt ctacatatga tccttctaag tttaa    35

<210> SEQ ID NO 675
<211> LENGTH: 30
<212> TYPE: DNA
<213> ORGANISM: Human papillomavirus

<400> SEQUENCE: 675
gttattacgc aggatgttag ggataatgtg    30

<210> SEQ ID NO 676
<211> LENGTH: 31
<212> TYPE: DNA
<213> ORGANISM: Human papillomavirus

<400> SEQUENCE: 676
agctacagct gttattacgc aggatgttag g    31

<210> SEQ ID NO 677
<211> LENGTH: 33
<212> TYPE: DNA
<213> ORGANISM: Human papillomavirus

<400> SEQUENCE: 677
acgcaggatg ttagggataa tgtgtcagtt gat    33

<210> SEQ ID NO 678
<211> LENGTH: 40
<212> TYPE: DNA
<213> ORGANISM: Human papillomavirus

<400> SEQUENCE: 678
ctacagctgt tattacgcag gatgttaggg ataatgtgtc    40

<210> SEQ ID NO 679
<211> LENGTH: 30
<212> TYPE: DNA
<213> ORGANISM: Human papillomavirus

<400> SEQUENCE: 679
acagctgtta ttacgcagga tgttagggat    30

<210> SEQ ID NO 680
<211> LENGTH: 30
<212> TYPE: DNA
<213> ORGANISM: Human papillomavirus

```
<400> SEQUENCE: 680
tgttattacg caggatgtta gggataatgt                                    30

<210> SEQ ID NO 681
<211> LENGTH: 30
<212> TYPE: DNA
<213> ORGANISM: Human papillomavirus

<400> SEQUENCE: 681
ttacgcagga tgttagggat aatgtgtcag                                    30

<210> SEQ ID NO 682
<211> LENGTH: 30
<212> TYPE: DNA
<213> ORGANISM: Human papillomavirus

<400> SEQUENCE: 682
tacacaaaat cctgtgccaa gtacatatga                                    30

<210> SEQ ID NO 683
<211> LENGTH: 35
<212> TYPE: DNA
<213> ORGANISM: Human papillomavirus

<400> SEQUENCE: 683
cctgtgccaa gtacatatga ccctactaag tttaa                              35

<210> SEQ ID NO 684
<211> LENGTH: 38
<212> TYPE: DNA
<213> ORGANISM: Human papillomavirus

<400> SEQUENCE: 684
gacaacaaac agactcagtt atgtataata ggctgtgc                           38

<210> SEQ ID NO 685
<211> LENGTH: 32
<212> TYPE: DNA
<213> ORGANISM: Human papillomavirus

<400> SEQUENCE: 685
tcatcatatt tattaaataa gggatgacca ct                                 32

<210> SEQ ID NO 686
<211> LENGTH: 34
<212> TYPE: DNA
<213> ORGANISM: Human papillomavirus

<400> SEQUENCE: 686
acatctgttg acaacaaaca gactcagtta tgta                               34

<210> SEQ ID NO 687
<211> LENGTH: 34
<212> TYPE: DNA
<213> ORGANISM: Human papillomavirus

<400> SEQUENCE: 687
atcatattta ttaaataagg gatgaccact aagg                               34

<210> SEQ ID NO 688
<211> LENGTH: 33
<212> TYPE: DNA
<213> ORGANISM: Human papillomavirus
```

-continued

```
<400> SEQUENCE: 688
tgttgacaac aaacagactc agttatgtat aat                                33

<210> SEQ ID NO 689
<211> LENGTH: 33
<212> TYPE: DNA
<213> ORGANISM: Human papillomavirus

<400> SEQUENCE: 689
tatttattaa ataagggatg accactaagg cca                                33

<210> SEQ ID NO 690
<211> LENGTH: 36
<212> TYPE: DNA
<213> ORGANISM: Human papillomavirus

<400> SEQUENCE: 690
ttgacaacaa acagactcag ttatgtataa taggct                             36

<210> SEQ ID NO 691
<211> LENGTH: 33
<212> TYPE: DNA
<213> ORGANISM: Human papillomavirus

<400> SEQUENCE: 691
gcggtttccc caacatttac tccaagtaac ttt                                33

<210> SEQ ID NO 692
<211> LENGTH: 31
<212> TYPE: DNA
<213> ORGANISM: Human papillomavirus

<400> SEQUENCE: 692
tccccaacat ttactccaag taactttaag c                                  31

<210> SEQ ID NO 693
<211> LENGTH: 31
<212> TYPE: DNA
<213> ORGANISM: Human papillomavirus

<400> SEQUENCE: 693
aaacagactc agttatgtat aataggctgt g                                  31

<210> SEQ ID NO 694
<211> LENGTH: 30
<212> TYPE: DNA
<213> ORGANISM: Human papillomavirus

<400> SEQUENCE: 694
cagactcagt tatgtataat aggctgtgct                                    30

<210> SEQ ID NO 695
<211> LENGTH: 38
<212> TYPE: DNA
<213> ORGANISM: Human papillomavirus

<400> SEQUENCE: 695
tctgttgaca acaaacagac tcagttatgt ataatagg                           38

<210> SEQ ID NO 696
<211> LENGTH: 35
<212> TYPE: DNA
<213> ORGANISM: Human papillomavirus
```

```
<400> SEQUENCE: 696
tctgttgaca acaaacagac tcagttatgt ataat                              35

<210> SEQ ID NO 697
<211> LENGTH: 35
<212> TYPE: DNA
<213> ORGANISM: Human papillomavirus

<400> SEQUENCE: 697
gttgacaaca aacagactca gttatgtata atagg                              35

<210> SEQ ID NO 698
<211> LENGTH: 36
<212> TYPE: DNA
<213> ORGANISM: Human papillomavirus

<400> SEQUENCE: 698
tgttgacaac aaacagactc agttatgtat aatagg                             36

<210> SEQ ID NO 699
<211> LENGTH: 40
<212> TYPE: DNA
<213> ORGANISM: Human papillomavirus

<400> SEQUENCE: 699
tctgttgaca acaaacagac tcagttatgt ataataggct                         40

<210> SEQ ID NO 700
<211> LENGTH: 30
<212> TYPE: DNA
<213> ORGANISM: Human papillomavirus

<400> SEQUENCE: 700
gctgcggttt ccccaacatt tactccaagt                                    30

<210> SEQ ID NO 701
<211> LENGTH: 30
<212> TYPE: DNA
<213> ORGANISM: Human papillomavirus

<400> SEQUENCE: 701
gcggtttccc caacatttac tccaagtaac                                    30

<210> SEQ ID NO 702
<211> LENGTH: 35
<212> TYPE: DNA
<213> ORGANISM: Human papillomavirus

<400> SEQUENCE: 702
gcggtttccc caacatttac tccaagtaac tttaa                              35

<210> SEQ ID NO 703
<211> LENGTH: 38
<212> TYPE: DNA
<213> ORGANISM: Human papillomavirus

<400> SEQUENCE: 703
taatggcata tgttggggca atcagttgtt tgtcacag                           38

<210> SEQ ID NO 704
<211> LENGTH: 30
<212> TYPE: DNA
<213> ORGANISM: Human papillomavirus
```

```
<400> SEQUENCE: 704
actaggagta ggaaaaaaag cactgctttg                                    30

<210> SEQ ID NO 705
<211> LENGTH: 39
<212> TYPE: DNA
<213> ORGANISM: Human papillomavirus

<400> SEQUENCE: 705
gggccacaat aatggcatat gttggggcaa tcagttgtt                          39

<210> SEQ ID NO 706
<211> LENGTH: 32
<212> TYPE: DNA
<213> ORGANISM: Human papillomavirus

<400> SEQUENCE: 706
tatgttgggg caatcagttg tttgtcacag tt                                 32

<210> SEQ ID NO 707
<211> LENGTH: 30
<212> TYPE: DNA
<213> ORGANISM: Human papillomavirus

<400> SEQUENCE: 707
taggagtagg aaaaaaagca ctgctttgta                                    30

<210> SEQ ID NO 708
<211> LENGTH: 31
<212> TYPE: DNA
<213> ORGANISM: Human papillomavirus

<400> SEQUENCE: 708
cacaataatg gcatatgttg gggcaatcag t                                  31

<210> SEQ ID NO 709
<211> LENGTH: 37
<212> TYPE: DNA
<213> ORGANISM: Human papillomavirus

<400> SEQUENCE: 709
acaataatgg catatgttgg ggcaatcagt tgtttgt                            37

<210> SEQ ID NO 710
<211> LENGTH: 30
<212> TYPE: DNA
<213> ORGANISM: Human papillomavirus

<400> SEQUENCE: 710
tacggtttat taaataattg ggattctgag                                    30

<210> SEQ ID NO 711
<211> LENGTH: 40
<212> TYPE: DNA
<213> ORGANISM: Human papillomavirus

<400> SEQUENCE: 711
gaggttaaaa aggaaagcac atataaaaat gaaaatttta                         40

<210> SEQ ID NO 712
<211> LENGTH: 31
<212> TYPE: DNA
<213> ORGANISM: Human papillomavirus
```

```
<400> SEQUENCE: 712
tttatgtgct gaggttaaaa aggaaagcac a                              31

<210> SEQ ID NO 713
<211> LENGTH: 33
<212> TYPE: DNA
<213> ORGANISM: Human papillomavirus

<400> SEQUENCE: 713
ttgtaaccag tacggtttat taataattg gga                             33

<210> SEQ ID NO 714
<211> LENGTH: 33
<212> TYPE: DNA
<213> ORGANISM: Human papillomavirus

<400> SEQUENCE: 714
gttaaaaagg aaagcacata taaaaatgaa aat                            33

<210> SEQ ID NO 715
<211> LENGTH: 40
<212> TYPE: DNA
<213> ORGANISM: Human papillomavirus

<400> SEQUENCE: 715
taaaaaggaa agcacatata aaaatgaaaa ttttaaggaa                     40

<210> SEQ ID NO 716
<211> LENGTH: 40
<212> TYPE: DNA
<213> ORGANISM: Human papillomavirus

<400> SEQUENCE: 716
ggaaagcaca tataaaaatg aaaattttaa ggaatacctt                     40

<210> SEQ ID NO 717
<211> LENGTH: 38
<212> TYPE: DNA
<213> ORGANISM: Human papillomavirus

<400> SEQUENCE: 717
tgtaaccagt acggtttatt aataattgg gattctga                        38

<210> SEQ ID NO 718
<211> LENGTH: 40
<212> TYPE: DNA
<213> ORGANISM: Human papillomavirus

<400> SEQUENCE: 718
tgtgctgagg ttaaaaagga agcacatat aaaaatgaaa                      40

<210> SEQ ID NO 719
<211> LENGTH: 30
<212> TYPE: DNA
<213> ORGANISM: Human papillomavirus

<400> SEQUENCE: 719
ccagtacggt ttattaaata attgggattc                                30

<210> SEQ ID NO 720
<211> LENGTH: 31
<212> TYPE: DNA
<213> ORGANISM: Human papillomavirus
```

-continued

```
<400> SEQUENCE: 720
ctgaggttaa aaaggaaagc acatataaaa a                                    31

<210> SEQ ID NO 721
<211> LENGTH: 33
<212> TYPE: DNA
<213> ORGANISM: Human papillomavirus

<400> SEQUENCE: 721
ttaaaaagga agcacatat aaaaatgaaa aat                                   33

<210> SEQ ID NO 722
<211> LENGTH: 32
<212> TYPE: DNA
<213> ORGANISM: Human papillomavirus

<400> SEQUENCE: 722
ctgaggttaa aaaggaaagc acatataaaa at                                   32

<210> SEQ ID NO 723
<211> LENGTH: 31
<212> TYPE: DNA
<213> ORGANISM: Human papillomavirus

<400> SEQUENCE: 723
tgctgaggtt aaaaggaaa gcacatataa a                                     31

<210> SEQ ID NO 724
<211> LENGTH: 38
<212> TYPE: DNA
<213> ORGANISM: Human papillomavirus

<400> SEQUENCE: 724
aaaaaggaaa gcacatataa aaatgaaaat tttaagga                             38

<210> SEQ ID NO 725
<211> LENGTH: 39
<212> TYPE: DNA
<213> ORGANISM: Human papillomavirus

<400> SEQUENCE: 725
tgctgaggtt aaaaggaaa gcacatataa aaatgaaaa                             39

<210> SEQ ID NO 726
<211> LENGTH: 34
<212> TYPE: DNA
<213> ORGANISM: Human papillomavirus

<400> SEQUENCE: 726
tgctgaggtt aaaaggaaa gcacatataa aaat                                  34

<210> SEQ ID NO 727
<211> LENGTH: 45
<212> TYPE: DNA
<213> ORGANISM: Human papillomavirus

<400> SEQUENCE: 727
tttatgtgct gaggttaaaa aggaaagcac atataaaaat gaaaa                     45

<210> SEQ ID NO 728
<211> LENGTH: 40
<212> TYPE: DNA
<213> ORGANISM: Human papillomavirus
```

```
<400> SEQUENCE: 728
tttatgtgct gaggttaaaa aggaaagcac atataaaaat                              40

<210> SEQ ID NO 729
<211> LENGTH: 35
<212> TYPE: DNA
<213> ORGANISM: Human papillomavirus

<400> SEQUENCE: 729
tttatgtgct gaggttaaaa aggaaagcac atata                                   35

<210> SEQ ID NO 730
<211> LENGTH: 30
<212> TYPE: DNA
<213> ORGANISM: Human papillomavirus

<400> SEQUENCE: 730
ggtaaacctg gtatagataa tagggaatgt                                         30

<210> SEQ ID NO 731
<211> LENGTH: 31
<212> TYPE: DNA
<213> ORGANISM: Human papillomavirus

<400> SEQUENCE: 731
tggtaaacct ggtatagata tagggaatg t                                        31

<210> SEQ ID NO 732
<211> LENGTH: 30
<212> TYPE: DNA
<213> ORGANISM: Human papillomavirus

<400> SEQUENCE: 732
tttatgtgct gaggttaaaa aggaaagcac                                         30

<210> SEQ ID NO 733
<211> LENGTH: 40
<212> TYPE: DNA
<213> ORGANISM: Human papillomavirus

<400> SEQUENCE: 733
ccttgggcac gttgcaacca ataaggttta ttaataact                               40

<210> SEQ ID NO 734
<211> LENGTH: 40
<212> TYPE: DNA
<213> ORGANISM: Human papillomavirus

<400> SEQUENCE: 734
ttagtactgc tacagaacag ttaagtaaat atgatgcacg                              40

<210> SEQ ID NO 735
<211> LENGTH: 40
<212> TYPE: DNA
<213> ORGANISM: Human papillomavirus

<400> SEQUENCE: 735
ggcacgttgc aaccaataag gtttattaaa taactgtgcc                              40

<210> SEQ ID NO 736
<211> LENGTH: 38
<212> TYPE: DNA
<213> ORGANISM: Human papillomavirus
```

-continued

```
<400> SEQUENCE: 736
cgttgcaacc aataaggttt attaaataac tgtgcctc                               38

<210> SEQ ID NO 737
<211> LENGTH: 38
<212> TYPE: DNA
<213> ORGANISM: Human papillomavirus

<400> SEQUENCE: 737
gctacagaac agttaagtaa atatgatgca cgaaaaat                               38

<210> SEQ ID NO 738
<211> LENGTH: 38
<212> TYPE: DNA
<213> ORGANISM: Human papillomavirus

<400> SEQUENCE: 738
ttattatggc cttgggcacg ttgcaaccaa taaggttt                               38

<210> SEQ ID NO 739
<211> LENGTH: 33
<212> TYPE: DNA
<213> ORGANISM: Human papillomavirus

<400> SEQUENCE: 739
acagaacagt taagtaaata tgatgcacga aaa                                    33

<210> SEQ ID NO 740
<211> LENGTH: 35
<212> TYPE: DNA
<213> ORGANISM: Human papillomavirus

<400> SEQUENCE: 740
accaataagg tttattaaat aactgtgcct cagac                                  35

<210> SEQ ID NO 741
<211> LENGTH: 40
<212> TYPE: DNA
<213> ORGANISM: Human papillomavirus

<400> SEQUENCE: 741
agaacagtta agtaaatatg atgcacgaaa aattaatcag                             40

<210> SEQ ID NO 742
<211> LENGTH: 40
<212> TYPE: DNA
<213> ORGANISM: Human papillomavirus

<400> SEQUENCE: 742
taacatgact attagtactg ctacagaaca gttaagtaaa                             40

<210> SEQ ID NO 743
<211> LENGTH: 37
<212> TYPE: DNA
<213> ORGANISM: Human papillomavirus

<400> SEQUENCE: 743
gtaaatatga tgcacgaaaa attaatcagt accttag                                37

<210> SEQ ID NO 744
<211> LENGTH: 40
<212> TYPE: DNA
<213> ORGANISM: Human papillomavirus
```

```
<400> SEQUENCE: 744
tgactattag tactgctaca gaacagttaa gtaaatatga                              40

<210> SEQ ID NO 745
<211> LENGTH: 31
<212> TYPE: DNA
<213> ORGANISM: Human papillomavirus

<400> SEQUENCE: 745
gaacagttaa gtaaatatga tgcacgaaaa a                                       31

<210> SEQ ID NO 746
<211> LENGTH: 36
<212> TYPE: DNA
<213> ORGANISM: Human papillomavirus

<400> SEQUENCE: 746
tactgctaca gaacagttaa gtaaatatga tgcacg                                  36

<210> SEQ ID NO 747
<211> LENGTH: 30
<212> TYPE: DNA
<213> ORGANISM: Human papillomavirus

<400> SEQUENCE: 747
aataataatg ttatagaaga tagtagggac                                         30

<210> SEQ ID NO 748
<211> LENGTH: 30
<212> TYPE: DNA
<213> ORGANISM: Human papillomavirus

<400> SEQUENCE: 748
atagtaggga caatatatca gttgatggca                                         30

<210> SEQ ID NO 749
<211> LENGTH: 30
<212> TYPE: DNA
<213> ORGANISM: Human papillomavirus

<400> SEQUENCE: 749
tattagtact gctacagaac agttaagtaa                                         30

<210> SEQ ID NO 750
<211> LENGTH: 30
<212> TYPE: DNA
<213> ORGANISM: Human papillomavirus

<400> SEQUENCE: 750
acagaacagt taagtaaata tgatgcacga                                         30

<210> SEQ ID NO 751
<211> LENGTH: 35
<212> TYPE: DNA
<213> ORGANISM: Human papillomavirus

<400> SEQUENCE: 751
gaacagttaa gtaaatatga tgcacgaaaa attaa                                   35

<210> SEQ ID NO 752
<211> LENGTH: 30
<212> TYPE: DNA
<213> ORGANISM: Human papillomavirus
```

-continued

```
<400> SEQUENCE: 752
aggtcatccg ggacagcctc gccaagtttt                                       30

<210> SEQ ID NO 753
<211> LENGTH: 32
<212> TYPE: DNA
<213> ORGANISM: Human papillomavirus

<400> SEQUENCE: 753
ttacctcaga atcacaatta tttaataagc ct                                    32

<210> SEQ ID NO 754
<211> LENGTH: 32
<212> TYPE: DNA
<213> ORGANISM: Human papillomavirus

<400> SEQUENCE: 754
ctttaatata aaggtcatcc gggacagcct cg                                    32

<210> SEQ ID NO 755
<211> LENGTH: 30
<212> TYPE: DNA
<213> ORGANISM: Human papillomavirus

<400> SEQUENCE: 755
cagaatcaca attatttaat aagccttatt                                       30

<210> SEQ ID NO 756
<211> LENGTH: 30
<212> TYPE: DNA
<213> ORGANISM: Human papillomavirus

<400> SEQUENCE: 756
ccaatggctg tcccctacct atttcaaggc                                       30

<210> SEQ ID NO 757
<211> LENGTH: 31
<212> TYPE: DNA
<213> ORGANISM: Human papillomavirus

<400> SEQUENCE: 757
cacagccagg gtctgataac agggaatgct t                                     31

<210> SEQ ID NO 758
<211> LENGTH: 30
<212> TYPE: DNA
<213> ORGANISM: Human papillomavirus

<400> SEQUENCE: 758
tggctgtccc ctacctattt caaggcctac                                       30

<210> SEQ ID NO 759
<211> LENGTH: 30
<212> TYPE: DNA
<213> ORGANISM: Human papillomavirus

<400> SEQUENCE: 759
gggtctgata cagggaatg cttatctatg                                        30

<210> SEQ ID NO 760
<211> LENGTH: 30
<212> TYPE: DNA
<213> ORGANISM: Human papillomavirus
```

<400> SEQUENCE: 760
cacagccagg gtctgataac agggaatgct    30

<210> SEQ ID NO 761
<211> LENGTH: 30
<212> TYPE: DNA
<213> ORGANISM: Human papillomavirus

<400> SEQUENCE: 761
cagggaatgc ttatctatgg attataaaca    30

<210> SEQ ID NO 762
<211> LENGTH: 30
<212> TYPE: DNA
<213> ORGANISM: Human papillomavirus

<400> SEQUENCE: 762
cactgaagta actaaggaag gtacatataa    30

<210> SEQ ID NO 763
<211> LENGTH: 30
<212> TYPE: DNA
<213> ORGANISM: Human papillomavirus

<400> SEQUENCE: 763
attatgcact gaagtaacta aggaaggtac    30

<210> SEQ ID NO 764
<211> LENGTH: 35
<212> TYPE: DNA
<213> ORGANISM: Human papillomavirus

<400> SEQUENCE: 764
actaaggaag gtacatataa aaatgataat tttaa    35

<210> SEQ ID NO 765
<211> LENGTH: 32
<212> TYPE: DNA
<213> ORGANISM: Human papillomavirus

<400> SEQUENCE: 765
tgataccaaa gatacacgtg ataatgtatc tg    32

<210> SEQ ID NO 766
<211> LENGTH: 30
<212> TYPE: DNA
<213> ORGANISM: Human papillomavirus

<400> SEQUENCE: 766
atctgctgtt gataccaaag atacacgtga    30

<210> SEQ ID NO 767
<211> LENGTH: 30
<212> TYPE: DNA
<213> ORGANISM: Human papillomavirus

<400> SEQUENCE: 767
gccccgaccg atttcaacac ctacacaggc    30

<210> SEQ ID NO 768
<211> LENGTH: 39
<212> TYPE: DNA
<213> ORGANISM: Human papillomavirus -continued

```
<400> SEQUENCE: 768
gccccgaccg atttcaacac ctacacaggc ccagaccaa                39

<210> SEQ ID NO 769
<211> LENGTH: 37
<212> TYPE: DNA
<213> ORGANISM: Human papillomavirus

<400> SEQUENCE: 769
accaaagata cacgtgataa tgtatctgtg gattata                  37

<210> SEQ ID NO 770
<211> LENGTH: 34
<212> TYPE: DNA
<213> ORGANISM: Human papillomavirus

<400> SEQUENCE: 770
cccgaccgat ttcaacacct acacaggccc agac                     34

<210> SEQ ID NO 771
<211> LENGTH: 30
<212> TYPE: DNA
<213> ORGANISM: Human papillomavirus

<400> SEQUENCE: 771
ctgttgatac caaagataca cgtgataatg                          30

<210> SEQ ID NO 772
<211> LENGTH: 38
<212> TYPE: DNA
<213> ORGANISM: Human papillomavirus

<400> SEQUENCE: 772
gttgatacca agatacacg tgataatgta tctgtgga                  38

<210> SEQ ID NO 773
<211> LENGTH: 30
<212> TYPE: DNA
<213> ORGANISM: Human papillomavirus

<400> SEQUENCE: 773
cgatttcaac acctacacag gcccagacca                          30

<210> SEQ ID NO 774
<211> LENGTH: 30
<212> TYPE: DNA
<213> ORGANISM: Human papillomavirus

<400> SEQUENCE: 774
atctgctgtt gataccaaag atacacgtga                          30

<210> SEQ ID NO 775
<211> LENGTH: 28
<212> TYPE: DNA
<213> ORGANISM: Human papillomavirus

<400> SEQUENCE: 775
ctgctgttga taccaaagat acacgtga                            28

<210> SEQ ID NO 776
<211> LENGTH: 30
<212> TYPE: DNA
<213> ORGANISM: Human papillomavirus
```

-continued

```
<400> SEQUENCE: 776
tctgctgttg ataccaaaga tacacgtgat                                       30

<210> SEQ ID NO 777
<211> LENGTH: 35
<212> TYPE: DNA
<213> ORGANISM: Human papillomavirus

<400> SEQUENCE: 777
atctgctgtt gataccaaag atacacgtga taatg                                 35

<210> SEQ ID NO 778
<211> LENGTH: 37
<212> TYPE: DNA
<213> ORGANISM: Human papillomavirus

<400> SEQUENCE: 778
gttgatacca agatacacg tgataatgta tctgtgg                                37

<210> SEQ ID NO 779
<211> LENGTH: 40
<212> TYPE: DNA
<213> ORGANISM: Human papillomavirus

<400> SEQUENCE: 779
tctgctgttg ataccaaaga tacacgtgat aatgtatctg                            40

<210> SEQ ID NO 780
<211> LENGTH: 30
<212> TYPE: DNA
<213> ORGANISM: Human papillomavirus

<400> SEQUENCE: 780
tctattccta atgtatacac acctaccagt                                       30

<210> SEQ ID NO 781
<211> LENGTH: 35
<212> TYPE: DNA
<213> ORGANISM: Human papillomavirus

<400> SEQUENCE: 781
tctattccta atgtatacac acctaccagt tttaa                                 35

<210> SEQ ID NO 782
<211> LENGTH: 31
<212> TYPE: DNA
<213> ORGANISM: Human papillomavirus

<400> SEQUENCE: 782
tcctagtagt tatgtatatg ccccctcgcc t                                     31

<210> SEQ ID NO 783
<211> LENGTH: 30
<212> TYPE: DNA
<213> ORGANISM: Human papillomavirus

<400> SEQUENCE: 783
agtagttatg tatatgcccc ctcgcctagt                                       30

<210> SEQ ID NO 784
<211> LENGTH: 30
<212> TYPE: DNA
<213> ORGANISM: Human papillomavirus
```

<400> SEQUENCE: 784
agtagttatg tgtatgcccc ctcgcctagc                                              30

<210> SEQ ID NO 785
<211> LENGTH: 31
<212> TYPE: DNA
<213> ORGANISM: Human papillomavirus

<400> SEQUENCE: 785
tgaatcagct gtaccaaata tttatgatcc t                                            31

<210> SEQ ID NO 786
<211> LENGTH: 31
<212> TYPE: DNA
<213> ORGANISM: Human papillomavirus

<400> SEQUENCE: 786
agactctact gtaccagctg tgtatgattc t                                            31

<210> SEQ ID NO 787
<211> LENGTH: 30
<212> TYPE: DNA
<213> ORGANISM: Human papillomavirus

<400> SEQUENCE: 787
ttcctccaac aaaaatccta aggacagtag                                              30

<210> SEQ ID NO 788
<211> LENGTH: 29
<212> TYPE: DNA
<213> ORGANISM: Human papillomavirus

<400> SEQUENCE: 788
ttcctccaac aaaaatccta aggacagta                                               29

<210> SEQ ID NO 789
<211> LENGTH: 30
<212> TYPE: DNA
<213> ORGANISM: Human papillomavirus

<400> SEQUENCE: 789
tcctaaggac agtagggaat atgtttcagt                                              30

<210> SEQ ID NO 790
<211> LENGTH: 29
<212> TYPE: DNA
<213> ORGANISM: Human papillomavirus

<400> SEQUENCE: 790
tcagtggact ataaacaaac gcaactatg                                               29

<210> SEQ ID NO 791
<211> LENGTH: 30
<212> TYPE: DNA
<213> ORGANISM: Human papillomavirus

<400> SEQUENCE: 791
tccactacta cagactctac tgtaccagct                                              30

<210> SEQ ID NO 792
<211> LENGTH: 35
<212> TYPE: DNA
<213> ORGANISM: Human papillomavirus

```
<400> SEQUENCE: 792
gctgtaccaa atatttatga tcctaataaa tttaa                              35

<210> SEQ ID NO 793
<211> LENGTH: 33
<212> TYPE: DNA
<213> ORGANISM: Human papillomavirus

<400> SEQUENCE: 793
tttgtctact actactgaat cagctgtacc aaa                                33

<210> SEQ ID NO 794
<211> LENGTH: 35
<212> TYPE: DNA
<213> ORGANISM: Human papillomavirus

<400> SEQUENCE: 794
actgtaccag ctgtgtatga ttctaataaa tttaa                              35

<210> SEQ ID NO 795
<211> LENGTH: 20
<212> TYPE: DNA
<213> ORGANISM: Homo sapiens

<400> SEQUENCE: 795
tgatggtatg gggccaagag                                               20

<210> SEQ ID NO 796
<211> LENGTH: 45
<212> TYPE: DNA
<213> ORGANISM: Homo sapiens

<400> SEQUENCE: 796
gaggtctaag tgatgacagc cgctgagggt ttgaagtcca actcc                   45

<210> SEQ ID NO 797
<211> LENGTH: 46
<212> TYPE: DNA
<213> ORGANISM: Homo sapiens

<400> SEQUENCE: 797
aatctactcc caggagcagg gctagtgaac acagttgtgt cagaag                  46

<210> SEQ ID NO 798
<211> LENGTH: 20
<212> TYPE: DNA
<213> ORGANISM: Homo sapiens

<400> SEQUENCE: 798
gagtcagatg caccatggtg                                               20

<210> SEQ ID NO 799
<211> LENGTH: 46
<212> TYPE: DNA
<213> ORGANISM: Homo sapiens

<400> SEQUENCE: 799
tgaggtctaa gtgatgacag ccgctgaggg tttgaagtcc aactcc                  46

<210> SEQ ID NO 800
<211> LENGTH: 46
<212> TYPE: DNA
<213> ORGANISM: Homo sapiens
```

```
<400> SEQUENCE: 800
aatctactcc caggagcagg gaagtgaaca cagttgtgtc agaagc         46

<210> SEQ ID NO 801
<211> LENGTH: 20
<212> TYPE: DNA
<213> ORGANISM: Homo sapiens

<400> SEQUENCE: 801
agggctgagg gtttgaagtc                                      20

<210> SEQ ID NO 802
<211> LENGTH: 45
<212> TYPE: DNA
<213> ORGANISM: Homo sapiens

<400> SEQUENCE: 802
tgaggtctaa gtgatgacag ccgcaactcc taagccagtg ccaga          45

<210> SEQ ID NO 803
<211> LENGTH: 44
<212> TYPE: DNA
<213> ORGANISM: Homo sapiens

<400> SEQUENCE: 803
ctagggttgg ccaatctact cccaatagat ggctctgccc tgac           44

<210> SEQ ID NO 804
<211> LENGTH: 22
<212> TYPE: DNA
<213> ORGANISM: Homo sapiens

<400> SEQUENCE: 804
tgaacacagt tgtgtcagaa gc                                   22

<210> SEQ ID NO 805
<211> LENGTH: 33
<212> TYPE: DNA
<213> ORGANISM: Homo sapiens

<400> SEQUENCE: 805
ataaaagtca gggcagagcc atctattgct tac                       33

<210> SEQ ID NO 806
<211> LENGTH: 30
<212> TYPE: DNA
<213> ORGANISM: Homo sapiens

<400> SEQUENCE: 806
tcagggcaga gccatctatt gcttacattt                           30

<210> SEQ ID NO 807
<211> LENGTH: 35
<212> TYPE: DNA
<213> ORGANISM: Homo sapiens

<400> SEQUENCE: 807
gtcagggcag agccatctat tgcttacatt tgctt                     35

<210> SEQ ID NO 808
<211> LENGTH: 35
<212> TYPE: DNA
<213> ORGANISM: Homo sapiens
```

```
<400> SEQUENCE: 808
agggcaggag ccagggctgg gcataaaagt caggg                              35

<210> SEQ ID NO 809
<211> LENGTH: 35
<212> TYPE: DNA
<213> ORGANISM: Homo sapiens

<400> SEQUENCE: 809
aaagtcaggg cagagccatc tattgcttac atttg                              35

<210> SEQ ID NO 810
<211> LENGTH: 28
<212> TYPE: DNA
<213> ORGANISM: Homo sapiens

<400> SEQUENCE: 810
tgggcataaa agtcagggca gagccatc                                      28

<210> SEQ ID NO 811
<211> LENGTH: 35
<212> TYPE: DNA
<213> ORGANISM: Homo sapiens

<400> SEQUENCE: 811
caggagcagg gagggcagga gccagggctg ggcat                              35

<210> SEQ ID NO 812
<211> LENGTH: 29
<212> TYPE: DNA
<213> ORGANISM: Homo sapiens

<400> SEQUENCE: 812
cagggagggc aggagccagg gctgggcat                                     29

<210> SEQ ID NO 813
<211> LENGTH: 27
<212> TYPE: DNA
<213> ORGANISM: Homo sapiens

<400> SEQUENCE: 813
caggagcagg gagggcagga gccaggg                                       27

<210> SEQ ID NO 814
<211> LENGTH: 25
<212> TYPE: DNA
<213> ORGANISM: Homo sapiens

<400> SEQUENCE: 814
gactataaac atgctttccg tggca                                         25

<210> SEQ ID NO 815
<211> LENGTH: 2084
<212> TYPE: DNA
<213> ORGANISM: Human papillomavirus

<400> SEQUENCE: 815
ttcctaaagt atcaggatta caatacaggg tatttagaat acatttacct gaccccaata    60
agtttggttt tcctgacacc tcatttata atccagatac acagcggctg gtttgggcct   120
gtgtaggtgt tgaggtaggt cgtggtcagc cattaggtgt gggcattagt ggccatcctt   180
tattaaataa attggatgac acagaaaatg ctagtgctta tgcagcaaat gcaggtgtgg   240
```

```
ataatagaga atgtatatct atggattaca aacaaacaca attgtgttta attggttgca    300
aaccacctat aggggaacac tggggcaaag gatccccatg taccaatgtt gcagtaaatc    360
caggtgattg tccaccatta gagttaataa acacagttat tcaggatggt gatatggttc    420
atactggctt tggtgctatg gactttacta cattacaggc taacaaaagt gaagttccac    480
tggatatttg tacatctatt tgcaaatatc cagattatat taaaatggtg tcagaaccat    540
atggcgacag cttattttt tatttacgaa gggaacaaat gtttgttaga catttattta    600
atagggctgg tactgttggt gaaaatgtac cagacgattt atacattaaa ggctctgggt    660
ctactgcaaa tttagccagt tcaaattatt ttcctacacc tagtggttct atggttacct    720
ctgatgccca aatattcaat aaaccttatt ggttacaacg agcacagggc cacaataatg    780
gcatttgttg gggtaaccaa ctatttgtta ctgttgttga tactacacgc agtacaaata    840
tgtcattatg tgctgccata tctacttcag aaactacata taaaaatact aactttaagg    900
agtacctacg acatggggag gaatatgatt tacagtttat ttttcaactg tgcaaaataa    960
ccttaactgc agacgttatg acatacatac attctatgaa ttccactatt ttggaggact   1020
ggaatttttgg tctacaacct cccccaggag gcacactaga agatacttat aggtttgtaa   1080
cccaggcaat tgcttgtcaa aaacatacac ctccagcacc taaagaagat gatcccctta   1140
aaaaatacac ttttttgggaa gtaaatttaa aggaaaagtt ttctgcagac ctagatcagt   1200
ttcctttagg acgcaaattt ttactacaag caggattgaa ggccaaacca aaatttacat   1260
taggaaaacg aaaagctaca cccaccacct catctacctc tacaactgct aaacgcaaaa   1320
aacgtaagct gtaagtattg tatgtatgtt gaattagtgt tgtttgttgt gtatatgttt   1380
gtatgtgctt gtatgtgctt gtaaatatta agttgtatgt gtgtttgtat gtatggtata   1440
ataaacacgt gtgtatgtgt ttttaaatgc ttgtgtaact attgtgtcat gcaacataaa   1500
taaacttatt gtttcaacac ctactaattg tgttgtggtt attcattgta tataaactat   1560
atttgctaca tcctgttttt gttttatata tactatattt tgtagcgcca ggcccatttt   1620
gtagcttcaa ccgaattcgg ttgcatgctt tttggcacaa aatgtgtttt tttaaatagt   1680
tctatgtcag caactatggt ttaaacttgt acgtttcctg cttgccatgc gtgccaaatc   1740
cctgttttcc tgacctgcac tgcttgccaa ccattccatt gttttttaca ctgcactatg   1800
tgcaactact gaatcactat gtacattgtg tcatataaaa taaatcacta tgcgccaacg   1860
ccttacatac cgctgttagg cacatatttt tggcttgttt taactaacct aattgcatat   1920
ttggcataag gtttaaactt ctaaggccaa ctaaatgtca ccctagttca tacatgaact   1980
gtgtaaaggt tagtcataca ttgttcattt gtaaaactgc acatgggtgt gtgcaaaccg   2040
attttgggtt acacatttac aagcaactta tataataata ctaa                     2084
```